(12) United States Patent
Senger et al.

(10) Patent No.: US 8,822,662 B2
(45) Date of Patent: Sep. 2, 2014

(54) DESATURASES AND PROCESS FOR THE PRODUCTION OF POLYUNSATURATED FATTY ACIDS IN TRANSGENIC ORGANISMS

(75) Inventors: Toralf Senger, Heidelberg (DE); Jörg Bauer, Limburgerhof (DE); Johnathan A. Napier, Preston (GB)

(73) Assignee: BASF Plant Science Company GmbH, Ludwigshafen (DE)

( * ) Notice: Subject to any disclaimer, the term of this patent is extended or adjusted under 35 U.S.C. 154(b) by 186 days.

(21) Appl. No.: 13/139,014

(22) PCT Filed: Dec. 8, 2009

(86) PCT No.: PCT/EP2009/066569
§ 371 (c)(1),
(2), (4) Date: Jul. 20, 2011

(87) PCT Pub. No.: WO2010/066703
PCT Pub. Date: Jun. 17, 2010

(65) Prior Publication Data
US 2011/0277043 A1    Nov. 10, 2011

(30) Foreign Application Priority Data

Dec. 12, 2008 (EP) .................... 08171520
Feb. 3, 2009 (EP) .................... 09151937

(51) Int. Cl.
*C07H 21/04* (2006.01)
*C12P 7/64* (2006.01)
*C12N 15/00* (2006.01)
*C12N 1/20* (2006.01)

(52) U.S. Cl.
USPC ....... 536/23.2; 435/134; 435/189; 435/320.1; 435/253.3

(58) Field of Classification Search
None
See application file for complete search history.

(56) References Cited

U.S. PATENT DOCUMENTS

| | | | |
|---|---|---|---|
| 5,614,393 | A | 3/1997 | Thomas et al. |
| 5,952,544 | A | 9/1999 | Browse et al. |
| 6,043,411 | A | 3/2000 | Nishizawa et al. |
| 2005/0132442 | A1* | 6/2005 | Yadav et al. ............... 800/281 |
| 2007/0249026 | A1 | 10/2007 | Xue et al. |
| 2009/0158462 | A1 | 6/2009 | Cirpus et al. |
| 2010/0212034 | A1 | 8/2010 | Cirpus et al. |
| 2010/0227924 | A1 | 9/2010 | Cirpus et al. |

FOREIGN PATENT DOCUMENTS

| | | |
|---|---|---|
| DE | 10 2006 008 030 A1 | 8/2007 |
| EP | 0 550 162 A1 | 7/1993 |
| EP | 0 794 250 A1 | 9/1997 |
| WO | WO-91/13972 A1 | 9/1991 |
| WO | WO-93/06712 A1 | 4/1993 |
| WO | WO-93/11245 A1 | 6/1993 |
| WO | WO-94/11516 A1 | 5/1994 |
| WO | WO-94/18337 A1 | 8/1994 |
| WO | WO-95/18222 A1 | 7/1995 |
| WO | WO-96/21022 A2 | 7/1996 |
| WO | WO-97/21340 A1 | 6/1997 |
| WO | WO-97/30582 A1 | 8/1997 |
| WO | WO-98/46763 A1 | 10/1998 |
| WO | WO-98/46764 A1 | 10/1998 |
| WO | WO-98/46765 A1 | 10/1998 |
| WO | WO-98/46776 A2 | 10/1998 |
| WO | WO-99/27111 A1 | 6/1999 |
| WO | WO-99/64616 A2 | 12/1999 |
| WO | WO-00/21557 A1 | 4/2000 |
| WO | WO-2004/057001 A2 | 7/2004 |
| WO | WO-2005/083053 A1 | 9/2005 |
| WO | WO-2006/100241 A2 | 9/2006 |
| WO | WO-2007/093776 A2 | 8/2007 |
| WO | WO-2008/104559 A1 | 9/2008 |

OTHER PUBLICATIONS

Devos et al., Proteins: Structure, Function and Genetics, 2000, vol. 41: 98-107.*
Witkowski et al., (Biochemistry 38:11643-11650, 1999.*
Whisstock et al., Quarterly Reviews of Biophysics 2003, vol. 36 (3): 307-340.*
Kisselev L., Structure, 2002, vol. 10: 8-9.*
Abbadi, A., et al., "Biosynthesis of Very-Long-Chain Polyunsaturated Fatty Acids in Transgenic Oilseeds: Constraints on Their Accumulation," The Plant Cell, (Oct. 2004), vol. 16, pp. 2734-2748.
Akimoto, M., et al., "Carbon Dioxide Fixation and Polyunsaturated Fatty Acid Production by the Red Aga *Porphyridium cruentum*," Applied Biochemistry and Biotechnology, (1998), vol. 73, pp. 269-278.
Beaudoin, F., et al., "Production of $C_{20}$ polyunsaturated fatty acids (PUFAs) by pathway engineering: identification of PUFA elongase component from *Caenorhabditis elegans*," Biochem Soc Trans, (2000), vol. 28, pp. 661-663.
Calder, P.C., "Dietary modification of inflammation with lipids," Proceedings of the Nutrition Society, (2002), vol. 61, pp. 345-358.
Cleland, L.G., et al., "Fish Oil and Rheumatoid Arthritis: Antiinflammatory and Collateral Health Benefits," J. Rheumatol., (2000), vol. 27, pp. 2305-2307.

(Continued)

Primary Examiner — Tekchand Saidha
Assistant Examiner — Md. Younus Meah
(74) Attorney, Agent, or Firm — Drinker Biddle & Reath LLP

(57) ABSTRACT

The present invention relates to polynucleotides from *Cochliobolus heterostrophus* C5, *Cyanothece* sp. CCY0110, *Mycocentrospora acerina* and *Hyaloperonospora parasitica*, which code for desaturases and which can be employed for the recombinant production of polyunsaturated fatty acids. The invention furthermore relates to vectors, host cells and transgenic nonhuman organisms which comprise the polynucleotides according to the invention, and to the polypeptides encoded by the polynucleotides. The invention furthermore relates to antibodies against the polypeptides according to the invention. Finally, the invention also relates to production processes for the polyunsaturated fatty acids and for oil, lipid and fatty acid compositions and to their use as drugs, cosmetics, foodstuffs, feedstuffs, preferably fish food, or food supplements.

19 Claims, 2 Drawing Sheets

(56) References Cited

OTHER PUBLICATIONS

Figure 1:
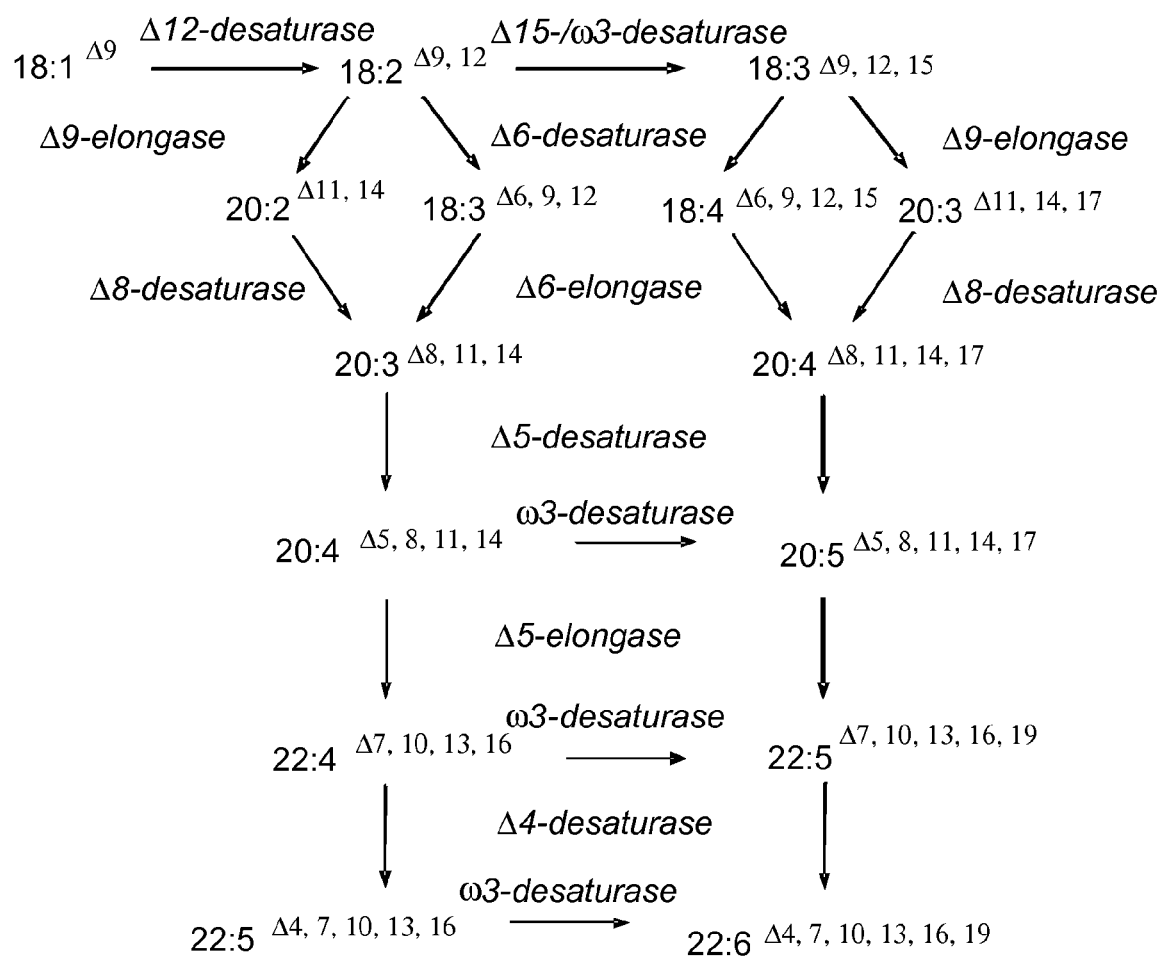

Domergue, F., et al., "Cloning and functional characterization of *Phaeodactylum tricornutum* front-end desaturases involved in eicosapentaenoic acid biosynthesis," Eur. J. Biochem., (2002), vol. 269, pp. 4105-4113.

Gerhardt, B., "Fatty Acid Degradation in Plants," Prog. Lipid Res., (1992), vol. 31, No. 4, pp. 417-446.

Gühnemann-Schäfer, K., et al., "Fatty acid β-oxidation in glyoxysomes. Characterization of a new tetrafunctional protein (MFP III)," Biochimica et Biophysica Acta, (1995), vol. 1256, pp. 181-186.

Horrocks, L.A., et al., "Health Benefits of Docosahexaenoic Acid (DHA)," Pharmacological Research, (1999), vol. 40, No. 3, pp. 211-225.

Huang, Y., et al., "Cloning of Δ12- and Δ6-Desaturases from *Mortierella alpina* and Recombinant Production of γ-Linolenic Acid in *Saccharomyces cerevisiae*," Lipids, (1999), vol. 34, No. 7, pp. 649-659.

Kinney, A.J., "Genetic Engineering of Oilseeds for Desired Traits," Genetic Engineering, (1997), vol. 19, pp. 149-166.

Kunau, W., et al., "β-Oxidation of Fatty Acids in Mitochondria, Peroxisomes, and Bacteria: A Century of Continued Progress," Prog. Lipid Res., (1995), vol. 34, No. 4, pp. 267-342.

"CCBO422.b1 CCO *Cochliobolus heterostrophus*, Chet minimal *Cochliobolus heterostrophus* cDNA clone CCBO422 5', mRNA sequence," EMBL Database, Accession No. FK677023, Jul. 8, 2008.

McKeon, T., et al., "Acyl-Acyl Carrier Protein Thioesterase from Safflower," Methods in Enzymology, (1981), vol. 71, Part C, pp. 12141-12147.

Michaelson, L.V., et al., "Functional identification of a fatty acid Δ$^5$ desaturase gene from *Caenorhabditis elegans*," FEBS Letters, (1998), vol. 439, pp. 215-218.

Mikolajczak, K.L., et al., "Search for New Industrial Oils. V. Oils of Cruciferae," Journal of the American Oil Chemical Society, (1961), vol. 38, pp. 678-681.

Murphy, D.J., et al., "Biosynthesis, targeting and processing of oleosin-like proteins, which are major pollen coat components in *Brassica napus*," The Plant Journal, (1998), vol. 13, No. 1, pp. 1-16.

Napier, J.A., et al., "Genomic and Functional Characterization of Polyunsaturated Fatty Acid Biosynthesis in *Caenorhabditis elegans*," Lipids, (2001), vol. 36, No. 8, pp. 761-766.

Napier, J.A., et al., "Progress towards the production of very long-chain polyunsaturated fatty acid in transgenic plants: plant metabolic engineering comes of age," Physiologia Plantarum, (2006), vol. 126, pp. 398-406.

Ohlrogge, J., et al., "Lipid Biosynthesis," The Plant Cell, (Jul. 1995), vol. 7, pp. 957-970.

Poulos, A., "Very Long Chain Fatty Acids in Higher Animals—A Review," Lipids, (1995), vol. 30, No. 1, pp. 1-14.

Qiu, X., et al., "Identification of a Δ4 Fatty Acid Desaturase from *Thraustochytrium* sp. Involved in the Biosynthesis of Docosahexanoic Acid by Heterologous Expression in *Saccharomyces cerevisiae* and *Brassica juncea*," The Journal of Biological Chemistry, (Aug. 24, 2001), vol. 276, No. 34, pp. 31561-31566.

Sakuradani, E., et al., "Δ6-Fatty acid desaturase from an arachidonic acid-producing *Mortierella* fungus. Gene cloning and its heterologous expression in a fungus, *Aspergillus*," Gene, (1999), vol. 238, pp. 445-453.

Sayanova, O., et al., "A Bifunctional Δ12,Δ15-Desaturase from *Acanthamoeba castellanii* Directs the Syntesis of Highly Unusual n-1 Series Unsaturated Fatty Acids," The Journal of Biological Chemistry, (Dec. 1, 2006), vol. 281, No. 48, pp. 36533-36541.

Sayanova, O., et al., "Mutagenesis and heterologous expression in yeast of a plant Δ$^6$-fatty acid desaturase," Journal of Experimental Botany, (Jul. 2001), vol. 52, No. 360, pp. 1581-1585.

Shanklin, J., et al., "Desaturation and Related Modifications of Fatty Acids," Annu. Rev. Plant Physiol. Plant Mol. Biol., (1998), vol. 49, pp. 611-641.

Shimokawa, H., "Beneficial Effects of Eicosapentaenoic Acid on Endothelial Vasodilator Functions sin Animals and Humans," World Rev Nutr Diet., (2001), vol. 88, pp. 100-108.

Singh, S.P., et al., "Metabolic engineering of new fatty acids in plants," Current Opinion in Plant Biology, (2005), vol. 8, pp. 197-203.

Sperling, P., et al., "Functional Identification of a Δ$^8$-Sphingolipid Desaturase from *Borago officinalis*," Archives of Biochemistry and Biophysics, (Apr. 15, 2001), vol. 388, No. 2, pp. 293-298.

Sprecher, H., "Metabolism of highly unsaturated n-3 and n-6 fatty acids," Biochimica et Biophysica Acta, (2000), vol. 1486, pp. 219-231.

Stukey, J.E., et al., "The *OLE1* Gene of *Saccharomyces cerevisiae* Encodes the Δ9 Fatty Acid Desaturase and Can be Functionally Replaced by the Rat Stearoyl-CoA Desaturase Gene," The Journal of Biological Chemistry, (Nov. 25, 1990), vol. 265, No. 33, pp. 20144-20149.

Stymne, ST., "Biosynthesis of 'Uncommon' Fatty Acids and Their Incorporation into Triacylglycerols," in Biochemistry and Molecular Biology of Membrane and Storage Lipids of Plants, (1993), Ed.: Murata and Somerville, Rockville, American Society of Plant Physiologists, pp. 150-158.

Takeyama, H., et al., "Expression of the eicosapentaenoic acid synthesis gene cluster from *Shewanella* sp. in a transgenic marine cyanobacterium, *Synechococcus* sp.," Microbiology, (1997), vol. 143, pp. 2725-2731.

Thompson, J.D., et al., "CLUSTAL W: improving the sensitivity of progressive multiple sequence alignment through sequence weighting, position-specific gap penalties and weight matrix choice," Nucleic Acids Research, (1994), vol. 22, No. 22, pp. 4673-4680.

Tocher, D.R., et al., "Recent Advances in the Biochemistry and Molecular Biology of Fatty Acyl Desaturases," Prog. Lipid Res., (1998), vol. 37, No. 2/3, pp. 73-117.

Totani, N., et al., "The Filamentous Fungus *Mortierella alpina*, High in Arachidonic Acid," Lipids, (1987), vol. 22, No. 12, pp. 1060-1062.

Uttaro, A.D., "Biosynthesis of Polyunsaturated Fatty Acids in Lower Eukaryotes," IUBMB Life, (Oct. 2006), vol. 58, No. 10, pp. 563-571.

Vazhappilly, R., et al., "Heterotrophic Production Potential of Omega-3 Polyunsaturated Fatty Acids by Microalgae and Algae-like Microorganisms," Botanica Marina, (1998), vol. 41, pp. 553-558.

Voelker, T., "Plant Acyl-ACP Thioesterases: Chain-Length Determining Enzymes in Plant Fatty Acid Biosynthesis," Genetic Engineering, (1996), vol. 18, pp. 111-113,.

Wada, H., et al., "Enhancement of chilling tolerance of a cyanobacterium by genetic manipulation of fatty acid desaturation," Nature, (Sep. 13, 1990), vol. 347, pp. 200-203.

Wang, X.M., et al., "Biosynthesis and regulation of linolenic acid in higher plants," Plant Physiol. Biochem., (1988), vol. 26, No. 6, pp. 777-792.

Yu, R., et al., "Production of Eicosapentaenoic Acid by a Recombinant Marine Cyanobacterium, *Synechococcus* sp.," Lipids, (2000), vol. 35, No. 10, pp. 1061-1064.

Zank, T.K., et al., "Cloning and functional characterisation of an enzyme involved in the elongation of Δ6-polyunsaturated fatty acids from the moss *Physcomitrella patens*," The Plant Journal, (2001), vol. 31, No. 3, pp. 255-268.

Extended European Search Report Dated Nov. 7, 2013 Issued in European Application No. 13180237.3.

\* cited by examiner

2A

2B

2C

SEQUENCE LISTING

<160> NUMBER OF SEQ ID NOS: 56

<210> SEQ ID NO 1
<211> LENGTH: 1870
<212> TYPE: DNA

-continued

<213> ORGANISM: Cochliobolus heterostrophus C5

<400> SEQUENCE: 1
ttgaaatctc ggttcgagac ccactgttac gtaccgccat agacacgaag gcggtgtctg 60
gtgcacatcg ctgccctcgc gacgttgaaa cgtatgtcgg gtccgttgag cttaggctgt 120
atcaaggggc agagttttcg tgctcaaccc agccgctatc ggtacaaaag gctgaccacc 180
gtcccgcccc gtgtctgaac gagtgtccct tccattccct ttcttcccaa ccatgattac 240
gactacgcac cgtgtccacg aggctcctgt caagaccagg cttacggctg tggccgatgt 300
ccggcccatt cccgacgtca agaccctcaa ggatgccatt cccgcaaaat gctttgagcg 360
ctccatgctt cgctccttct cttacgtcgt ccgtgatctc attgtcgtct tctccctttt 420
ctacgctgct gtgcccctgt ctcgcctaga cgctccctgg ttcgtcacag ttcccctgtg 480
ggccctatac agcttcgtcc agggctgttt cttcactggt ctctggattc ttgcccacga 540
ttgcggccat gactctttct ccgagaacct caccgtcaac gccattaccg gctggttcct 600
ccactgcatg ttgatggtcc ccttcttcag ctggaagttc agccacgccc gccaccaccg 660
ataccacaac cacatggaca aggacaccgt cttcgtgccc caccgcaagt ccgacgtcga 720
ggccaagaag accaagccaa ccctcctcga gaaaatcatg gaccactcag ccgctgacac 780
gcccatcatc acggtcgctt ctctcatctt ccaccaagtc cttggctggc cagcttacat 840
tctgatgaac gccggcgctg gcaagaagag cttgaccaag ggagaccgct acacttcttc 900
ccgctacaag caaagtcatt tggatcccac tgcccacgta ttcaccccgt ctgaggctcc 960
ttttgtcgct ctgagcaatg tcggcctcat cctcacaatg actgctctgt atgtctggtc 1020
ccgcagcgtt ggaacttcga ccgttcttct cgcgtatggt ctcccttacc tctggatgaa 1080
ccactggatc ggtaagcgtg tcgttccccc gagctgcaaa gtagtgaaaa ctaattctcc 1140
acagtcgcta ttacttacct tcaccacact caccccgagg ctcctcacta cgaggctgac 1200
aactggactt ttatcaaggg cgctgcctca actgtggacc gtgattttgg cttcattggc 1260
cgccacatct tccacggcat cattgagtac cacgtcgttc accacatgtt cccgtaagtt 1320
tgacctatac cgagccacca ccatgtcttg gtcactccaa ctcttcgcgc tgagcccagc 1380
tgacgtgtat tagacgcatt cccttctacc acgccgagga ggccacttgg gctattgccc 1440
ctcttcttgg cgaacgctac atccagcaaa agaccaactt tttcggtgac ttgtggcaaa 1500
gcttcaccac ttgcaagacc gttgagccgg gcactggcgt ccacgctgga ggattggtct 1560
ggtccaagac caaggcttaa ggcttgcgca gtttggtttg cgaaatgaaa cgaggcaaat 1620
gaaattagac tctagacaat agaaggttta atccgatcct atctttcagt aatcccgggt 1680
acatgcctaa acacaacttg gtgagatgat atgttggcac gaaagattta gttggtgctg 1740
cttaggtgaa ttgccgactg atgacgtcgt gtgttgatca tctccggtca cgtgaataca 1800
caaggtggtg caggcactcc aacttgtttg agctgactga tcgagagaac tccttgatct 1860
ccagaattaa 1870

<210> SEQ ID NO 2
<211> LENGTH: 1215
<212> TYPE: DNA
<213> ORGANISM: Cochliobolus heterostrophus C5

<400> SEQUENCE: 2
atgattacga ctacgcaccg tgtccacgag gctcctgtca agaccaggct tacggctgtg 60
gccgatgtcc ggcccattcc cgacgtcaag accctcaagg atgccattcc cgcaaaatgc 120

```
tttgagcgct ccatgcttcg ctccttctct tacgtcgtcc gtgatctcat tgtcgtcttc      180
tcccttttct acgctgctgt gcccctgtct cgcctagacg ctcccctggtt cgtcacagtt      240 cccctgtggg ccctatacag cttcgtccag ggctgtttct tcactggtct ctggattctt      300
gcccacgatt gcggccatga ctctttctcc gagaacctca ccgtcaacgc cattaccggc      360
tggttcctcc actgcatgtt gatggtcccc ttcttcagct ggaagttcag ccacgcccgc      420
caccaccgat accacaacca catggacaag gacaccgtct cgtgcccca ccgcaagtcc       480 gacgtcgagg ccaagaagac caagccaacc ctcctcgaga aaatcatgga ccactcagcc      540
gctgacacgc ccatcatcac ggtcgcttct ctcatcttcc accaagtcct ggctggcca       600 gcttacattc tgatgaacgc cggcgctggc aagaagagct tgaccaaggg agaccgctac      660
acttcttccc gctacaagca aagtcatttg atcccactg cccacgtatt caccccgtct       720
gaggctcctt tgtcgctct gagcaatgtc ggcctcatcc tcacaatgac tgctctgtat       780
gtctggtccc gcagcgttgg aacttcgacc gttcttctcg cgtatggtct cccttacctc      840
tggatgaacc actggatcgt cgctattact taccttcacc acactcaccc cgaggctcct      900
cactacgagg ctgacaactg gactttatc aagggcgctg cctcaactgt ggaccgtgat       960
tttggcttca ttggccgcca catcttccac ggcatcattg agtaccacgt cgttcaccac     1020
atgttcccac gcattccctt ctaccacgcc gaggaggcca cttgggctat tgcccctctt     1080
cttggcgaac gctacatcca gcaaaagacc aacttttcg gtgacttgtg caaagcttc      1140 accacttgca agaccgttga gccgggcact ggcgtccacg ctggaggatt ggtctggtcc     1200
aagaccaagg cttaa                                                       1215

<210> SEQ ID NO 3
<211> LENGTH: 404
<212> TYPE: PRT
<213> ORGANISM: Cochliobolus heterostrophus C5

<400> SEQUENCE: 3

Met Ile Thr Thr Thr His Arg Val His Glu Ala Pro Val Lys Thr Arg
1               5                   10                  15

Leu Thr Ala Val Ala Asp Val Arg Pro Ile Pro Asp Val Lys Thr Leu
            20                  25                  30

Lys Asp Ala Ile Pro Ala Lys Cys Phe Glu Arg Ser Met Leu Arg Ser
        35                  40                  45

Phe Ser Tyr Val Val Arg Asp Leu Ile Val Val Phe Ser Leu Phe Tyr
    50                  55                  60

Ala Ala Val Pro Leu Ser Arg Leu Asp Ala Pro Trp Phe Val Thr Val
65                  70                  75                  80

Pro Leu Trp Ala Leu Tyr Ser Phe Val Gln Gly Cys Phe Phe Thr Gly
                85                  90                  95

Leu Trp Ile Leu Ala His Asp Cys Gly His Asp Ser Phe Ser Glu Asn
            100                 105                 110

Leu Thr Val Asn Ala Ile Thr Gly Trp Phe Leu His Cys Met Leu Met
        115                 120                 125

Val Pro Phe Phe Ser Trp Lys Phe Ser His Ala Arg His His Arg Tyr
    130                 135                 140

His Asn His Met Asp Lys Asp Thr Val Phe Val Pro His Arg Lys Ser
145                 150                 155                 160

Asp Val Glu Ala Lys Lys Thr Lys Pro Thr Leu Leu Glu Lys Ile Met
                165                 170                 175
```

-continued

```
Asp His Ser Ala Ala Asp Thr Pro Ile Ile Thr Val Ala Ser Leu Ile
            180                 185                 190

Phe His Gln Val Leu Gly Trp Pro Ala Tyr Ile Leu Met Asn Ala Gly
        195                 200                 205

Ala Gly Lys Lys Ser Leu Thr Lys Gly Asp Arg Tyr Thr Ser Ser Arg
    210                 215                 220

Tyr Lys Gln Ser His Leu Asp Pro Thr Ala His Val Phe Thr Pro Ser
225                 230                 235                 240

Glu Ala Pro Phe Val Ala Leu Ser Asn Val Gly Leu Ile Leu Thr Met
                245                 250                 255

Thr Ala Leu Tyr Val Trp Ser Arg Ser Val Gly Thr Ser Thr Val Leu
            260                 265                 270

Leu Ala Tyr Gly Leu Pro Tyr Leu Trp Met Asn His Trp Ile Val Ala
        275                 280                 285

Ile Thr Tyr Leu His His Thr His Pro Glu Ala Pro His Tyr Glu Ala
    290                 295                 300

Asp Asn Trp Thr Phe Ile Lys Gly Ala Ala Ser Thr Val Asp Arg Asp
305                 310                 315                 320

Phe Gly Phe Ile Gly Arg His Ile Phe His Gly Ile Ile Glu Tyr His
                325                 330                 335

Val Val His His Met Phe Pro Arg Ile Pro Phe Tyr His Ala Glu Glu
            340                 345                 350

Ala Thr Trp Ala Ile Ala Pro Leu Leu Gly Glu Arg Tyr Ile Gln Gln
        355                 360                 365

Lys Thr Asn Phe Phe Gly Asp Leu Trp Gln Ser Phe Thr Thr Cys Lys
    370                 375                 380

Thr Val Glu Pro Gly Thr Gly Val His Ala Gly Gly Leu Val Trp Ser
385                 390                 395                 400

Lys Thr Lys Ala
```

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
atgattacga ctacgcacc                                                19

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gcggccgcgc catgattacg actacgcacc                                    30

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6

| | |
|---|---|
| ttaagccttg gtcttggacc | 20 |

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7

| | |
|---|---|
| gcggccgcgt taagccttgg tcttggacc | 29 |

<210> SEQ ID NO 8
<211> LENGTH: 1667
<212> TYPE: DNA
<213> ORGANISM: Cyanothece sp. CCY0110

<400> SEQUENCE: 8

| | |
|---|---|
| gagatgatga cttaacccgt acctttcgtc gaaatcctcc attaccacca cgaggagaat | 60 |
| ggaacgatta aaggattttg cttttttgtta ctaatgtcgg taaacagtcc ccaagctata | 120 |
| aagggcgcaa gttttgcgcc ttttaatttt gaaagtagaa aaaattgacc ccaacaccat | 180 |
| ctagagcaaa ggttcttgaa gtagtaactt gtaacagtag agtatgtcaa ctgctaatag | 240 |
| tataataggt aagattaaga aaaattaagt ttttctcgac attaggttta aataaggaga | 300 |
| tccaacagcg aatgcagcaa cctatgactg tgaagcgacc agaaccaaaa gtggtcgacc | 360 |
| tacctttac gttacaagat attagagaag ccatccccccc tcattgtttt gagtcatctg | 420 |
| ctataaaatc cctggcttat ttttttttggg atattttttgt catatctgtt ctatatgcga | 480 |
| tcgcttattc tttggattct tggttttttt ggccgatttt ttgggtcatg caaggaacta | 540 |
| tgttttgggc attattgtt gtcggacatg attgtggcca tggttctttt tctcgctaca | 600 |
| aatggttaaa taatctcatt ggtcatcttt cccatactcc cattttagtc ccatttcatg | 660 |
| ggtggcgtat tagtcatcgc actcatcata aaaatactgg taatattgat acggatgaaa | 720 |
| gttggtatcc tatcacagaa tctaaatata atgagatggg atggttagaa aagtttgccc | 780 |
| gttttaaact ggttttatt ctgtatcctc tttatttatt taagcgttcc ccagggagaa | 840 |
| aaggaagtca tttcgatcct aagagcgatc tattccgtcc atctgaaaaa tgggatgttt | 900 |
| taactagcac tatttgcttg attggtatgg ttgctttgtt aggtttttta acttatcaat | 960 |
| tcggcttttt gtggttactt aaatattatt taggaccctta tcttgttttt gtgatttggt | 1020 |
| tagatttagt tacctttta catcacactg atcctgatgt tccttggtat cgggggaaag | 1080 |
| attggtactt tttaaaaggg gcattatcta cggtagatca tgattatggg tttatcaatg | 1140 |
| atatccatca taatattggt actcatgttg ctcatcatat ctttttgacc atgcctcatt | 1200 |
| accatttaaa aaccgcaaca gaagccatta aacccgtttt aggtgactat tatcgtaagt | 1260 |
| caaattactc tatttagaa gcatttattc ggggctacaa tatttgtcat gtggttcccg | 1320 |
| atgaaggggg taaggtttat tgtgaatcta gaaagtttta agtttaattt cttcttctta | 1380 |
| gttataaaaa acacaatcga attaatataa aaagggaag gtattaata agtatcttcc | 1440 |
| ttttactata gaatgaagaa aaaaaataaa atttcaaatt tcctagtata aatatatttg | 1500 |
| caaagaatta tagagaagtt aaatgtaaac aagatcaaga aaacaagtta ataaaaaaat | 1560 |
| ggaaattaga agagaataat ttatattcat tatgaatgta atacattgat ctattgttaa | 1620 |
| ctttttccaat ttttagaata attctgtaac ctattgtaaa aacagaa | 1667 |

<210> SEQ ID NO 9
<211> LENGTH: 1050
<212> TYPE: DNA
<213> ORGANISM: Cyanothece sp. CCY0110

<400> SEQUENCE: 9

```
atgcagcaac ctatgactgt gaagcgacca gaaccaaaag tggtcgacct acctttttacg      60
ttacaagata ttagagaagc atccccccct cattgttttg agtcatctgc tataaaatcc     120
ctggcttatt ttttttggga tatttttgtc atatctgttc tatatgcgat cgcttattct     180
ttggattctt ggttttttttg gccgattttt tgggtcatgc aaggaactat gttttgggca     240
ttatttgttg tcggacatga ttgtggccat ggttcttttt ctcgctacaa atggttaaat     300
aatctcattg gtcatctttc ccatactccc attttagtcc catttcatgg gtggcgtatt     360
agtcatcgca ctcatcataa aaatactggt aatattgata cggatgaaag ttggtatcct     420
atcacagaat ctaaatataa tgagatggga tggttagaaa agtttgcccg ttttaaactg     480
gttttatttc tgtatcctct ttatttattt aagcgttccc cagggagaaa aggaagtcat     540
ttcgatccta agagcgatct attccgtcca tctgaaaaat gggatgtttt aactagcact     600
atttgcttga ttggtatggt tgctttgtta ggttttttaa cttatcaatt cggcttttg     660
tggttactta atattatttt aggaccttat cttgtttttg tgatttggtt agatttagtt     720
acctttttac atcacactga tcctgatgtt ccttggtatc gggggaaaga ttggtacttt     780
ttaaaagggg cattatctac ggtagatcat gattatgggt ttatcaatga tatccatcat     840
aatattggta ctcatgttgc tcatcatatc tttttgacca tgcctcatta ccattttaaa     900
accgcaacag aagccattaa acccgttttta ggtgactatt atcgtaagtc aaattactct     960
attttagaag catttattcg gggctacaat atttgtcatg tggttcccga tgaagggggt    1020
aaggtttatt gtgaatctag aaagttttaa                                      1050
```

<210> SEQ ID NO 10
<211> LENGTH: 349
<212> TYPE: PRT
<213> ORGANISM: Cyanothece sp. CCY0110

<400> SEQUENCE: 10

```
Met Gln Gln Pro Met Thr Val Lys Arg Pro Glu Pro Lys Val Val Asp
1               5                   10                  15

Leu Pro Phe Thr Leu Gln Asp Ile Arg Glu Ala Ile Pro Pro His Cys
            20                  25                  30

Phe Glu Ser Ser Ala Ile Lys Ser Leu Ala Tyr Phe Phe Trp Asp Ile
        35                  40                  45

Phe Val Ile Ser Val Leu Tyr Ala Ile Ala Tyr Ser Leu Asp Ser Trp
    50                  55                  60

Phe Phe Trp Pro Ile Phe Trp Val Met Gln Gly Thr Met Phe Trp Ala
65                  70                  75                  80

Leu Phe Val Val Gly His Asp Cys Gly His Gly Ser Phe Ser Arg Tyr
                85                  90                  95

Lys Trp Leu Asn Asn Leu Ile Gly His Leu Ser His Thr Pro Ile Leu
            100                 105                 110

Val Pro Phe His Gly Trp Arg Ile Ser His Arg Thr His His Lys Asn
        115                 120                 125

Thr Gly Asn Ile Asp Thr Asp Glu Ser Trp Tyr Pro Ile Thr Glu Ser
    130                 135                 140

Lys Tyr Asn Glu Met Gly Trp Leu Glu Lys Phe Ala Arg Phe Lys Leu
```

```
                        145                 150                 155                 160
                Val Leu Phe Leu Tyr Pro Leu Tyr Leu Phe Lys Arg Ser Pro Gly Arg
                                    165                 170                 175

Lys Gly Ser His Phe Asp Pro Lys Ser Asp Leu Phe Arg Pro Ser Glu
                                    180                 185                 190

Lys Trp Asp Val Leu Thr Ser Thr Ile Cys Leu Ile Gly Met Val Ala
                                    195                 200                 205

Leu Leu Gly Phe Leu Thr Tyr Gln Phe Gly Phe Leu Trp Leu Leu Lys
                                    210                 215                 220

Tyr Tyr Leu Gly Pro Tyr Leu Val Phe Ile Trp Leu Asp Leu Val
                225                 230                 235                 240

Thr Phe Leu His His Thr Asp Pro Asp Val Pro Trp Tyr Arg Gly Lys
                                    245                 250                 255

Asp Trp Tyr Phe Leu Lys Gly Ala Leu Ser Thr Val Asp His Asp Tyr
                                    260                 265                 270

Gly Phe Ile Asn Asp Ile His His Asn Ile Gly Thr His Val Ala His
                                    275                 280                 285

His Ile Phe Leu Thr Met Pro His Tyr His Leu Lys Thr Ala Thr Glu
                                    290                 295                 300

Ala Ile Lys Pro Val Leu Gly Asp Tyr Tyr Arg Lys Ser Asn Tyr Ser
                305                 310                 315                 320

Ile Leu Glu Ala Phe Ile Arg Gly Tyr Asn Ile Cys His Val Val Pro
                                    325                 330                 335

Asp Glu Gly Gly Lys Val Tyr Cys Glu Ser Arg Lys Phe
                                    340                 345

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
atgcagcaac ctatgactgt g                                                    21

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
gcggccgcgc catgcagcaa cctatgactg tg                                        32

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ttaaaacttt ctagattcac                                                      20

<210> SEQ ID NO 14
<211> LENGTH: 29
<212> TYPE: DNA
<213> ORGANISM: Artificial Sequence
```

```
<220> FEATURE:
<223> OTHER INFORMATION: Primer

<400> SEQUENCE: 14
gcggccgcgt taaaactttc tagattcac                                     29

<210> SEQ ID NO 15
<211> LENGTH: 1932
<212> TYPE: DNA
<213> ORGANISM: Mycocentrospora acerina

<400> SEQUENCE: 15
accctctttc ccctctttcc ttatcgagga ccctcacgac ttgcggttca gggcactcat    60
ccttgaacgg tcagcccaac aataagcgac ctgcatctca acaacagcac ctcaaccgtc   120
attcggttgc ctgttgtcct ttgaagcccc tccagcttct ttactgctcg ctgagacagc   180
cgtcctcgct gccattgcca tcagcattca ctcgacacct tcaccatggc ctcgaccacc   240
gcccgcgctc aagcccctgt gctgaggcgc acgttacca ccgagtctgt gcctccacc     300 atggccaact cgcccaacga ctcgcccaac ggctccgcct caacacgtc gctgtcgtcg    360 ctcggctccg tcgacgacgt gcaggccaag aaggcatcca acggtgtcct tctcgacacg   420
tacggcaacg agttcaagat ccctgacttc accatcaagg acatccgcga tgccatcccc   480
aagcactgct cgagcgctc tgccgcccgc agtcttggct acgttgcccg cgacctggcc    540
atgctcgcca ccaccttcta cctctcctac acattcatca ggcccgagta catctcctcc   600
aaggccgtcc gcgccgtgct gtgggctgga tacactgtca tccagggtct tgttggcacc   660
ggtctctggg ttcttgccca cgagtgcggc caccaggcct ctcccccctc caaggtgctc   720
aacgacaccg tcggctgggt ctgccactct ctcctcctcg tccctactt ctcatggaag    780 atctcccacg gcaagcacca caaggccacc ggccacatga gcgcgacat ggtcttcatt     840 cccaagaccc gcgacgtcta cgctacccgt gtcagcaagc ttatccacga gatctctgag   900
ctagccgagg agactcccat cgttaccttt atccacatgc tcggtcagca gattggcgga   960
tggcagatgt acctctttgc caacgtcact ggccacaccc accacgaccg tcagtccgag  1020
ggcaagggtg ttggcaagca gaacggcatg ttcgtggcg tcaaccactt caacccatcc   1080
agccctctgt acgagaagag ggacgagcac ctcatcctgc ttagcgatct tggccttgct  1140
attgttatcg ctgctctgac ctacgttggc aagattcacg gcttctcaag tgtcctcgtg  1200
tggtacatca tcccttactt ctgggttcac cactggctcg tcatgatcac cttcctccag  1260
cacacggacc cttccctgcc ccactacgac gctgagacgt ggacctacgc ccgtggcgct  1320
ggtgcaacga ttgaccgcga gtttggcttc attggacgca ctctgttcca cggcatcatt  1380
gagacgcacg ttctccacca ctacatctcg tcgattcctt tctacaacgc cgatgaggcc  1440
tctgaggcca tcaagaaggt catgggctcg cactaccgat ctgacgttga gggtggctcc  1500
attggcttcc tcaagtcttt ctggaggagt gcccgcatgt gccagtttgt cgagcccagc  1560
gaaggtgccg agggcgaggg caagggtgtg cttttcttcc gcaaccacaa tggtcttggc  1620
gttcagcccc gcaagctgga tgcgtctggc aagcctgtcg ttagcaagcg cgccaccaag  1680
atggaggtgg gccctgagag tgacaacgag taaagaggct gcaaggccct ttttcggac    1740 tagtgaggca aggttgattt gggtgaaggg gcgttttatg gtagcattga ctcgaagatt  1800
gactttttgg agctgggctg gttacttgat gataaatttt ttttcttcct tcgagcgtta  1860
gagcttagac agcccaagac gatagaagtc gatatcccac ttggaaaaaa aagaaaaaaa  1920
```

-continued aaaaaaaaaa aa 1932

<210> SEQ ID NO 16
<211> LENGTH: 1488
<212> TYPE: DNA
<213> ORGANISM: Mycocentrospora acerina

<400> SEQUENCE: 16
atggcctcga ccaccgcccg cgctcaagcc cctgtgctga ggcgccacgt taccaccgag 60
tctgtgccct ccaccatggc caactcgccc aacgactcgc ccaacggctc cgcctccaac 120
acgtcgctgt cgtcgctcgg ctccgtcgac gacgtgcagg ccaagaaggc atccaacggt 180
gtccttctcg acacgtacgg caacgagttc aagatccctg acttcaccat caaggacatc 240
cgcgatgcca tccccaagca ctgcttcgag cgctctgccg cccgcagtct tggctacgtt 300
gcccgcgacc tggccatgct cgccaccacc ttctacctct cctacacatt catcaggccc 360
gagtacatct cctccaaggc cgtccgcgcc gtgctgtggg ctggatacac tgtcatccag 420
ggtcttgttg gcaccggtct ctgggttctt gcccacgagt gcggccacca ggccttctcc 480
ccctccaagg tgctcaacga caccgtcggc tgggtctgcc actctctcct cctcgtcccc 540
tacttctcat ggaagatctc ccacggcaag caccacaagg ccaccggcca catggagcgc 600
gacatggtct tcattcccaa gacccgcgac gtctacgcta cccgtgtcag caagcttatc 660
cacgagatct ctgagctagc cgaggagact cccatcgtta cctttatcca catgctcggt 720
cagcagattg gcggatggca gatgtacctc tttgccaacg tcactggcca cacccaccac 780
gaccgtcagt ccgagggcaa gggtgttggc aagcagaacg gcatgttcgg tggcgtcaac 840
cacttcaacc catccagccc tctgtacgag aagagggacg agcacctcat cctgcttagc 900
gatcttggcc ttgctattgt tatcgctgct ctgacctacg ttggcaagat tcacggcttc 960
tcaagtgtcc tcgtgtggta catcatccct tacttctggg ttcaccactg gctcgtcatg 1020
atcaccttcc tccagcacac ggacccttcc ctgccccact acgacgctga gacgtggacc 1080
tacgcccgtg gcgctggtgc aacgattgac cgcgagtttg gcttcattgg acgcactctg 1140
ttccacggca tcattgagac gcacgttctc caccactaca tctcgtcgat tcctttctac 1200
aacgccgatg aggcctctga ggccatcaag aaggtcatgg gctcgcacta ccgatctgac 1260
gttgagggtg gctccattgg cttcctcaag tctttctgga ggagtgcccg catgtgccag 1320
tttgtcgagc ccagcgaagg tgccgagggc gagggcaagg gtgtgctttt cttccgcaac 1380
cacaatggtc ttggcgttca gcccccgcaag ctggatgcgt ctggcaagcc tgtcgttagc 1440
aagcgcgcca ccaagatgga ggtgggccct gagagtgaca acgagtaa 1488

<210> SEQ ID NO 17
<211> LENGTH: 495
<212> TYPE: PRT
<213> ORGANISM: Mycocentrospora acerina

<400> SEQUENCE: 17

Met Ala Ser Thr Thr Ala Arg Ala Gln Ala Pro Val Leu Arg Arg His
1 5 10 15

Val Thr Thr Glu Ser Val Pro Ser Thr Met Ala Asn Ser Pro Asn Asp
20 25 30

Ser Pro Asn Gly Ser Ala Ser Asn Thr Ser Leu Ser Ser Leu Gly Ser
35 40 45

Val Asp Asp Val Gln Ala Lys Lys Ala Ser Asn Gly Val Leu Leu Asp
50 55 60

```
Thr Tyr Gly Asn Glu Phe Lys Ile Pro Asp Phe Thr Ile Lys Asp Ile
 65                  70                  75                  80

Arg Asp Ala Ile Pro Lys His Cys Phe Glu Arg Ser Ala Ala Arg Ser
                 85                  90                  95

Leu Gly Tyr Val Ala Arg Asp Leu Ala Met Leu Ala Thr Thr Phe Tyr
            100                 105                 110

Leu Ser Tyr Thr Phe Ile Arg Pro Glu Tyr Ile Ser Ser Lys Ala Val
            115                 120                 125

Arg Ala Val Leu Trp Ala Gly Tyr Thr Val Ile Gln Gly Leu Val Gly
130                 135                 140

Thr Gly Leu Trp Val Leu Ala His Glu Cys Gly His Gln Ala Phe Ser
145                 150                 155                 160

Pro Ser Lys Val Leu Asn Asp Thr Val Gly Trp Val Cys His Ser Leu
                165                 170                 175

Leu Leu Val Pro Tyr Phe Ser Trp Lys Ile Ser His Gly Lys His His
            180                 185                 190

Lys Ala Thr Gly His Met Glu Arg Asp Met Val Phe Ile Pro Lys Thr
            195                 200                 205

Arg Asp Val Tyr Ala Thr Arg Val Ser Lys Leu Ile His Glu Ile Ser
210                 215                 220

Glu Leu Ala Glu Glu Thr Pro Ile Val Thr Phe Ile His Met Leu Gly
225                 230                 235                 240

Gln Gln Ile Gly Gly Trp Gln Met Tyr Leu Phe Ala Asn Val Thr Gly
                245                 250                 255

His Thr His His Asp Arg Gln Ser Glu Gly Lys Gly Val Gly Lys Gln
            260                 265                 270

Asn Gly Met Phe Gly Gly Val Asn His Phe Asn Pro Ser Ser Pro Leu
            275                 280                 285

Tyr Glu Lys Arg Asp Glu His Leu Ile Leu Leu Ser Asp Leu Gly Leu
290                 295                 300

Ala Ile Val Ile Ala Ala Leu Thr Tyr Val Gly Lys Ile His Gly Phe
305                 310                 315                 320

Ser Ser Val Leu Val Trp Tyr Ile Ile Pro Tyr Phe Trp Val His His
                325                 330                 335

Trp Leu Val Met Ile Thr Phe Leu Gln His Thr Asp Pro Ser Leu Pro
            340                 345                 350

His Tyr Asp Ala Glu Thr Trp Thr Tyr Ala Arg Gly Ala Gly Ala Thr
            355                 360                 365

Ile Asp Arg Glu Phe Gly Phe Ile Gly Arg Thr Leu Phe His Gly Ile
370                 375                 380

Ile Glu Thr His Val Leu His His Tyr Ile Ser Ser Ile Pro Phe Tyr
385                 390                 395                 400

Asn Ala Asp Glu Ala Ser Glu Ala Ile Lys Lys Val Met Gly Ser His
                405                 410                 415

Tyr Arg Ser Asp Val Glu Gly Gly Ser Ile Gly Phe Leu Lys Ser Phe
            420                 425                 430

Trp Arg Ser Ala Arg Met Cys Gln Phe Val Glu Pro Ser Glu Gly Ala
            435                 440                 445

Glu Gly Glu Gly Lys Gly Val Leu Phe Phe Arg Asn His Asn Gly Leu
450                 455                 460

Gly Val Gln Pro Arg Lys Leu Asp Ala Ser Gly Lys Pro Val Val Ser
465                 470                 475                 480
```

Lys Arg Ala Thr Lys Met Glu Val Gly Pro Glu Ser Asp Asn Glu
                485                 490                 495

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
atggcctcga ccaccgcccg c                                          21

<210> SEQ ID NO 19
<211> LENGTH: 32
<212> TYPE: DNA
<213> ORGANISM: Artificial Sequence
<220> FEATURE:
<223> OTHER INFORMATION: Primer

<400> SEQUENCE: 19
gcggccgcgc catggcctcg accaccgccc gc                              32

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ttactcgttg tcactctcag                                            20

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
gcggccgcgt tactcgttgt cactctcag                                  29

<210> SEQ ID NO 22
<211> LENGTH: 1380
<212> TYPE: DNA
<213> ORGANISM: Pythium irregulare

<400> SEQUENCE: 22
atggtggacc tcaagcctgg agtgaagcgc ctggtgagct ggaaggagat ccgcgagcac    60
gcgacgcccg cgaccgcgtg gatcgtgatt caccacaagg tctacgacat ctccaagtgg   120
gactcgcacc cgggtggctc cgtgatgctc acgcaggccg cgaggacgc cacggacgcc    180 ttcgcggtct ccacccgtc ctcggcgctc aagctgctcg agcagttcta cgtcggcgac   240
gtggacgaaa cctccaaggc cgagatcgag ggggagccgg cgagcgacga ggagcgcgcg   300
cgccgcgagc gcatcaacga gttcatcgcg tcctaccgtc gtctgcgcgt caaggtcaag   360
ggcatggggc tctacgacgc cagcgcgctc tactacgcgt ggaagctcgt gagcacgttc   420
ggcatcgcgg tgctctcgat ggcgatctgc ttcttcttca acagtttcgc catgtacatg   480
gtcgccggcg tgattatggg gctcttctac cagcagtccg gatggctggc gcacgacttc   540
ttgcacaacc aggtgtgcga gaaccgcacg ctcggcaacc ttatcggctg cctcgtgggc   600

-continued

```
aacgcctggc agggcttcag catgcagtgg tggaagaaca agcacaacct gcaccacgcg        660
gtgccgaacc tgcacagcgc caaggacgag ggcttcatcg cgacccgga catcgacacc         720 atgccgctgc tggcgtggtc taaggagatg gcgcgcaagg cgttcgagtc ggcgcacggc        780
ccgttcttca tccgcaacca ggcgttccta tacttcccgc tgctgctgct cgcgcgcctg        840
agctggctcg cgcagtcgtt cttctacgtg ttcaccgagt tctcgttcgg catcttcgac        900
aaggtcgagt tcgacggacc ggagaaggcg ggtctgatcg tgcactacat ctggcagctc        960
gcgatcccgt acttctgcaa catgagcctg tttgagggcg tggcatactt cctcatgggc       1020
caggcgtcct gcggcttgct cctggcgctg tgttcagta ttggccacaa cggcatgtcg        1080
gtgtacgagc gcgaaaccaa gccggacttc tggcagctgc aggtgaccac gacgcgcaac      1140
atccgcgcgt cggtattcat ggactggttc accggtggct tgaactacca gatcgaccat       1200
cacctgttcc cgctcgtgcc gcgccacaac ttgccaaagg tcaacgtgct catcaagtcg       1260
ctatgcaagg agttcgacat cccgttccac gagaccggct tctgggaggg catctacgag       1320
gtcgtggacc acctggcgga catcagcaag gaattcatca ccgagttccc agcgatgtaa      1380
```

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23

```
gcggccgcgc catggtggac ctcaagcctg g                                        31
```

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24

```
gcggccgtta catcgctggg aactcgg                                             27
```

<210> SEQ ID NO 25
<211> LENGTH: 1320
<212> TYPE: DNA
<213> ORGANISM: Thraustochytrium sp.

<400> SEQUENCE: 25

```
atgggcaagg gcagcgaggg ccgcagcgcg gcgcgcgaga tgacggccga ggcgaacggc         60
gacaagcgga aaacgattct gatcgagggc gtcctgtacg acgcgacgaa ctttaagcac        120
ccgggcggtt cgatcatcaa cttcttgacc gagggcgagg ccggcgtgga cgcgacgcag        180
gcgtaccgcg agtttcatca gcggtccggc aaggccgaca gtacctcaa gtcgctgccg         240 aagctggatg cgtccaaggt ggagtcgcgg ttctcggcca aagagcaggc gcggcgcgac        300
gccatgacgc gcgactacgc ggccttcgc gaggagctcg tcgccgaggg gtactttgac         360
ccgtcgatcc gcacatgat ttaccgcgtc gtggagatct ggcgctctt cgcgctctcg          420 ttctggctca tgtccaaggc ctcgcccacc tcgctcgtgc tgggcgtggt gatgaacggc        480
attgcgcagg gccgctgcgg ctgggtcatg cacgagatgg ccacgggtc gttcacgggc        540 gtcatctggc tcgacgaccg gatgtgcgag ttcttctacg gcgtcggctg cggcatgagc        600
gggcactact ggaagaacca gcacagcaag caccacgccg cgcccaaccg cctcgagcac        660
```

-continued

| | |
|---|---|
| gatgtcgatc tcaacacgct gccsctggtc gcctttaacg agcgcgtcgt gcgcaaggtc | 720 |
| aagccgggat cgctgctggc gctctggctg cgcgtgcagg cgtacctctt tgcgcccgtc | 780 |
| tcgtgcctgc tcatcggcct tggctggacg ctctacctgc acccgcgcta catgctgcgc | 840 |
| accaagcggc acatggagtt cgtctggatc ttcgcgcgct acattggctg gttctcgctc | 900 |
| atgggcgctc tcggctactc gccgggcacc tcggtcggga tgtacctgtg ctcgttcggc | 960 |
| ctcggctgca tttacatttt cctgcagttc gccgtcagcc acacgcacct gccggtgacc | 1020 |
| aacccggagg accagctgca ctggctcgag tacgcggccg accacacggt gaacattagc | 1080 |
| accaagtcct ggctcgtcac gtggtggatg tcgaacctga actttcagat cgagcaccac | 1140 |
| ctcttcccca cggcgccgca gttccgcttc aaggaaatca gtcctcgcgt cgaggccctc | 1200 |
| ttcaagcgcc acaacctccc gtactacgac ctgccctaca cgagcgcggt ctcgaccacc | 1260 |
| tttgccaatc tttattccgt cggccactcg gtcggcgccg acaccaagaa gcaggactga | 1320 |

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26

| | |
|---|---|
| gcggccgcgc catgggcaag ggcagcgagg g | 31 |

<210> SEQ ID NO 27
<211> LENGTH: 32
<212> TYPE: DNA
<213> ORGANISM: Artificial Sequence
<220> FEATURE:
<223> OTHER INFORMATION: Primer

<400> SEQUENCE: 27

| | |
|---|---|
| gcggccgcgc ctcagtcctg cttcttggtg tc | 32 |

<210> SEQ ID NO 28
<211> LENGTH: 1086
<212> TYPE: DNA
<213> ORGANISM: Phytophthora infestans

<400> SEQUENCE: 28

| | |
|---|---|
| atggcgacga aggaggcgta tgtgttcccc actctgacgg agatcaagcg gtcgctacct | 60 |
| aaagactgtt tcgaggcttc ggtgcctctg tcgctctact acaccgtgcg ttgtctggtg | 120 |
| atcgcggtgg ctctaacctt cggtctcaac tacgctcgcg ctctgcccga ggtcgagagc | 180 |
| ttctgggctc tggacgccgc actctgcacg gctacatct tgctgcaggg catcgtgttc | 240 |
| tggggcttct tcacggtggg ccacgatgcc ggccacggcg ccttctcgcg ctaccacctg | 300 |
| cttaacttcg tggtgggcac tttcatgcac tcgctcatcc tcacgccctt cgagtcgtgg | 360 |
| aagctcacgc accgtcacca ccacaagaac acgggcaaca ttgaccgtga cgaggtcttc | 420 |
| tacccgcaac gcaaggccga cgaccacccg ctgtctcgca acctgattct ggcgctcggg | 480 |
| gcagcgtggc tcgcctattt ggtcgagggc ttccctcctc gtaaggtcaa ccacttcaac | 540 |
| ccgttcgagc tctgttcgt gcgtcaggtg tcagctgtgg taatctctct tctcgcccac | 600 |
| ttcttcgtgg ccggactctc catctatctg agctccagc tgggccttaa gacgatggca | 660 |
| atctactact atggacctgt ttttgtgttc ggcagcatgc tggtcattac caccttccta | 720 |

```
caccacaatg atgaggagac cccatggtac gccgactcgg agtggacgta cgtcaagggc       780
aacctctcgt ccgtggaccg atcgtacggc gcgctcattg acaacctgag ccacaacatc       840
ggcacgcacc agatccacca ccttttccct atcattccgc actacaaact caagaaagcc       900
actgcggcct tccaccaggc tttccctgag ctcgtgcgca agagcgacga gccaattatc       960
aaggctttct tccgggttgg acgtctctac gcaaactacg gcgttgtgga ccaggaggcg      1020
aagctcttca cgctaaagga agccaaggcg gcgaccgagg cggcggccaa gaccaagtcc      1080
acgtaa                                                                1086

<210> SEQ ID NO 29
<211> LENGTH: 31
<212> TYPE: DNA
<213> ORGANISM: Artificial Sequence
<220> FEATURE:
<223> OTHER INFORMATION: Primer

<400> SEQUENCE: 29
gcggccgcgc catggcgacg aaggaggcgt a                                      31

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
gcggccgcgt tacgtggact tggtcttggc c                                      31

<210> SEQ ID NO 31
<211> LENGTH: 873
<212> TYPE: DNA
<213> ORGANISM: Physcomitrella patens

<400> SEQUENCE: 31
atggaggtcg tggagagatt ctacggtgag ttggatggga aggtctcgca gggcgtgaat        60
gcattgctgg gtagttttgg ggtggagttg acggatacgc ccactaccaa aggcttgccc       120
ctcgttgaca gtcccacacc catcgtcctc ggtgtttctg tatacttgac tattgtcatt       180
ggagggcttt tgtggataaa ggccagggat ctgaaaccgc gcgcctcgga gccatttttg       240
ctccaagctt tggtgcttgt gcacaacctg ttctgttttg cgctcagtct gtatatgtgc       300
gtgggcatcg cttatcaggc tattacctgg cggtactctc tctggggcaa tgcatacaat       360
cctaaacata aagagatggc gattctggta tacttgttct acatgtctaa gtacgtggaa       420
ttcatggata ccgttatcat gatactgaag cgcagcacca ggcaaataag cttcctccac       480
gtttatcatc attcttcaat ttccctcatt tggtgggcta ttgctcatca cgctcctggc       540
ggtgaagcat attggtctgc ggctctgaac tcaggagtgc atgttctcat gtatgcgtat       600
tacttcttgg ctgcctgcct tcgaagtagc ccaaagttaa aaaataagta cctttttttgg       660 ggcaggtact tgacacaatt ccaaatgttc cagtttatgc tgaacttagt gcaggcttac       720
tacgacatga aaacgaatgc gccatatcca caatggctga tcaagatttt gttctactac       780
atgatctcgt tgctgttttct tttcggcaat ttttacgtac aaaaatacat caaaccctct       840
gacggaaagc aaaagggagc taaaactgag tga                                    873

<210> SEQ ID NO 32
<211> LENGTH: 32
```

```
<212> TYPE: DNA
<213> ORGANISM: Artificial Sequence
<220> FEATURE:
<223> OTHER INFORMATION: Primer

<400> SEQUENCE: 32
gcggccgcgc catggaggtc gtggagagat tc                                32

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
gcggccgcgt cactcagttt tagctccc                                     28

<210> SEQ ID NO 34
<211> LENGTH: 903
<212> TYPE: DNA
<213> ORGANISM: Ostreococcus tauri

<400> SEQUENCE: 34
atgagcgcct ccggtgcgct gctgcccgcg atcgcgttcg ccgcgtacgc gtacgcgacg    60
tacgcctacg cctttgagtg gtcgcacgcg aatggcatcg acaacgtcga cgcgcgcgag   120
tggatcggtg cgctgtcgtt gaggctcccg gcgatcgcga cgacgatgta cctgttgttc   180
tgcctggtcg gaccgaggtt gatggcgaag cgcgaggcgt tcgacccgaa ggggttcatg   240
ctggcgtaca atgcgtatca gacggcgttc aacgtcgtcg tgctcgggat gttcgcgcga   300
gagatctcgg ggctggggca gcccgtgtgg gggtcaacca tgccgtggag cgatagaaaa   360
tcgtttaaga tcctcctcgg ggtgtggttg cactacaaca accaatattt ggagctattg   420
gacactgtgt tcatggttgc gcgcaagaag acgaagcagt tgagcttctt gcacgtttat   480
catcacgccc tgttgatctg gcgtggtgg ttggtgtgtc acttgatggc cacgaacgat   540
tgtatcgatg cctacttcgg cgcggcgtgc aactcgttca ttcacatcgt gatgtactcg   600
tattatctca tgtcggcgct cggcattcga tgcccgtgga agcgatacat cacccaggct   660
caaatgctcc aattcgtcat tgtcttcgcg cacgccgtgt tcgtgctgcg tcagaagcac   720
tgcccggtca cccttccttg ggcgcaaatg ttcgtcatga cgaacatgct cgtgctcttc   780
gggaacttct acctcaaggc gtactcgaac aagtcgcgcg gcgacggcgc gagttccgtg   840
aaaccagccg agaccacgcg cgcgcccagc gtgcgacgca cgcgatctcg aaaaattgac   900
taa                                                                903

<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
gcggccgcgc catgagcgcc tccggtgcgc tg                                32

<210> SEQ ID NO 36
<211> LENGTH: 23
<212> TYPE: DNA
<213> ORGANISM: Artificial Sequence
<220> FEATURE:
```

<223> OTHER INFORMATION: Primer

<400> SEQUENCE: 36
gcggccgcgt tagtcaattt ttc                                    23

<210> SEQ ID NO 37
<211> LENGTH: 1560
<212> TYPE: DNA
<213> ORGANISM: Thraustochytrium sp.

<400> SEQUENCE: 37

| atgacggtcg gctacgacga ggagatcccg ttcgagcagg tccgcgcgca caacaagccg | 60 |
| gatgacgcct ggtgcgcgat ccacgggcac gtgtacgatg tgaccaagtt cgcgagcgtg | 120 |
| cacccgggcg cgacattat cctgctggcc gcaggcaagg aggccaccgt gctgtacgag | 180 |
| acttaccatg tgcggggcgt ctcggacgcg gtgctgcgca gtaccgcat cggcaagctg | 240 |
| ccggacggcc aaggcggcgc gaacgagaag gaaaagcgga cgctctcggg cctctcgtcg | 300 |
| gcctcgtact acacgtggaa cagcgacttt tacagggtaa tgcgcgagcg cgtcgtggct | 360 |
| cggctcaagg agcgcggcaa ggcccgccgc ggaggctacg agctctggat caaggcgttc | 420 |
| ctgctgctcg tcggcttctg gagctcgctg tactggatgt gcacgctgga ccctcgttc | 480 |
| ggggccatcc tggccgccat gtcgctgggc gtctttgccg cctttgtggg cacgtgcatc | 540 |
| cagcacgacg gcaaccacgg cgcctttgcc cagtcgcgat gggtcaacaa ggttgccggg | 600 |
| tggacgctcg acatgatcgg cgccagcggc atgacgtggg agttccagca cgtcctgggc | 660 |
| caccatccgt acacgaacct gatcgaggag gagaacggcc tgcaaaaggt gagcggcaag | 720 |
| aagatggaca ccaagctggc cgaccaggag agcgatccgg acgtcttttc cacgtacccg | 780 |
| atgatgcgcc tgcacccgtg gcaccagaag cgctggtacc accgtttcca gcacatttac | 840 |
| ggccccttca tctttggctt catgaccatc aacaaggtgg tcacgcagga cgtcggtgtg | 900 |
| gtgctccgca gcggctctt ccagattgac gccgagtgcc ggtacgcgag cccaatgtac | 960 |
| gtggcgcgtt tctggatcat gaaggcgctc acggtgctct acatggtggc cctgccgtgc | 1020 |
| tacatgcagg gcccgtggca cggcctcaag ctgttcgcga tcgcgcactt tacgtgcggc | 1080 |
| gaggtgctcg caaccatgtt cattgtgaac cacatcatcg agggcgtctc gtacgcttcc | 1140 |
| aaggacgcgg tcaagggcac gatggcgccg ccgaagacga tgcacggcgt gacgcccatg | 1200 |
| aacaacacgc gcaaggaggt ggaggcggag gcgtccaagt ctggcgccgt ggtcaagtca | 1260 |
| gtcccgctcg acgactgggc cgccgtccag tgccagacct cggtgaactg gagcgtcggc | 1320 |
| tcgtggttct ggaatcactt ttccggcggc ctcaaccacc agattgagca ccacctgttc | 1380 |
| cccgggctca gccacgagac gtactaccac atccaggacg tcgttcagtc cacctgcgcc | 1440 |
| gagtacggcg tcccgtacca gcacgagcct tcgctctgga ccgcgtactg gaagatgctc | 1500 |
| gagcacctcc gtcagctcgg caatgaggag acccacgagt cctggcagcg cgctgcctga | 1560 |

<210> SEQ ID NO 38
<211> LENGTH: 32
<212> TYPE: DNA
<213> ORGANISM: Artificial Sequence
<220> FEATURE:
<223> OTHER INFORMATION: Primer

<400> SEQUENCE: 38
gcggccgcgc catgacggtc ggctacgacg ag                          32

```
<210> SEQ ID NO 39
<211> LENGTH: 29
<212> TYPE: DNA
<213> ORGANISM: Artificial Sequence
<220> FEATURE:
<223> OTHER INFORMATION: Primer

<400> SEQUENCE: 39
gcggccgcgt caggcagcgc gctgccagg                                    29

<210> SEQ ID NO 40
<211> LENGTH: 819
<212> TYPE: DNA
<213> ORGANISM: Thalassiosira pseudonana

<400> SEQUENCE: 40
atggacgcct acaacgctgc tatggacaag attggtgctg ctattattga ctggtctgat    60
cccgatggaa agttccgtgc cgatagagag gactggtggc tctgcgactt ccgtagcgcc   120
atcaccatcg ccctcatcta catcgccttc gtcatcctcg gttccgccgt catgcaatcc   180
ctccccgcaa tggatcccta ccccatcaaa ttcctctaca acgtctccca aatcttcctt   240
tgtgcctaca tgactgtcga ggcgggattt ttggcctacc gcaatggata taccgtcatg   300
ccttgcaatc atttcaatgt gaatgatcct cccgtggcga atcttctttg gttgttttat   360
atttccaagg tgtgggactt tgggatacc attttcattg tgttggggaa gaagtggcgt   420
caattatctt tcttgcatgt ataccatcac accaccatct ttctattcta ttggctgaat   480
gccaatgtct tgtacgatgg tgacatcttc cttaccatct tgctcaatgg attcatccac   540
acggtgatgt acacgtatta cttcatctgt atgcatacca aagattccaa gacgggcaag   600
agtcttccta tatggtggaa gtcgagtttg acggcgtttc agttgttgca attcactatc   660
atgatgagtc aggctaccta ccttgtcttc cacgggtgtg ataaggtgtc gcttcgtatc   720
acgattgtgt actttgtgta cattttgagt ttgttcttcc tttttgctca gttctttgtg   780
caatcataca tggcacccaa aaagaagaag agtgcttag                          819

<210> SEQ ID NO 41
<211> LENGTH: 1371
<212> TYPE: DNA
<213> ORGANISM: Ostreococcus tauri

<400> SEQUENCE: 41
atgtgcgtgg agacggaaaa taacgatggg atccccacgg tggagatcgc gttcgacggt    60
gagcgcgagc gggcggaggc aaacgtgaag ctgtccgcgg agaagatgga gccggcggcg   120
ctggcgaaga cgttcgcgag gcggtacgtc gtgatcgagg gggtggagta cgatgtgacg   180
gattttaagc acccgggagg aacggttatt ttctatgcgt tgtcaaacac cggggcggac   240
gcgacggaag cgttcaagga gtttcatcat cggtcgagaa aggcgaggaa agccttggcg   300
gcgctcccgt ctcgaccggc caagacggcc aaggtggacg acgcggagat gctccaagat   360
ttcgccaagt ggcggaaaga attggagaga gatggattct tcaagccctc tccggcgcac   420
gtggcgtatc gcttcgccga gctcgcggcg atgtacgctc tcgggacgta cctgatgtac   480
gctcgatacg tcgtctcctc ggtgctcgtg tacgcttgct ttttcggcgc ccgatgcggt   540
tgggtgcagc acgagggcgg acacagctcg ctgacgggca catttggtg ggacaagcgc   600 atccaggcct tcacgccggt tcggtctc gccggtagcg cgacatgtg gaactcgatg   660 cacaacaagc atcacgcgac gcctcaaaag gttcgtcacg acatggatct ggacaccacc   720
```

-continued

```
cccgcggtgg cgttcttcaa caccgcggtg gaagacaatc gtccccgtgg ctttagcaag    780
tactggttgc gccttcaggc gtggaccttc atccccgtga cgtccggctt ggtgctcctt    840
ttctggatgt ttttcctcca cccctccaag gctttgaagg gtggcaagta cgaagagttg    900
gtgtggatgc tcgccgcgca cgtcatccgc acgtggacga tcaaggcggt gaccggattc    960
accgcgatgc agtcctacgg cttattttg gcgacgagct gggtgagcgg ctgctatctg   1020
tttgcacact tctccacgtc gcacacgcac ctggatgtgg tgcccgcgga cgagcatctc   1080
tcctgggttc gatacgccgt cgatcacacg atcgacatcg atccgagtca aggttgggtg   1140
aactggttga tgggctacct caactgccaa gtcatccacc acctctttcc gagcatgccg   1200
cagttccgcc agcccgaggt atctcgccgc ttcgtcgcct ttgcgaaaaa gtggaacctc   1260
aactacaagg tcatgaccta cgccggtgcg tggaaggcaa cgctcggaaa cctcgacaac   1320
gtgggtaagc actactacgt gcacggccaa cactccggaa agacggcgta a            1371
```

<210> SEQ ID NO 42
<211> LENGTH: 26
<212> TYPE: DNA
<213> ORGANISM: Artificial Sequence
<220> FEATURE:
<223> OTHER INFORMATION: Degenerate Primer
<220> FEATURE:
<221> NAME/KEY: modified_base
<222> LOCATION: (6)..(6)
<223> OTHER INFORMATION: I
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is a, c, g, or t

<400> SEQUENCE: 42
tgggtnytbg cncaygartg ygghca                                           26

<210> SEQ ID NO 43
<211> LENGTH: 26
<212> TYPE: DNA
<213> ORGANISM: Artificial Sequence
<220> FEATURE:
<223> OTHER INFORMATION: Degenerate Primer
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (24)..(24)
<223> OTHER INFORMATION: I
<220> FEATURE:
<221> NAME/KEY: misc_feature
<222> LOCATION: (24)..(24)
<223> OTHER INFORMATION: n is a, c, g, or t

<400> SEQUENCE: 43
ttnggrtcng trtgytgvar raangt                                          26

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
atgaagacca tgtcgcgctc catgt                                           25

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
gacgagcacc tcatcctgct tag                                             23

<210> SEQ ID NO 46
<211> LENGTH: 51
<212> TYPE: PRT
<213> ORGANISM: Artificial Sequence
<220> FEATURE:
<223> OTHER INFORMATION: Desaturase motif 1
<220> FEATURE:
<221> NAME/KEY: VARIANT
<222> LOCATION: (1)..(48)
<223> OTHER INFORMATION: Xaa is any amino acid
<220> FEATURE:
<221> NAME/KEY: VARIANT
<222> LOCATION: (1)..(48)
<223> OTHER INFORMATION: Xaa is any amino acid
<220> FEATURE:
<221> NAME/KEY: misc_feature
<222> LOCATION: (49)..(50)
<223> OTHER INFORMATION: Xaa can be any naturally occurring amino acid

<400> SEQUENCE: 46

Gly Xaa Xaa Xaa Xaa Xaa Xaa Xaa Xaa Xaa His Xaa Xaa Xaa His
1               5                   10                  15

Xaa Xaa Xaa Xaa Xaa Xaa Xaa Xaa Xaa Xaa Xaa Xaa Gly Xaa Xaa
            20                  25                  30

Xaa Xaa Xaa Xaa Xaa Xaa Xaa Pro Xaa Xaa Xaa Trp Xaa Xaa Xaa His
        35                  40                  45

Xaa Xaa His
    50

<210> SEQ ID NO 47
<211> LENGTH: 17
<212> TYPE: PRT
<213> ORGANISM: Artificial Sequence
<220> FEATURE:
<223> OTHER INFORMATION: Desaturase motif 2
<220> FEATURE:
<221> NAME/KEY: VARIANT
<222> LOCATION: (1)..(15)
<223> OTHER INFORMATION: Xaa is any amino acid
<220> FEATURE:
<221> NAME/KEY: VARIANT
<222> LOCATION: (16)..(16)

<223> OTHER INFORMATION: Xaa is Gln or His

<400> SEQUENCE: 47

Pro Xaa Xaa Xaa Xaa Xaa Xaa Xaa Xaa Xaa Xaa Xaa Xaa Xaa Xaa
1               5                   10                  15

His

<210> SEQ ID NO 48
<211> LENGTH: 13
<212> TYPE: PRT
<213> ORGANISM: Artificial Sequence
<220> FEATURE:
<223> OTHER INFORMATION: Desaturase motif 3
<220> FEATURE:
<221> NAME/KEY: VARIANT
<222> LOCATION: (1)..(13)
<223> OTHER INFORMATION: Xaa is any amino acid

<400> SEQUENCE: 48

His Xaa Xaa His His Xaa Xaa Xaa Xaa Xaa Pro Xaa Tyr
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Desaturase motif 4
<220> FEATURE:
<221> NAME/KEY: VARIANT
<222> LOCATION: (1)..(14)
<223> OTHER INFORMATION: Xaa is any amino acid

<400> SEQUENCE: 49

His Xaa Xaa His His Xaa Xaa Xaa Xaa Xaa Xaa Pro Xaa Tyr
1               5                   10

<210> SEQ ID NO 50
<211> LENGTH: 1300
<212> TYPE: DNA
<213> ORGANISM: Hyaloperonospora parasitica

<400> SEQUENCE: 50
agtagtgatc ttgtcgccac gcgtcccgca ccaagtctca cgtaacacca tttcggaact      60
tgctccgtca gccacaaaaa cgtccatggc gaccaagcaa tcggtcgcgt tcccgaccct     120
cacggacctc aagcggtcgc tcccaagcga gtgcttcgaa tcctcattgc cgctgtcact     180
ctactacacg ctgcgctcgc tcgtgtttgc cggttccttg gctgtaagtc tcagctacgc     240
gctcgcccag ccactcgtcc agaacttcta cccgctccgt gtcgctctaa tcgcgggcta     300
caccgtgttc cagggcgtga tcttctgggg ctttttcacc atcggtcatg atgccggtca     360
cggcgctttc agccgctacc cggtgctcaa cttcaccgtc gggacgctca tgcactcgct     420
catcctcacg ccgttcgagt cgtggaaact cacgcaccgc caccaccaca agaacacggg     480
caacatcgac cgagacgaga tcttttaccc ccaacgggag agcgacgacc acccagtttc     540
tcgccatttg accttcacgc tcggagctgc gtggttcgcc tacctcgtcg aggggtttcc     600
acctcggaaa ctcaatcact ataacccgtt cgagccgctc tttgaacgga gagtatctgc     660
tgttatcatc tcaattctcg cccagttttt cgtcgcggga ctctcgatct acctctgctt     720
tcaagtggga gtccaggctg tggcgctcta ttactacgga ccgatctttg tctttggcac     780
gatgctcgtc atcacgacgt ttttgcacca caatgacgag gagacgccgt ggtatggaga     840

```
cgaggactgg tcgtacgtca agggcaacct ctcgtcggtt gatcggtcat acggaccgct    900
cattgataac ttgagccaca acattggcac gcaccaggtc catcacctgt tccccattat    960
tccccactac aagctcaagc ccgcgacagc tgcttttcgt cgtgcttttc ctcacctcgt   1020
acgcaagagt gacgagcgga ttcttcaggc gttttaccgc atcggtcggc tctatgcaaa   1080
gtacggcgtc gccgactcgt cagccaagct gtttacactc aaggaagccc aattgacgtc   1140
gaaagcagca agtgatgcca agcagctta ggattagcgc tggaagcagt tctcactcat   1200
gcaagacagg ctcacaaaaa cgaacgatgg acggatggat gtggcaagtg atctattgac   1260
agatgaacgg tctacgtcac ttctactcta gtctaacgaa                         1300
```

```
<210> SEQ ID NO 51
<211> LENGTH: 1086
<212> TYPE: DNA
<213> ORGANISM: Hyaloperonospora parasitica

<400> SEQUENCE: 51
atggcgacca agcaatcggt cgcgttcccg accctcacgg acctcaagcg gtcgctccca     60
agcgagtgct tcgaatcctc attgccgctg tcactctact acacgctgcg ctcgctcgtg    120
tttgccggtt ccttggctgt aagtctcagc tacgcgctcg cccagccact cgtccagaac    180
ttctacccgc tccgtgtcgc tctaatcgcg ggctacaccg tgttccaggg cgtgatcttc    240
tggggctttt tcaccatcgg tcatgatgcc ggtcacggcg ctttcagccg ctacccggtg    300
ctcaacttca ccgtcgggac gctcatgcac tcgctcatcc tcacgccgtt cgagtcgtgg    360
aaactcacgc accgccacca ccacaagaac acgggcaaca tcgaccgaga cgagatcttt    420 taccccccaac gggagagcga cgaccaccca gtttctcgcc atttgacctt cacgctcgga    480
gctgcgtggt cgcctacct cgtcgagggg tttccacctc ggaaactcaa tcactataac    540
ccgttcgagc cgctctttga acggagagta tctgctgtta tcatctcaat tctcgcccag    600
tttttcgtcg cgggactctc gatctacctc tgctttcaag tgggagtcca ggctgtggcg    660
ctctattact acggaccgat ctttgtcttt ggcacgatgc tcgtcatcac gacgtttttg    720
caccacaatg acgaggagac gccgtggtat ggagacgagg actggtcgta cgtcaagggc    780
aacctctcgt cggttgatcg gtcatacgga ccgctcattg ataacttgag ccacaacatt    840
ggcacgcacc aggtccatca cctgttcccc attattcccc actacaagct caagcccgcg    900
acagctgctt ttcgtcgtgc ttttcctcac ctcgtacgca agagtgacga gcggattctt    960
caggcgtttt accgcatcgg tcggctctat gcaaagtacg gcgtcgccga ctcgtcagcc   1020 aagctgtttta cactcaagga agcccaattg acgtcgaaag cagcaagtga tgccaaagca   1080
gcttag                                                              1086
```

```
<210> SEQ ID NO 52
<211> LENGTH: 361
<212> TYPE: PRT
<213> ORGANISM: Hyaloperonospora parasitica

<400> SEQUENCE: 52

Met Ala Thr Lys Gln Ser Val Ala Phe Pro Thr Leu Thr Asp Leu Lys
1               5                   10                  15

Arg Ser Leu Pro Ser Glu Cys Phe Glu Ser Ser Leu Pro Leu Ser Leu
                20                  25                  30

Tyr Tyr Thr Leu Arg Ser Leu Val Phe Ala Gly Ser Leu Ala Val Ser
            35                  40                  45
```

```
Leu Ser Tyr Ala Leu Ala Gln Pro Leu Val Gln Asn Phe Tyr Pro Leu
    50                  55                  60

Arg Val Ala Leu Ile Ala Gly Tyr Thr Val Phe Gln Gly Val Ile Phe
 65                  70                  75                  80

Trp Gly Phe Phe Thr Ile Gly His Asp Ala Gly His Gly Ala Phe Ser
                 85                  90                  95

Arg Tyr Pro Val Leu Asn Phe Thr Val Gly Thr Leu Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
130                 135                 140

Glu Ser Asp Asp His Pro Val Ser Arg His Leu Thr Phe Thr Leu Gly
145                 150                 155                 160

Ala Ala Trp Phe Ala Tyr Leu Val Glu Gly Phe Pro Pro Arg Lys Leu
                165                 170                 175

Asn His Tyr Asn Pro Phe Glu Pro Leu Phe Glu Arg Arg Val Ser Ala
            180                 185                 190

Val Ile Ile Ser Ile Leu Ala Gln Phe Phe Val Ala Gly Leu Ser Ile
        195                 200                 205

Tyr Leu Cys Phe Gln Val Gly Val Gln Ala Val Ala Leu Tyr Tyr Tyr
    210                 215                 220

Gly Pro Ile Phe Val Phe Gly Thr Met Leu Val Ile Thr Thr Phe Leu
225                 230                 235                 240

His His Asn Asp Glu Glu Thr Pro Trp Tyr Gly Asp Glu Asp Trp Ser
                245                 250                 255

Tyr Val Lys Gly Asn Leu Ser Ser Val Asp Arg Ser Tyr Gly Pro Leu
            260                 265                 270

Ile Asp Asn Leu Ser His Asn Ile Gly Thr His Gln Val His His Leu
        275                 280                 285

Phe Pro Ile Ile Pro His Tyr Lys Leu Lys Pro Ala Thr Ala Ala Phe
    290                 295                 300

Arg Arg Ala Phe Pro His Leu Val Arg Lys Ser Asp Glu Arg Ile Leu
305                 310                 315                 320

Gln Ala Phe Tyr Arg Ile Gly Arg Leu Tyr Ala Lys Tyr Gly Val Ala
                325                 330                 335

Asp Ser Ser Ala Lys Leu Phe Thr Leu Lys Glu Ala Gln Leu Thr Ser
            340                 345                 350

Lys Ala Ala Ser Asp Ala Lys Ala Ala
        355                 360

<210> SEQ ID NO 53
<211> LENGTH: 19
<212> TYPE: DNA
<213> ORGANISM: Artificial Sequence
<220> FEATURE:
<223> OTHER INFORMATION: Primer

<400> SEQUENCE: 53
atggcgacca agcaatcgg                                              19

<210> SEQ ID NO 54
<211> LENGTH: 30
<212> TYPE: DNA
<213> ORGANISM: Artificial Sequence
<220> FEATURE:
<223> OTHER INFORMATION: Primer
```

-continued

```
<400> SEQUENCE: 54
gcggccgcgc catggcgacc aagcaatcgg                              30

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
ctaagctgct ttggcatcac                                         20

<210> SEQ ID NO 56
<211> LENGTH: 29
<212> TYPE: DNA
<213> ORGANISM: Artificial Sequence
<220> FEATURE:
<223> OTHER INFORMATION: Primer

<400> SEQUENCE: 56
gcggccgcgc taagctgctt tggcatcac                               29
```

DESATURASES AND PROCESS FOR THE PRODUCTION OF POLYUNSATURATED FATTY ACIDS IN TRANSGENIC ORGANISMS

RELATED APPLICATIONS

This application is a national stage application (under 35 U.S.C. §371) of PCT/EP2009/066569, filed Dec. 8, 2009, which claims benefit of European application 08171520.3, filed Dec. 12, 2008 and European application 09151937.1, filed Feb. 3, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_17418_00069_US. The size of the text file is 51 KB, and the text file was created on Jun. 7, 2011.

The present invention relates to polynucleotides from *Cochliobolus heterostrophus* C5, *Cyanothece* sp. CCY0110, *Mycocentrospora acerina* and *Hyaloperonospora parasitica*, which code for desaturases and which can be employed for the recombinant production of polyunsaturated fatty acids. The invention furthermore relates to vectors, host cells and transgenic nonhuman organisms which comprise the polynucleotides according to the invention, and to the polypeptides encoded by the polynucleotides. The invention furthermore relates to antibodies against the polypeptides according to the invention. Finally, the invention also relates to production processes for the polyunsaturated fatty acids and for oil, lipid and fatty acid compositions and to their use as drugs, cosmetics, foodstuffs, feedstuffs, preferably fish food, or food supplements.

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter themselves. Polyunsaturated ω3-fatty acids and ω6-fatty acids are therefore an important constituent in animal and human nutrition.

Polyunsaturated long-chain ω3-fatty acids such as eicosapentaenoic acid (=EPA, C20:5$^{\Delta 5,8,11,14,17}$) or docosahexaenoic acid (=DHA, C22:6$^{\Delta 4,7,10,13,16,19}$) are important components in human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids.

ω3-fatty acids, which are preferentially found in fish oils, to the food is particularly important. Thus, for example, polyunsaturated fatty acids such as docosahexaenoic acid (=DHA, C22:6$^{\Delta 4,7,10,13,16,19}$) or eicosapentaenoic acid (=EPA, C20:5$^{\Delta 5,8,11,14,17}$) are added to infant formula to improve the nutritional value. The unsaturated fatty acid DHA is said to have a positive effect on the development and maintenance of brain functions.

Hereinbelow, polyunsaturated fatty acids are referred to as PUFA, PUFAs, LCPUFA or LCPUFAs (polyunsaturated fatty acids, PUFA, long-chain polyunsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and other organisms, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as DHA, EPA, arachidonic acid (=ARA, C20:4$^{\Delta 5,8,11,14}$) dihomo-γ-linolenic acid (C20:3$^{\Delta 8,11,14}$) or docosapentaenoic acid (DPA, C22:5$^{\Delta 7,10,13,16,19}$) are not synthesized in oil crops such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω3-fatty acids are said to have a positive effect on the cholesterol level in the blood and thus on the possibility of preventing heart disease. The risk of heart disease, a stroke or hypertension can be reduced markedly by adding these ω3-fatty acids to food. Also, ω3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids which are formed from ω6-fatty acids (known as the PG$_2$ series) generally promote inflammatory reactions, while eicosanoids from ω3-fatty acids (known as the PG$_3$ series) have little or no proinflammatory effect.

Owing to their positive characteristics, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, WO 96/21022, WO 00/21557 and WO 99/27111. Their application for production in transgenic organisms is described, for example, in WO 98/46763, WO 98/46764 and WO 98/46765. In this context, the expression of various desaturases and the formation of polyunsaturated fatty acids is also described and claimed; see, for example, WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are microalgae such as *Phaeodactylum tricornutum*, *Porphiridium* species, *Thraustochytrium* species, *Schizochytrium* species or *Crypthecodinium* species, ciliates such as *Stylonychia* or *Colpidium*, fungae such as *Mortierella*, *Entomophthora* or *Mucor* and/or mosses such as *Physcomitrella*, preferably *Physcomitrella patens*, *Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible. However, only limited amounts of the desired polyunsaturated fatty acids such as DPA, EPA or ARA can be produced with the aid of the abovementioned microorganisms. Moreover, depending on the microorganism used, these are generally generated as fatty acid mixtures of, for example, EPA, DPA and ARA.

A variety of synthetic pathways is being discussed for the synthesis of arachidonic acid, eicosapentaenoic acid (EPA) and docosahexaenoic acid (DHA). Thus, EPA or DHA are produced in marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of the pathway described in Zank et al. and in Sakuradani et al. via Δ6-desaturase, Δ6-elongase, Δ5-desaturase, Δ5-elongase and Δ4-desaturase is the Sprecher synthesis pathway (Sprecher 2000, Biochim. Biophys. Acta 1486: 219-231) in mammals. Instead of the Δ4-desaturation, a further elongation step is effected here to give $C_{24}$, followed by a further Δ6-desaturation and finally β-oxidation to give the $C_{22}$ chain length. What is known as the Sprecher synthesis pathway is, however, not suitable for the production in plants and microorganisms since the regulatory mechanisms are not yet known.

Depending on their desaturation pattern, the polyunsaturated fatty acids can be divided into two large classes, viz. ω6- or ω3-fatty acids, which differ with regard to their metabolic and functional activities. The starting material for the ω6-metabolic pathway is the fatty acid linoleic acid (18:$2^{\Delta 9,12}$), while the ω3-pathway proceeds via linolenic acid (18:$3^{\Delta 9,12,15}$). Linolenic acid is formed by the activity of a Δ15-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and Δ15-desaturase) and must take up these fatty acids (essential fatty acids) via food. Starting with these precursors, the physiologically important polyunsaturated fatty acids arachidonic acid (=ARA, 20:$4^{\Delta 5,8,11,14}$) an ω6-fatty acid, and the two ω3-fatty acids eicosapentaenoic acid (=EPA, 20:$5^{\Delta 5,8,11,14,17}$) and docosahexaenoic acid (DHA, 22:$6^{\Delta 4,7,10,13,17,19}$) are synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

Higher plants comprise polyunsaturated fatty acids such as linoleic acid (C18:2) and linolenic acid (C18:3). ARA, EPA and DHA are not found at all in the seed oil of higher plants, or only in miniscule amounts (E. Ucciani: Nouveau Dictionnaire des Huiles Vegetales [New Dictionary of Vegetable Oils]. Technique & Documentation—Lavoisier, 1995. ISBN: 2-7430-0009-0). However, the production of LCPUFAs in higher plants (preferably in oil crops such as oilseed rape, linseed, sunflower and soybeans) would be advantageous since large amounts of high-quality LCPUFAs for the food industry, animal nutrition and pharmaceutical purposes might be obtained economically. A potential route is via recombinant methods, where genes which code for enzymes of the biosynthesis of LCPUFAs are introduced and expressed into oil crops. These genes code for, for example, Δ6-desaturases, Δ6-elongases, Δ5-desaturases or Δ4-desaturases. These genes can advantageously be isolated from microorganisms and lower plants which produce LCPUFAs and incorporate them in the membranes or triacylglycerides. Thus, it has already been possible to isolate Δ6-desaturase genes from the moss *Physcomitrella patens* and Δ6-elongase genes from *P. patens* and from the nematode *C. elegans*. (Zank, T. K. et al. Plant Journal 31:255-268, 2002, Beaudoin et al. Biochem Soc Trans 28:661-663, 2000).

The first transgenic plants which comprise and express genes coding for LCPUFA biosynthesis enzymes and which produce LCPUFAs were described for example, in DE-A-102 19 203 (process for the production of polyunsaturated fatty acids in plants). However, these plants produce LCPUFAs in amounts which require further optimization for processing the oils which are present in the plants.

To ensure the enrichment of food and of feed with these polyunsaturated fatty acids, there is therefore a great need for means and measures for a simple, inexpensive process for the production of these polyunsaturated fatty acids, specifically in eukaryotic systems.

The object on which the present invention is based is the provision of such means and measures. This object is achieved by the embodiments which are described in the patent claims and hereinbelow.

The present invention thus relates to a polynucleotide comprising a nucleic acid sequence selected from the group consisting of:

(a) nucleic acid sequence as shown in any of SEQ ID No. 1, 2, 8, 9, 15, 16, 50 or 51;

(b) nucleic acid sequence which codes for a polypeptide which features an amino acid sequence as shown in any of SEQ ID No. 3, 10, 17 or 52;

(c) nucleic acid sequence which has at least 70% identity to one of the nucleic acid sequences of (a) or (b), and which codes for a polypeptide with a desaturase activity; and (d) nucleic acid sequence for a fragment of a nucleic acid of (a), (b) or (c), wherein the fragment codes for a polypeptide with a desaturase activity.

The class of the ω6-fatty acids is based on the ω6-fatty acid linoleic acid (18:2Δ9,12), while the class of the ω3-fatty acids is based on the (3-fatty acid linolenic acid (18:3(9,12,15); see FIG. 1. These two fatty acids are the substrates for the synthesis of long-chain (6- and (3-PUFAs, respectively. The increase of the content in these fatty acids according to the genes which are introduced leads to an increase of the content in long-chain-PUFAs.

The present invention provides polynucleotide sequences which lead to an increase of the substrates 18:2(9,12 and 18:3(9,12,15, respectively. There have been identified polynucleotide sequences which code for enzymes with (12-desaturase activity, with (12- and (15-desaturase activity, with (15-desaturase activity or with (3-desaturase activity.

According to the invention, the term "polynucleotide" refers to polynucleotides which comprise nucleic acid sequences which code for polypeptides with desaturase activity. The desaturase activities are preferably required for the biosynthesis of lipids or fatty acids. Especially preferably, they take the form of the following desaturase activities: Δ12-desaturase, Δ15-desaturase, Δ12- and Δ15-desaturase or omega-3-desaturase activity. The desaturases are preferably involved in the synthesis of polyunsaturated fatty acids (PUFAs) and especially preferably in the synthesis of long-chain PUFAs (LCPUFAs). Suitable detection systems for these desaturase activities are described in the examples or in WO 2005/083053. The desaturase activities according to the invention especially preferably have substrate specificities and/or conversion rates which are comparable to those of the respective homologous desaturase enzymes from *Pythium irregulare, Ostreococcus tauri, Phytophtora sojae* or *Phytophtora* infestans. The specific polynucleotides according to the invention, i.e. the polynucleotides with a nucleic acid sequence as shown in SEQ ID No.: 1, 2, 8, 9, 15, 16, 50 or 51 have been obtained from *Cochliobolus heterostrophus* C5, *Cyanothece* sp. CCY0110, *Polaromonas* sp. JS666, *Prochlorococcus marinus* str. MIT 9313, *Synechococcus* sp. PCC 7335, *Mycocentrospora acerina* or *Hyaloperonospora parasitica*.

In particular, the nucleic acid sequences according to SEQ ID No. 1 and 2 originate from *Cochliobolus heterostrophus* C5, the nucleic acid sequences according to SEQ ID No. 8 and 9 from *Cyanothece* sp. CCY0110, the nucleic acid sequences according to SEQ ID No. 15 and 16 from *Mycocentrospora acerina* and the nucleic acid sequences according to SEQ ID No. 50 and 51 from *Hyaloperonospora parasitica*. SEQ ID No. 1, 8 and 50 are genomic sequences, SEQ ID No. 15 is an mRNA transcript, while SEQ ID No. 2, 9, 16 and 51 are coding sequences (cds). SEQ ID No. 3, 10, 17 and 52 show the corresponding amino acid sequences.

Thus, polynucleotides according to the invention are especially preferred:

Polynucleotides which code for a polypeptide with Δ15-desaturase activity and which comprise (i) a nucleic acid sequence as shown in SEQ ID No. 1 or 2, (ii) a nucleic acid sequence which codes for a polypeptide as shown in SEQ ID No. 3, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ15-desaturase activity and which comprise (i) a nucleic acid sequence as shown in SEQ ID No. 8 or 9, (ii) a nucleic acid sequence which codes for a polypeptide as shown in SEQ ID No. 10, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ15-desaturase activity.

Polynucleotides which code for a polypeptide with Δ12-desaturase activity and which comprise (i) a nucleic acid sequence as shown in SEQ ID No. 15 or 16, (ii) a nucleic acid sequence which codes for a polypeptide as shown in SEQ ID No. 17, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a Δ12-desaturase activity.

Polynucleotides which code for a polypeptide with ω3-desaturase activity and which comprise (i) a nucleic acid sequence as shown in SEQ ID No. 50 or 51, (ii) a nucleic acid sequence which codes for a polypeptide as shown in SEQ ID No. 52, (iii) a nucleic acid sequence which has at least 70% identity to one of the nucleic acid sequences of (i) or (ii), or (iv) a nucleic acid sequence for a fragment of a nucleic acid of (i), (ii) or (iii), where the fragment codes for a polypeptide with a ω3-desaturase activity.

The term "delta-12-desaturase (or Δ-12-desaturase or d-12-desaturase or d12-Des or d12Des)" or "delta-12-desaturase (or Δ-12-desaturase or d-12-desaturase or d12-Des or d12Des) activity" as used in the present context refers to an enzyme with the enzymatic function for dehydrogenating C18-fatty acids which are already dehydrogenated on the C atom 9-10. Here, the C atoms C12 and C13 are dehydrogenated in each case one hydrogen atom, giving rise to a double bond between these two C atoms.

The term "delta-15-desaturase (or Δ-15-desaturase or d-15-desaturase or d15-Des or d15Des)" or "delta-15-desaturase (or Δ-15-desaturase or d-15-desaturase or d15-Des or d15Des) activity" as used in the present context refers to an enzyme with the enzymatic function for dehydrogenating C18- and/or C20-fatty acids which are dehydrogenated on the C atoms 6-7, 8-9, 9-10, 12-13 and/or 13-14. Here, the C atoms C15-16 and/or C17-18 are dehydrogenated in each case one hydrogen atom, giving rise to a double bond between the two C atoms.

The term "delta-12- and delta-15-desaturase (or Δ-12- and Δ-15-desaturase or as written hereinabove)" or "delta-12- and delta-15-desaturase (or Δ-12- and Δ-15-desaturase or as written hereinabove) activity" as used in the present context refers to an enzyme with the enzymatic function for dehydrogenating C18- and/or C20-fatty acids which are dehydrogenated on the C atoms 6-7, 8-9, 9-10 and/or 13-14. Here, the C atoms C12-13 and C15-16 and/or C17-18 are dehydrogenated in each case one hydrogen atom, giving rise to a double bond between the two C atoms.

The term "omega-3-desaturase (or (3-desaturase or (3-Des or (3Des or omega3 Des or o3Des)" or "omega-3-desaturase (or (3-desaturase or (3-Des or (3Des or omega3 Des or o3Des) activity" as used in the present context refers to an enzyme with the enzymatic function for the dehydrogenation of C18-, C20- and/or C22-fatty acids which are dehydrogenated on the C atoms 4-5, 5-6, 6-7, 8-9, 9-10, 13-14 and/or 16-17. Here, the C atoms C15-16 and/or C17-18 and/or C19-20 are dehydrogenated by in each case one hydrogen atom, giving rise to a double bond between the two C atoms.

Desaturases according to the invention especially preferably feature, in succession, the desaturase motif 1 "GX10HX3HX13GX9PX3WX3H" (SEQ ID No. 46), the desaturase motif 2 "PX14(H/Q)H" (SEQ ID No. 47) and either the desaturase motif 3 "HX2HHX5PXY" (SEQ ID No. 48) or the desaturase motif 4 "HX2HHX6PXY" (SEQ ID No. 49), where X stands for any amino acid. Whether it is a Δ12-, Δ15- or omega3-desaturase can be deduced from the amino acid at the variable position 16 of the desaturase motif 2 (H or Q): Q=glutamine is indicative of putative Δ12-desaturases, H=histidine is indicative of Δ15- or omega3-desaturases.

In this context, the polynucleotide sequences or the peptide sequences according to the invention preferably originate from the abovementioned organisms.

It is clear that, in the light of the degeneracy of the genetic code, the abovementioned specific sequences can also be modified, where the modified polynucleotides still code for polypeptides with an amino acid sequence as shown in any of SEQ ID No. 3, 10, 17 or 52 and which have the abovementioned desaturase activities.

The term "polynucleotide" also comprises variants of the abovementioned specific polynucleotides. These may take the form of homologous, orthologous or paralogous sequences. Such variants comprise nucleic acid sequences which feature at least one base substitution, one base addition or one base deletion, it being intended that the variants still code for a polypeptide with the abovementioned biological activity of the respective starting sequence. Variants comprise polynucleotides which are capable of hybridization with the abovementioned polynucleotides, preferably under stringent conditions. Especially preferred stringent conditions are known to the skilled worker and can be found in Current Protocols in Molecular Biology, John Wiley & Sons, N.Y. (1989), 6.3.1-6.3.6. A preferred example of stringent hybridization conditions are hybridizations in 6× sodium chloride/sodium citrate (=SSC) at approximately 45° C., preferably 50° C., 55° C., 60° C. and most preferably at 62° C., followed by one or more wash steps in 0.1×SSC, 0.1% SDS at 50 to 65° C., preferably 55 to 65° C. even more preferably at 60 to 65° C. The skilled worker knows that these hybridization conditions differ as a function of the type of nucleic acid and, for example when organic solvents are present, with regard to the temperature and the buffer concentration. Under "standard hybridization conditions", the temperature differs as a function of the type of nucleic acid between 42° C. and 58° C. in aqueous buffer with a concentration of from 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably for example 0.1×SSC and 30° C. to 55° C., preferably between 45° C. and 55° C. The abovementioned hybridization temperatures are determined for example for a nucleic acid of approximately 100 bp (=base pairs) in length and a G+C content of 50% in the absence of formamide. The skilled worker knows how to determine the hybridization conditions required with the aid of textbooks, such as the one mentioned hereinabove, or from the following textbooks: Sambrook et al., "Molecular Cloning", Cold Spring Harbor Laboratory, 1989; Hames and Higgins (eds.) 1985, "Nucleic Acids Hybridization: A Practical Approach", IRL Press at Oxford University Press, Oxford; Brown (ed.) 1991, "Essential Molecular Biology: A Practical Approach", IRL Press at Oxford University Press, Oxford. As an alternative, variants of the specific polynucleotides according to the invention may also be provided by polymerase chain reaction (PCR)-based methods. To this end, it is possible first to derive primers from conserved sequences (for example sequences which code for functional domains in the polypeptide). Conserved sequences can be determined by sequence comparisons with polynucleotides which code for polypeptides with a similar activity. The template used may be DNA or cDNA from bacteria, fungi, plants or animals. DNA fragments obtained by PCR can be used for screening suitable genomic libraries or cDNA libraries in order to—if required—isolate the complete open reading frame of the polynucleotide and to determine it by sequencing. Preferred variants comprise polynucleotides which comprise a nucleic acid sequence with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% (or a different percentage than mentioned herein) identity with one of the abovementioned specific nucleic acid sequences and codes for a polypeptide with the respective biological activity. Equally preferably comprised are polynucleotides which comprise nucleic acid sequences which code for a polypeptide with an amino acid sequence with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% (or a different percentage than mentioned herein) identity with one of the abovementioned specific amino acid sequences and where the polypeptide has the respective biological activity of the starting sequence.

The percentage of identical nucleotides or amino acids preferably relates to a sequence segment of at least 50% of the sequences to be compared, and especially preferably over the entire length of the sequences to be compared. A multiplicity of programs which implement algorithms for such comparisons are described in the prior art and commercially available. In particular, reference may be made to the algorithms of Needleman and Wunsch or Smith and Waterman, which give particularly reliable results. These algorithms can preferably be implemented by the following programs: PileUp (J. Mol. Evolution., 25, 351-360, 1987, Higgins 1989, CABIOS, 5: 151-153), Gap and BestFit (Needleman and Wunsch (J. Mol. Biol. 48; 443-453 (1970) and Smith and Waterman (Adv. Appl. Math. 2; 482-489 (1981))), as part of the GCG software (Genetics Computer Group, 575 Science Drive, Madison, Wis., USA 53711, 1991). For the purposes of the present invention, it is especially preferred to determine the percentage (%) of the sequence identity with the GAP program over the entire sequence, with the following set parameters: Gap Weight: 50, Length Weight: 3, Average Match: 10.000 and Average Mismatch: 0.000.

A polynucleotide which only comprises a fragment of the abovementioned nucleic acid sequences is also a polynucleotide according to the invention. Here, it is intended that the fragment codes for a polypeptide which features the biological activity of the starting sequence, or of the polypeptide which the latter codes for. Polypeptides which are encoded by such polynucleotides therefore comprise, or consist of, domains of the abovementioned specific polypeptides (starting polypeptides) which confer the biological activity. A fragment for the purposes of the invention preferably comprises at least 50, at least 100, at least 250 or at least 500 consecutive nucleotides of the abovementioned specific sequences or codes for an amino acid sequence comprising at least 20, at least 30, at least 50, at least 80, at least 100 or at least 150 consecutive amino acids of one of the abovementioned specific amino acid sequences, and confers biological activity, preferably desaturase activity, as described above.

The polynucleotide variants according to the invention preferably feature at least 10%, at least 20%, at least 30%, at least 40%, at least 50%, at least 60%, at least 70%, at least 80% or at least 90% of the respective biological activity of the polypeptide which is encoded by the starting sequence. That is to say the polypeptides which are encoded by the polynucleotides according to the invention can participate in the metabolism of compounds required for the synthesis of fatty acids, fatty acid esters such as diacylglycerides and/or triacylglycerides in an organism, preferably in a plant or plant cell, or can participate in the transport of molecules across membranes, which means $C_{18}$-, $C_{20}$- or $C_{22}$-carbon chains in the fatty acid molecule with double bonds at least two, advantageously three, four, five or six positions.

The polynucleotides according to the invention either comprise the abovementioned specific nucleic acid sequences or consist of them. That is to say, that the polynucleotides according to the invention may, in principle, also comprise further nucleotides. These may preferably be 3'- or 5'-untranslated regions of the genomic nucleic acid sequence. They preferably consist of at least 100, 200 or 500 nucleotides at the 5' terminus and of at least 20, 50 or 100 nucleotides at the 3' terminus of the coding region. Further polynucleotides which comprise additional nucleic acid sequences are those which code for fusion proteins. Such fusion proteins can code for further polypeptides or polypeptide portions, in addition to the abovementioned polypeptides. The additional polypeptide or polypeptide portion may take the form of further enzymes of lipid or fatty acid biosynthesis. Others which are feasible are polypeptides which may act as expression markers (green, yellow, red, blue fluorescent proteins, alkaline phosphatase and others) or so-called "tags" as labels or as an aid for purification (for example FLAG tags, 6-histidine tags, MYC tags and others).

Polynucleotide variants can be isolated from different natural or artificial sources. For example, they can be generated artificially by in-vitro or in-vivo mutagenesis. Homologs or orthologs of the specific sequences can be obtained from a wide range of animals, plants and microorganisms. They are preferably obtained from algae. Algae such as *Isochrysis, Euglena* or *Crypthecodinium*, algae/diatoms such as *Thalassiosira, Phaeodactylum* or *Thraustochytrium, Pythium*, mosses such as *Physcomitrella*, preferably *Physcomitrella patens* or *Ceratodon* are preferred, very especially preferred are the algae of the genus *Euglena* or the diatoms of the class Oomycota such as the genera *Pythium* or *Phytophtora* or fungi such as *Postia placenta* or *Microdochium nivale*, or from the division Zygomycota from the genera *Rhizopus, Aspergillus, Thraustochytrium, Phytophthora, Entomophthora, Mucor* or *Mortierella*. The polynucleotides can also be obtained from plants, preferably from the family Selaginellaceae, such as *Selaginella moellendorffii*, or from higher plants such as Primulaceae such as *Aleuritia, Calendula stellata, Osteospermum spinescens* or *Osteospermum hyoseroides*, bacteria such as *Shewanella*, cyanobacteria such as *Synechococcus*, yeasts or animals such as nematodes, for example *Caenorhabditis, molluses*, insects or fish. The polynucleotide variants are also preferably derived from an animal from the order vertebrates. Especially preferably, the polynucleotides are derived from the class Vertebrata; Euteleostomi, Actinopterygii; Neopterygii; Teleostei; Euteleostei, Protacanthopterygii, Salmoniformes; Salmonidae or *Oncorhynchus* and, very especially preferably, from the order Salmoniformes such as the family Salmonidae, such as the genus *Salmo*, for example from the genera and species *Oncorhynchus mykiss, Trutta trutta* or *Salmo trutta fario*. Here, the polynucleotides according to the invention can be isolated by means of standard techniques of molecular biology and of the sequence information provided herein. Also, it is possible, with the aid of comparative algorithms, to identify for example a homologous sequence or homologous, conserved sequence regions at the DNA or amino acid level. These can be employed as hybridization probe and standard hybridization techniques (such as, for example, those described in Sambrook et al., Molecular Cloning: A Laboratory Manual. 2nd Ed., Cold Spring Harbor Laboratory, Cold Spring Harbor Laboratory Press, Cold Spring Harbor, N.Y., 1989) for isolating further nucleic acid sequences which are useful in the process. Moreover, it is possible to isolate polynucleotides or fragments thereof by means of polymerase chain reaction (PCR), where oligonucleotide primers which are based on this sequence or parts thereof are employed (for example, a nucleic acid molecule comprising the complete sequence or part thereof can be isolated by polymerase chain reaction using oligonucleotide primers which have been generated on the basis of this same sequence). For example, it is possible to isolate mRNA from cells (for example by the guanidinium thiocyanate extractive method by Chirgwin et al. (1979) Biochemistry 18:5294-5299), and cDNA can be generated by means of reverse transcriptase (for example Moloney MLV reverse transcriptase, obtainable from Gibco/BRL, Bethesda, Md., or AMV reverse transcriptase, obtainable from Seikagaku America, Inc., St. Petersburg, Fla.). Synthetic oligonucleotide primers for the amplification by means of polymerase chain reaction can be generated on the basis of the polynucleotide and amino acid sequences shown in the SEQ ID numbers (SEQ ID NR:). A nucleic acid according to the invention can be amplified using cDNA or, alternatively, genomic DNA as the template and suitable oligonucleotide primers, following standard PCR amplification techniques. The nucleic acid amplified thus can be cloned into a suitable vector and characterized by means of DNA sequence analysis. Oligonucleotides which correspond to a desaturase nucleotide sequence can be generated by standard synthetic methods, for example using an automatic DNA synthesizer.

The polynucleotides according to the invention can either be provided in the form of isolated polynucleotides (i.e. isolated from their natural origin, for example the genomic locus) or else in genetically modified form (i.e. the polynucleotides may also be present at their natural genetic locus, but, in such a case, must be genetically modified). An isolated polynucleotide preferably comprises less than 5 kb, 4 kb, 3 kb, 2 kb, 1 kb, 0.5 kb or 0.1 kb of nucleic acid sequence which occurs naturally in its environment. The polynucleotide according to the invention may be present as a single-stranded or double-stranded nucleic acid molecule and may take the form of genomic DNA, cDNA or RNA. Preferably, the polynucleotide according to the invention consists of RNA or DNA. The polynucleotides according to the invention comprise all orientations of the sequences shown in the SEQ ID numbers, i.e. also complementary strands and reverse, or reverse-complementary, orientations. The term furthermore also comprises chemically modified nucleic acids, such as the naturally occurring methylated DNA molecules, or artificial nucleic acids, for example biotinylated nucleic acids.

The invention also comprises oligonucleotides of at least 15 bp, preferably at least 20 bp, at least 25 bp, at least 30 bp, at least 35 bp or at least 50 bp, which are capable of specifically hybridizing under stringent conditions with one of the abovementioned polynucleotides. The oligonucleotides may consist of DNA or RNA or both. Such oligonucleotides can be employed as primers for the PCR, as expression-inhibitory antisense oligonucleotides, for RNA interference (RNAi) approaches or for chimeroplastic or genoplastic approaches. RNAi methods are described for example in Fire et al., Nature (1998) 391:806-811; Fire, Trends Genet. 15, 358-363 (1999); Sharp, RNA interference 2001. Genes Dev. 15, 485-490 (2001); Hammond et al. Nature Rev. Genet. 2, 1110-1119 (2001); Tuschl, Chem. Biochem. 2, 239-245 (2001); Hamilton et al., Science 286, 950-952 (1999); Hammond et al., Nature 404, 293-296 (2000); Zamore et al., Cell 101, 25-33 (2000); Bernstein et al., Nature 409, 363-366 (2001); Elbashir et al., Genes Dev. 15, 188-200 (2001); WO 01/29058; WO 99/32619; or Elbashir et al., 2001 Nature 411: 494-498 and serve for inhibiting gene expression by degrading the mRNA. Chimeroplastic or genoplastic approaches serve the in-vivo modification (for example the introduction of point mutations) into genes at their endogenous loci. Corresponding methods are disclosed in U.S. Pat. No. 5,565,350, U.S. Pat. No. 5,756,325, U.S. Pat. No. 5,871,984, U.S. Pat. No. 5,731,181, U.S. Pat. No. 5,795,972, U.S. Pat. No. 6,573,046, U.S. Pat. No. 6,211,351, U.S. Pat. No. 6,586,184, U.S. Pat. No. 6,271,360 and U.S. Pat. No. 6,479,292.

Advantageously, it has emerged that the polynucleotides according to the invention can be employed particularly efficiently for the recombinant production of polyunsaturated fatty acids in host cells and in transgenic organisms. In particular, the polypeptides which are encoded by the polynucleotides according to the invention and which have $\Delta$12-desaturase, $\Delta$15-desaturase, $\Delta$12- and $\Delta$15-desaturase or omega-3-desaturase activity are capable of converting C18-, C20- and C22-fatty acids with one, two, three, four or five double bonds and preferably polyunsaturated C18-fatty acids with one, two or three double bonds such as C18:1 (9, C18:2 (9,12 or C18:3 (6,9,12, polyunsaturated C20-fatty acids with three or four double bonds such as C20:3 (8,11,14, C20:4 (5,8,11,14 or C20:4(8,11,14,17 or polyunsaturated 022-fatty acids with four or five double bonds such as 022:4(7,10,13,16 or 022:5 (7,10,13,16,19. Especially preferably, the polynucleotide and amino acid sequences according to the invention lead to an increase in the 18:2(9,12- or 18:3(9,12,15-fatty acids. FIG. 1 shows where these desaturases according to the invention engage in the biosynthesis of long-chain polyunsaturated fatty acids and/or how they can be used for producing these fatty acids.

In this context, it is especially preferred to employ the $\Delta$6-desaturase encoded by the polynucleotide sequence with SEQ ID No. 22 (d6Des(Pir)), the $\Delta$6-elongase encoded by the polynucleotide sequence with SEQ ID No. 31 (d6Elo(Pp)), the $\Delta$5-desaturase encoded by the polynucleotide sequence with SEQ ID No. 25 (d5Des(Tc)), the $\Delta$15-elongase encoded by the polynucleotide sequence with SEQ ID No. 34 (d5Des (Ot)), the $\Delta$14-desaturase encoded by the polynucleotide sequence with SEQ ID No. 37 (d4Des(Tc)), the $\Delta$6-elongase encoded by the polynucleotide sequence with SEQ ID No. 40 (d6Elo(Tp)), the $\Delta$6-desaturase encoded by the polynucleotide sequence with SEQ ID No. 41 (d6Des(Tc)) with one or more of the desaturases according to the invention in order to synthesize long-chain polyunsaturated fatty acids; see in this context WO2006/100241. Alternatively, it was also possible to employ a $\Delta$9-elongase and a $\Delta$8-desaturase instead of the abovementioned $\Delta$6-desaturase and the $\Delta$6-elongase as described in WO2004/057001. Depending on the fatty acid which is to be prepared, it is possible to coexpress, in the host cells or transgenic organisms described hereinbelow, or to use in the methods according to the invention, a variety of combinations of the polynucleotides according to the invention with the abovementioned desaturases or elongases. Especially preferred combinations for the production of eicosapentaenoic acid are shown in tables 5 and 8 and for docosahexaenoic acid in table 6 hereinbelow. For example, it is possible to use a $\Delta$12-desaturase, $\Delta$15-desaturase, $\Delta$12- and $\Delta$15-desaturase, or omega-3-desaturase according to the invention, alone or in a suitable combination (for example a $\Delta$12-desaturase and a $\Delta$15-desaturase), together with d6Des (Pir) and/or d6Des(Ot), d6Elo(Pp), d5Des(Tc) and $\omega$3Des (Pi) for the production of EPA. Equally, a $\Delta$12-desaturase, $\Delta$15-desaturase, $\Delta$12- and $\Delta$15-desaturase, or omega-3-desaturase according to the invention, alone or in a suitable combination, can be used together with d6Des(Pir) and/or d6Des(Ot), d6Elo(Pp), d5Des(Tc), $\omega$3Des(Pi), d5Elo(Ot), d4Des(Tc) for the production of docosahexaenoic acid.

Preferably, it is the fatty acids in phospholipids or CoA fatty acid esters which are desaturated, advantageously in the CoA fatty acid esters. Thus, a simple, inexpensive production of these polyunsaturated fatty acids is possible, specifically in eukaryotic systems. The unsaturated fatty acids produced by means of the polynucleotides according to the invention can then be formulated as oil, lipid and fatty acid compositions and can be employed in a suitable manner.

The present invention furthermore relates to a vector which comprises the polynucleotide according to the invention.

The term "vector" refers to a nucleic acid molecule which is capable of transporting another nucleic acid molecule, such as the polynucleotides according to the invention, to which it is bound. One type of vector is a plasmid, a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as expression vectors. Usually, expression vectors which are suitable for DNA recombination techniques take the form of plasmids. In the present description, "plasmid" and "vector" can be used exchangeably since the plasmid is the form of vector which is most frequently used. However, the invention is also intended to comprise other forms of expression vectors, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA, artificial chromosomes. Finally, the term also comprises constructs for the targeted, i.e. homologous, recombination, or the heterologous insertion of polynucleotides.

Vectors can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Suitable cloning vectors are generally known to the skilled worker. In particular, they include vectors which can replicate in microbial systems, that is mainly vectors which ensure efficient cloning in yeasts or fungi and which make possible the stable transformation of plants. Those which must be mentioned are in particular various binary and cointegrated vector systems which are suitable for the T-DNA-mediated transformation. Such vector systems are, as a rule, characterized in that they comprise at least the vir genes, which are required for the *agrobacterium*-mediated transformation, and the T-DNA-bordering sequences (T-DNA border). Preferably, these vector systems also comprise further cis-regulatory regions such as promoters and terminators and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, and the other bears T-DNA, but no vir gene. As a result, the last-mentioned vectors are relatively small, easy to manipulate and to replicate both in *E. coli* and in *Agrobacterium*. These binary vectors include vectors from the pBIB-HYG series, the pPZP series, the pBecks series and the pGreen series. Preferably used according to the invention are Bin19, pB1101, pBinAR, pGPTV and pCAMBIA. An overview of binary vectors and their use is found in Hellens et al, Trends in Plant Science (2000) 5, 446-451. The vectors with the inserted polynucleotides according to the invention can be propagated stably under selective conditions in microorganisms, in particular *Escherichia coli* and *Agrobacterium tumefaciens*, and make possible a transfer of heterologous DNA into plants or microorganisms. The polynucleotides according to the invention can be introduced into organisms such as microorganisms or plants by means of the cloning vectors and thus used for transforming plants. Vectors which are suitable for this purpose are published in: Plant Molecular Biology and Biotechnology (CRC Press, Boca Raton, Fla.), chapter 6/7, p. 71-119 (1993); F. F. White, Vectors for Gene Transfer in Higher Plants; in: Transgenic Plants, vol. 1, Engineering and Utilization, eds.: Kung and R. Wu, Academic Press, 1993, 15-38; B. Jenes et al., Techniques for Gene Transfer, in: Transgenic Plants, vol. 1, Engineering and Utilization, eds.: Kung and R. Wu, Academic Press (1993), 128-143; Potrykus, Annu. Rev. Plant Physiol. Plant Molec. Biol. 42 (1991), 205-225.

The vector is preferably an expression vector. The polynucleotide is present in the expression vector according to the invention in operative (i.e. functional) linkage with an expression control sequence. The expression control sequence together with the polynucleotide and optionally further sequence elements of the vector is also referred to as the expression cassette. The expression control sequence ensures that, after transformation or transfection into a host cell, the polynucleotide can be expressed. The expression control sequence to be used preferably comprises cis-regulatory elements such as promoter and/or enhancer nucleic acid sequences, which are recognized by the transcription machinery of the host cells. The term furthermore comprises other expression control elements, for example polyadenylation signals and RNA-stabilizing sequences. These regulatory sequences are described for example in Goeddel: Gene Expression Technology: Methods in Enzymology 185, Academic Press, San Diego, Calif. (1990) or see: Gruber and Crosby, in: Methods in Plant Molecular Biology and Biotechnology, CRC Press, Boca Raton, Fla., eds.: Glick and Thompson, chapter 7, 89-108, including the literature cited therein. Expression control sequences comprise those which govern the constitutive expression of a nucleotide sequence in many types of host cells, and those which govern the direct expression of the nucleotide sequence only in certain host cells under certain conditions. The skilled worker knows that the design of the expression vector may depend on factors such as the choice of the host cell to be transformed, the extent of the expression of the desired protein and the like. The polynucleotides according to the invention may be present in one or more copies in the expression cassette or in the expression vector according to the invention (for example in the form of several expression cassettes). Here, the regulatory sequences or factors can preferably have a positive effect on the gene expression of the introduced genes, as described above, and thereby increase it. Thus, it is possible to enhance the regulatory elements advantageously at the transcription level by using strong transcription signals such as promoters and/or "enhancers". Besides, it is also possible to enhance the translation, for example by improving the mRNA stability. Further expression control sequences within the meaning of the present invention are translation terminators at the 3' end of the polynucleotides to be translated. An example which can be used here is the OCS1 terminator. As in the case of the promoters, a different terminator sequence should be used for each polynucleotide to be expressed.

Preferred expression control sequences or regulatory sequences are present in promoters such as the cos, tac, trp, tet, trp-tet, lpp, lac, lpp-lac, laclq, T7, T5, T3, gal, trc, ara, SP6, λ-PR or λ-PL promoters and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscisic acid-inducible) or WO 93/21334 (ethanol- or cyclohexenol-inducible). Further suitable plant promoters are the cytosolic FBPase promoter or the ST-LSI promoter of potato (Stockhaus et al., EMBO J. 8, 1989, 2445), the *glycine max* phosphoribosyl-pyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arobidopsis oleosin* promoter), U.S. Pat. No. 5,504,200 (*Phaseolus vulgaris* phaseolin promoter), WO 91/13980 (*Brassica* Bce4 promoter), by Baeumlein et al., Plant J., 2, 2, 1992:233-239 (LeB4 promoter from a legume), these promoters being suitable for dicots.

Examples of promoters which are suitable for monocots are the barley lpt-2 or lpt-1 promoter (WO 95/15389 and WO 95/23230), the barley hordein promoter and other suitable promoters described in WO 99/16890. In principle, it is possible to use all natural promoters together with their regulatory sequences, such as those mentioned above, as expression control sequences. It is also possible to use synthetic promoters, either in addition or alone, in particular when they mediate seed-specific expression, as described, for example, in WO 99/16890.

In order to achieve a particularly high PUFA content, especially in transgenic plants, the polynucleotides of the present invention should preferably be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Advantageous preferred promoters are listed hereinbelow: USP (=unknown seed protein) and vicilin (*Vicia faba*) [Bäumlein et al., Mol. Gen. Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Bäumlein et al., Plant J., 2,2, 1992], Lpt2 and Ipt1 (barley) [WO 95/15389 and WO 95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see a review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic acid-inducible promoter (WO 95/19443), a tetracycline-inducible promoter (Gatz et al. (1992) Plant J. 2, 397-404) and an ethanol-inducible promoter.

To ensure stable integration of the various biosynthesis genes into the transgenic plant over a plurality of generations, each of the polynucleotides according to the invention should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site (advantageously in a polylinker) for insertion of the nucleic acid to be expressed and, if appropriate, a terminator is then positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator. Such advantageous constructs are disclosed, for example, in DE 101 02 337 or DE 101 02 338. However, it is also possible to insert a plurality of nucleic acid sequences behind a promoter and, if appropriate, in front of a terminator. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoters, and different terminators can be used in the expression cassette. However, it is also possible to use only one type of promoter in the cassette. This, however, may lead to undesired recombination events.

The recombinant expression vectors used can be designed for the expression in prokaryotic or eukaryotic cells. This is advantageous since intermediate steps of the vector construction are frequently carried out in microorganisms for the sake of simplicity. For example, the Δ12-desaturase, Δ15-desaturase, Δ12- and 415-desaturases, ω3-desaturase, Δ6-desaturase, Δ6-elongase, Δ9-elongase, Δ8-desaturase, Δ5-desaturase, Δ5-elongase and/or Δ4-desaturase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Eds., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Eds., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturapseudocohnilembus, Euplotes, Engelmaniella* and *Stylonychia*, in particular of the genus *Stylonychia lemnae*, using vectors in a transformation method as described in WO 98/01572 and, preferably, in cells of multi-cellular plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Eds.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or nonfusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E-binding protein and protein A, respectively, are fused with the recombinant target protein. Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the vector pTrc is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophagene which harbors a T7 gn1 gene under the transcriptional control of the lacUV 5 promoter. Other vectors which are suitable for prokaryotic organisms are known to the skilled worker, these vectors are, for example in *E. coli* pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSΔ77 or pAJ667.

In a further embodiment, the expression vector is a yeast expression vector. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Eds., pp. 396-428: Academic Press: San Diego]. Further suitable yeast vectors are, for example, pAG-1, YEp6, YEp13 or pEMBLYe23.

As an alternative, the polynucleotides of the present invention can also be expressed in insect cells using Baculovirus expression vectors. Baculovirus vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

Preferred plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Eds.: Kung and R. Wu, Academic Press, 1993, p. 15-38. A plant expression cassette preferably comprises expression control sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminators which are functionally active in plants are also suitable. Since plant gene expression is very often not limited to transcriptional levels, a plant expression cassette preferably comprises other sequences which are linked operably, such as translation enhancers, for example the overdrive sequence, which comprises the tobacco mosaic virus 5'-untranslated leader sequence, which increases the protein/RNA ratio (Gallie et al., 1987, Nucl. Acids Research 15:8693-8711). As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CAMV (Franck et al., Cell 21 (1980) 285-294), 19S CaMV (see also U.S. Pat. No. 5,352,605 and WO 84/02913), or plant promoters, such as the promoter of the small Rubisco subunit, which is described in U.S. Pat. No. 4,962,028. Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmic reticulum, oil bodies, peroxisomes and other compartments of plant cells.

As described above, plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter. Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as the cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley Ipt2 or Ipt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890. Especially suitable promoters are likewise those which bring about the plastid-specific expression, since plastids are the compartment in which the precursors and some of the end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

The abovementioned vectors are only a small overview of possible vectors which are suitable. Further plasmids are known to the skilled worker and are described for example in: Cloning Vectors (eds. Pouwels, P. H., et al., Elsevier, Amsterdam-New York-Oxford, 1985, ISBN 0 444 904018). Further suitable expression systems for prokaryotic and eukaryotic cells, see chapters 16 and 17 of Sambrook, J., Fritsch, E. F., and Maniatis, T., Molecular Cloning: A Laboratory Manual, 2nd ed., Cold Spring Harbor Laboratory, Cold Spring Harbor Laboratory Press, Cold Spring Harbor, N.Y., 1989.

As described above, the expression vector can, in addition to the polynucleotides according to the invention, also comprise further genes which are to be introduced into the organisms. It is possible and preferred to introduce into the host organisms, and express in them, regulatory genes, such as genes for inductors, repressors or enzymes which, as a result of their enzymatic activity, engage in the regulation of one or more genes of a biosynthetic pathway. These genes can be of heterologous or homologous origin. Heterologous genes or polynucleotides are derived from an organism of origin which differs from the target organism into which the genes or polynucleotides are to be introduced. In the case of homologous genes or polynucleotides, target organism and organism of origin are identical. The vector therefore preferably comprises at least one further polynucleotide which codes for a further enzyme which is involved in the biosynthesis of lipids or fatty acids. The enzyme is preferably selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), $\Delta 4$-desaturase(s), $\Delta 5$-desaturase(s), $\Delta 6$-desaturase(s), $\Delta 8$-desaturase(s), $\Delta 9$-desaturase(s), $\Delta 12$-desaturase(s), $\Delta 15$-desaturase(s), $\Delta 12$- and $\Delta 15$-desaturase(s), $\omega 3$-desaturase, $\Delta 5$-elongase(s), $\Delta 6$-elongase(s) and $\Delta 9$-elongase(s).

Especially preferred gene combinations are listed in tables 5 and 6 in the examples which follow.

The invention also relates to a host cell which comprises the polynucleotide according to the invention or the vector according to the invention.

In principle, host cells for the purposes of the present invention may be all eukaryotic or prokaryotic cells. They may be primary cells from animals, plants or multi-celled microorganisms, for example from those which are mentioned in another place in the description. The term furthermore also comprises cell lines which can be obtained from these organisms.

However, host cells for the purposes of the invention may also be single-celled microorganisms, for example bacteria or fungi. Especially preferred microorganisms are fungi selected from the group of the families Chaetomiaceae, Choanephoraceae, Cryptococcaceae, Cunninghamellaceae, Demetiaceae, Hydnangiaceae (genus *Laccaria*), Moniliaceae, Mortierellaceae, Mucoraceae, Pythiaceae, Sacharomycetaceae, Saprolegniaceae, Schizosacharomycetaceae, Sodariaceae or Tuberculariaceae. Further preferred microorganisms are selected from the group: Choanephoraceae, such as the genera *Blakeslea, Choanephora*, for example the genera and species *Blakeslea trispora, Choanephora cucurbitarum, Choanephora infundibulifera* var. *cucurbitarum*, Hydnangiaceae (for example genus *Laccaria*, in particular species *Laccaria bicolor*), Mortierellaceae, such as the genus *Mortierella*, for example the genera and species *Mortierella isabellina, Mortierella polycephala, Mortierella ramanniana, Mortierella vinacea, Mortierella zonata*, the family Mucorales, such as the genera and species *Rhizopus oryzae, Rhizopus stolonifer, Fusarium graminearium*, Pythiaceae, such as the genera *Phytium, Phytophthora*, for example the genera and species *Pythium debaryanum, Pythium intermedium, Pythium irregulare, Pythium megalacanthum, Pythium paroecandrum, Pythium sylvaticum, Pythium ultimum, Phytophthora cactorum, Phytophthora cinnamomi, Phytophthora citricola, Phytophthora citrophthora, Phytophthora cryptogea, Phytophthora drechsleri, Phytophthora erythroseptica, Phytophthora lateralis, Phytophthora megasperma, Phytophthora nicotianae, Phytophthora nicotianae* var. *parasitica, Phytophthora palmivora, Phytophthora parasitica, Phytophthora syringae*, Saccharomycetaceae, such as the genera *Hansenula, Pichia, Saccharomyces, Saccharomycodes, Yarrowia*, for example the genera and species *Hansenula anomala, Hansenula californica, Hansenula canadensis, Hansenula capsulata, Hansenula ciferrii, Hansenula glucozyma, Hansenula henricii, Hansenula holstii, Hansenula minuta, Hansenula nonfermentans, Hansenula philodendri, Hansenula polymorpha, Hansenula saturnus, Hansenula subpelliculosa, Hansenula wickerhamii, Hansenula wingei, Pichia alcoholophila, Pichia angusta, Pichia anomala, Pichia bispora, Pichia burtonii, Pichia canadensis, Pichia capsulata, Pichia carsonii, Pichia cellobiosa, Pichia ciferrii, Pichia farinosa, Pichia fermentans, Pichia finlandica, Pichia glucozyma, Pichia guilfiermondii, Pichia haplophila, Pichia henricii, Pichia holstii, Pichia jadinii, Pichia lindnerii, Pichia membranaefaciens, Pichia methanolica, Pichia minuta* var. *minuta, Pichia minuta* var. *nonfermentans, Pichia norvegensis, Pichia ohmeri, Pichia pastoris, Pichia philodendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceti, Saccharomyces bailii, Saccharomyces bayanus, Saccharomyces bisporus, Saccharomyces capensis, Saccharomyces carlsbergensis, Saccharomyces cerevisiae, Saccharomyces cerevisiae* var. *ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii, Yarrowia lipolytica*, Schizosaccharomycetaceae such as the genera *Schizosaccharomyces* e.g. the species *Schizosaccharomyces japonicus* var. *japonicus, Schizosaccharomyces japonicus* var. *versatilis, Schizosaccharomyces malidevorans, Schizosaccharomyces octosporus, Schizosaccharomyces pombe* var. *malidevorans, Schizosaccharomyces pombe* var. *pombe*, Thraustochytriaceae such as the genera *Althornia, Aplanochytrium, Japonochytrium, Schizochytrium, Thraustochytrium* e.g. the species *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium

*globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense*.

Equally preferred as microorganisms are bacteria selected from the group of the families Bacillaceae, Enterobacteriacae or Rhizobiaceae. It is especially preferred to mention the following bacteria selected from the group: Bacillaceae, such as the genus *Bacillus*, for example the genera and species *Bacillus acidocaldarius, Bacillus acidoterrestris, Bacillus alcalophilus, Bacillus amyloliquefaciens, Bacillus amyloyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia*, for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter* sp., *Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia coli*-mutabile, *Escherichia fergusonii, Escherichia hermannii, Escherichia* sp., *Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella* sp., *Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *choleraesuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizobiaceae, such as the genera *Agrobacterium, Carbophilus, Chelatobacter, Ensifer, Rhizobium, Sinorhizobium*, for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri, Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium suttee, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense*.

Further utilizable host cells are detailed in: Goeddel, Gene Expression Technology: Methods in Enzymology 185, Academic Press, San Diego, Calif. (1990). Expression strains which can be used, for example those with a lower protease activity, are described in: Gottesman, S., Gene Expression Technology: Methods in Enzymology 185, Academic Press, San Diego, Calif. (1990) 119-128. These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

Polynucleotides or vectors can be introduced into the host cell as described above by means of transformation or transfection methods which are known in the prior art. Conditions and media for the cultivation of the host cells are also known to the skilled worker.

The host cell according to the invention preferably additionally comprises at least one further enzyme which is involved in the biosynthesis of lipids or fatty acids. Preferred enzymes have already been mentioned in another place in the description. The enzyme can be present in the host cell in endogenous form, i.e. the host cell already naturally expresses a gene which codes for a corresponding enzyme. Alternatively, it is also possible to introduce, into the host cell, a heterologous polynucleotide which codes for the enzyme. Suitable methods and means for the expression of a heterologous polynucleotide are known in the prior art and are described herein in connection with the polynucleotides, vectors and host cells according to the invention.

The invention also relates to a method of generating a polypeptide with desaturase activity, comprising the steps:
(a) expressing a polynucleotide according to the invention as defined above in a host cell; and
(b) obtaining, from the host cell, the polypeptide which is encoded by the polynucleotide in (a).

In this context, the polypeptide can be obtained or isolated by all current protein purification methods. The methods comprise, for example, affinity chromatography, molecular sieve chromatography, high-pressure liquid chromatography or else protein precipitation, if appropriate with specific antibodies. Although this is preferred, the process need not necessarily provide a pure polypeptide preparation.

The invention therefore also relates to a polypeptide which is encoded by the polynucleotide according to the invention or which is obtainable by the abovementioned method according to the invention.

The term "polypeptide" refers both to an essentially pure polypeptide, and also to a polypeptide preparation which additionally comprises further components or impurities. The term is also used for fusion proteins and protein aggregates which comprise the polypeptide according to the invention and additionally further components. The term also refers to chemically modified polypeptides. In this context, chemical modifications comprise artificial modifications or naturally occurring modifications, for example posttranslational modifications such as phosphorylation, myristylation, glycosylation and the like. The terms polypeptide, peptide and protein are interchangeable and are used accordingly in the description and in the prior art. The polypeptides according to the invention have the abovementioned biological activities, that is to say desaturase activities, and can influence the biosynthesis of polyunsaturated fatty acids (PUFAs), preferably the long-chain PUFAs (LCPUFAs), as herein described.

The invention also comprises an antibody which specifically recognizes the polypeptide according to the invention.

Antibodies against the polypeptide according to the invention can be prepared by means of known methods, where purified polypeptide or fragments thereof with suitable epitopes are used as the antigen. Suitable epitopes can be determined by means of known algorithms for the antigenicity determination, based on the amino acid sequences of the polypeptides according to the invention provided herein. The relevant polypeptides or fragments can then be synthesized or obtained by recombinant techniques. After suitable animals, preferably mammals, for example hares, rats or mice, have been immunized, the antibodies can then be obtained from the serum, using known methods. Alternatively, monoclonal antibodies or antibody fragments can be provided with the known methods; see, for example, Harlow and Lane "Antibodies, A Laboratory Manual", CSH Press, Cold Spring Harbor, 1988 or Köhler and Milstein, Nature 256 (1975), 495, and Galfré, Meth. Enzymol. 73 (1981), 3.

The antibodies preferably take the form of monoclonal or polyclonal antibodies, single-chain antibodies or chimeric antibodies, and fragments of these such as Fab, Fv or scFv. Further antibodies within the meaning of the invention are bispecific antibodies, synthetic antibodies or their chemically modified derivatives.

The antibodies according to the invention specifically recognize the polypeptides according to the invention, that is to say they do not cross-react significantly with other proteins. For example, an antibody according to the invention which specifically binds a Δ12-desaturase will not react with a Δ6-desaturase. This can be assayed by means of methods known in the prior art. For example, the antibodies can be employed for the purposes of detection reactions, immunoprecipitation, immunhistochemistry or protein purification (for example affinity chromatography).

The invention furthermore relates to a transgenic, nonhuman organism which comprises the polynucleotide, the vector or the host cell of the present invention. The transgenic, nonhuman organism preferably takes the form of an animal, a plant or a multicellular microorganism.

The term "transgenic" is understood as meaning that a heterologous polynucleotide, that is to say a polynucleotide which does not occur naturally in the respective organism, is introduced into the organism. This can be achieved either by random insertion of the polynucleotide or by homologous recombination. Naturally, it is also possible to introduce the vector according to the invention instead of the polynucleotide. Methods of introducing polynucleotides or vectors for the purposes of random insertion or homologous recombination are known in the prior art and also described in greater detail hereinbelow. Host cells which comprise the polynucleotide or the vector can also be introduced into an organism and thus generate a transgenic organism. In such a case, such an organism takes the form of a chimeric organism, where only those cells which are derived from the introduced cells are transgenic, i.e. comprise the heterologous polynucleotide.

The transgenic nonhuman organisms are preferably oil-producing organisms, which means organisms which are used for the production of oils, for example fungi such as *Rhizopus* or *Thraustochytrium*, algae such as *Euglena, Nephroselmis, Pseudoscourfielda, Prasinococcus, Scherffelia, Tetraselmis, Mantoniella, Ostreococcus, Crypthecodinium, Phaeodactylum*, or diatoms such as *Pythium* or *Phytophthora* or plants.

Transgenic plants which can be used are, in principle, all plants, that is to say both dicotyledonous and monocotyledonous plants. They preferably take the form of oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, verbascum, thistle, wild roses, hazelnut, almond, macadamia, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, tobacco, verbascum, sesame, cotton, pumpkin/squash, poppy, evening primrose, walnut, linseed, hemp, thistle or safflower. Very especially preferred plants are plants such as safflower, sunflower, poppy, evening primrose, walnut, linseed or hemp. In principle, however, all plants which are capable of synthesizing fatty acids are suitable, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*.

Examples which may especially preferably be mentioned are the following plants selected from the group consisting of: Adelotheciaceae such as the genera *Physcomitrella*, for example the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa*, *Lactuca crispa*, *Lactuca esculenta*, *Lactuca scariola* L. ssp. *sativa*, *Lactuca scariola* L. var. *integrata*, *Lactuca scariola* L. var. *integrifolia*, *Lactuca sativa* subsp. *romana*, *Locusta communis*, *Valeriana locusta* [salad vegetables], *Tagetes lucida*, *Tagetes erecta* or *Tagetes tenuifolia* [African or French marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica*, *Camelina*, *Melanosinapis*, *Sinapis*, *Arabadopsis*, for example the genera and species *Brassica napus*, *Brassica rapa* ssp. [oilseed rape], *Sinapis arvensis Brassica juncea*, *Brassica juncea* var. *juncea*, *Brassica juncea* var. *crispifolia*, *Brassica juncea* var. *foliosa*, *Brassica nigra*, *Brassica sinapioides*, *Camelina sativa*, *Melanosinapis communis* [mustard], *Brassica oleracea* [fodder beet] or *Arabadopsis thaliana*, Bromeliaceae, such as the genera *Ananas*, *Bromelia* (pineapple), for example the genera and species *Ananas comosus*, *Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sative* [hemp], Convolvulaceae, such as the genera *Ipomea*, *Convolvulus*, for example the genera and species *Ipomoea batatus*, *Ipomoea pandurata*, *Convolvulus batatas*, *Convolvulus tiliaceus*, *Ipomoea fastigiata*, *Ipomoea tiliacea*, *Ipomoea triloba* or *Convolvulus panduratus* [sweet potato, batate], Chenopodiaceae, such as the genus *Beta*, such as the genera and species *Beta vulgaris*, *Beta vulgaris* var. *altissima*, *Beta vulgaris* var. *vulgaris*, *Beta maritima*, *Beta vulgaris* var. *perennis*, *Beta vulgaris* var. *conditiva* or *Beta vulgaris* var. *esculents* [sugarbeet], Crypthecodiniaceae, such as the genus *Crypthecodinium*, for example the genus and species *Crypthecodinium cohnii*, Cucurbitaceae, such as the genus *Cucurbita*, for example the genera and species *Cucurbita maxima*, *Cucurbita mixta*, *Cucurbita pepo* or *Cucurbita moschata* [pumpkin/squash], Cymbellaceae, such as the genera *Amphora*, *Cymbella*, *Okedenia*, *Phaeodactylum*, *Reimeria*, for example the genus and species *Phaeodactylum tricornutum*, Ditrichaceae, such as the genera *Ditrichaceae*, *Astomiopsis*, *Ceratodon*, *Chrysoblastella*, *Ditrichum*, *Distichium*, *Eccremidium*, *Lophidion*, *Philibertiella*, *Pleuridium*, *Saelania*, *Trichodon*, *Skottsbergia*, for example the genera and species *Ceratodon antarcticus*, *Ceratodon columbiae*, *Ceratodon heterophyllus*, *Ceratodon purpurascens*, *Ceratodon purpureus*, *Ceratodon purpureus* ssp. *convolutus*, *Ceratodon purpureus* ssp. *stenocarpus*, *Ceratodon purpureus* var. *rotundifolius*, *Ceratodon ratodon*, *Ceratodon stenocarpus*, *Chrysoblastella chilensis*, *Ditrichum ambiguum*, *Ditrichum brevisetum*, *Ditrichum crispatissimum*, *Ditrichum difficile*, *Ditrichum falcifolium*, *Ditrichum flexicaule*, *Ditrichum giganteum*, *Ditrichum heteromallum*, *Ditrichum lineare*, *Ditrichum montanum*, *Ditrichum pallidum*, *Ditrichum punctulatum*, *Ditrichum pusillum*, *Ditrichum pusillum* var. *tortile*, *Ditrichum rhynchostegium*, *Ditrichum schimperi*, *Ditrichum tortile*, *Distichium capillaceum*, *Distichium hagenii*, *Distichium inclinatum*, *Distichium macounii*, *Eccremidium floridanum*, *Eccremidium whiteleggei*, *Lophidion strictus*, *Pleuridium acuminatum*, *Pleuridium altemifolium*, *Pleuridium holdridgei*, *Pleuridium mexicanum*, *Pleuridium ravenelii*, *Pleuridium subulatum*, *Saelania glaucescens*, *Trichodon borealis*, *Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia*, *Kalmia angustifolia*, *Kalmia microphylla*, *Kalmia polifolia*, *Kalmia occidentalis*, *Cistus chamaerhodendros* or *Kalmia lucida* [mountain laurel], Euphorbiaceae, such as the genera *Manihot*, *Janipha*, *Jatropha*, *Ricinus*, for example the genera and species *Manihot utilissima*, *Janipha manihot*, *Jatropha manihot*, *Manihot aipil*, *Manihot dulcis*, *Manihot manihot*, *Manihot melanobasis*, *Manihot esculenta* [cassava] or *Ricinus communis* [castor-oil plant], Fabaceae, such as the genera *Pisum*, *Albizia*, *Cathormion*, *Feuillea*, *Inga*, *Pithecolobium*, *Acacia*, *Mimosa*, *Medicago*, *Glycine*, *Dolichos*, *Phaseolus*, soybean, for example the genera and species *Pisum sativum*, *Pisum arvense*, *Pisum humile* [pea], *Albizia berteriana*, *Albizia julibrissin*, *Albizia lebbeck*, *Acacia berteriana*, *Acacia littoralis*, *Albizia berteriana*, *Albizzia berteriana*, *Cathormion berteriana*, *Feuillea berteriana*, *Inga fragrans*, *Pithecellobium berterianum*, *Pithecellobium fragrans*, *Pithecolobium berterianum*, *Pseudalbizzia berteriana*, *Acacia julibrissin*, *Acacia nemu*, *Albizia nemu*, *Feuilleea julibrissin*, *Mimosa julibrissin*, *Mimosa speciosa*, *Sericandra julibrissin*, *Acacia lebbeck*, *Acacia macrophylla*, *Albizia lebbeck*, *Feuilleea lebbeck*, *Mimosa lebbeck*, *Mimosa speciosa* [silk tree], *Medicago sativa*, *Medicago falcata*, *Medicago varia* [alfalfa] *Glycine max Dolichos soja*, *Glycine gracilis*, *Glycine hispida*, *Phaseolus max*, *Soja hispida* or *Soja max* [soybean], Funariaceae, such as the genera *Aphanorrhegma*, *Entosthodon*, *Funaria*, *Physcomitrella*, *Physcomitrium*, for example the genera and species *Aphanorrhegma serratum*, *Entosthodon attenuatus*, *Entosthodon bolanderi*, *Entosthodon bonplandii*, *Entosthodon californicus*, *Entosthodon drummondii*, *Entosthodon jamesonii*, *Entosthodon leibergii*, *Entosthodon neoscoticus*, *Entosthodon rubrisetus*, *Entosthodon spathulifolius*, *Entosthodon tucsoni*, *Funaria americana*, *Funaria bolanderi*, *Funaria calcarea*, *Funaria californica*, *Funaria calvescens*, *Funaria convoluta*, *Funaria flavicans*, *Funaria groutiana*, *Funaria hygrometrica*, *Funaria hygrometrica* var. *arctica*, *Funaria hygrometrica* var. *calvescens*, *Funaria hygrometrica* var. *convoluta*, *Funaria hygrometrica* var. *muralis*, *Funaria hygrometrica* var. *utahensis*, *Funaria microstoma*, *Funaria microstoma* var. *obtusifolia*, *Funaria muhlenbergii*, *Funaria orcuttii*, *Funaria piano-convexa*, *Funaria polaris*, *Funaria ravenelii*, *Funaria rubriseta*, *Funaria serrata*, *Funaria sonorae*, *Funaria sublimbatus*, *Funaria tucsoni*, *Physcomitrella californica*, *Physcomitrella patens*, *Physcomitrella readeri*, *Physcomitrium australe*, *Physcomitrium californicum*, *Physcomitrium collenchymatum*, *Physcomitrium coloradense*, *Physcomitrium cupuliferum*, *Physcomitrium drummondii*, *Physcomitrium eurystomum*, *Physcomitrium flexifolium*, *Physcomitrium hookeri*, *Physcomitrium hookeri* var. *serratum*, *Physcomitrium immersum*, *Physcomitrium kellermanii*, *Physcomitrium megalocarpum*, *Physcomitrium pyriforme*, *Physcomitrium pyriforme* var. *serratum*, *Physcomitrium rufipes*, *Physcomitrium sandbergii*, *Physcomitrium subsphaericum*, *Physcomitrium washingtoniense*, Geraniaceae, such as the genera *Pelargonium*, *Cocos*, *Oleum*, for example the genera and species *Cocos nucifera*, *Pelargonium grossularioides* or *Oleum cocois* [coconut], Gramineae, such as the genus *Saccharum*, for example the genus and species *Saccharum officinarum*, Juglandaceae, such as the genera *Juglans*, *Wallia*, for example the genera and species *Juglans regia*, *Juglans ailanthifolia*, *Juglans sieboldiana*, *Juglans cinerea*, *Wallia cinerea*, *Juglans bixbyi*, *Juglans californica*, *Juglans hindsii*, *Juglans interme-* dia, *Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize] *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia* [macadamia], Prasinophyceae, such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae, such as the genus *Coffea*, for example the genera and species *Coffea* spp., *Coffea arabica, Coffea canephora* or *Coffea liberica* [coffee], Scrophulariaceae, such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [verbascum], Solanaceae, such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Multicellular microorganisms which can be employed as transgenic nonhuman organisms are preferably protists or diatoms selected from the group of the families Dinophyceae, Turaniellidae or Oxytrichidae, such as the genera and species: *Crypthecodinium cohnii, Phaeodactylum tricomutum, Stylonychia mytilus, Stylonychia pustulata, Stylonychia putrina, Stylonychia notophora, Stylonychia* sp., *Colpidium campylum* or *Colpidium* sp.

The invention further relates to a process for the production of a substance which has the structure shown in the general formula I hereinbelow

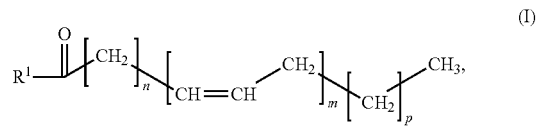

wherein the variables and substituents are as follows:
$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

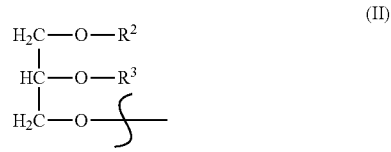

$R^2$=hydrogen, phosphatidylcholine, phosphatidylethanolamine, phosphatidyl-serine, phosphatidylinositol or a saturated or unsaturated C2 to $C_{24}$-alkylcarbonyl,
$R^3$=hydrogen, a saturated or unsaturated $C_2$ to $C_{24}$-alkylcarbonyl, or $R^2$ and $R^3$ independently of one another are a radical of the formula Ia:

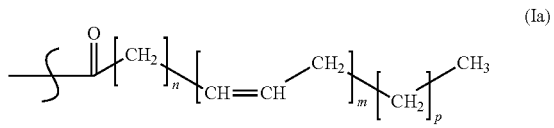

(Ia)

in which n=2, 3, 4, 5, 6, 7 or 9, m=2, 3, 4, 5 or 6 and p=0 or 3; and wherein the process comprises the cultivation of (i) a host cell according to the invention or (ii) of a transgenic, nonhuman organism according to the invention under conditions which permit the biosynthesis of the substance. Preferably, the abovementioned substance is provided in an amount of at least 1% by weight based on the total lipid content in the host cell or the transgenic organism.

Preferred alkyl radicals $R^2$ which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These preferred radicals can comprise two, three, four, five or six double bonds. The especially preferred radicals with 20 or 22 carbon atoms in the fatty acid chain comprise up to six double bonds, preferably three, four, five or six double bonds, especially preferably five or six double bonds. All the abovementioned radicals are derived from the corresponding fatty acids.

Preferred alkyl radicals $R^3$ which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These preferred radicals can comprise two, three, four, five or six double bonds. The especially preferred radicals with 20 or 22 carbon atoms in the fatty acid chain comprise up to six double bonds, preferably three, four, five or six double bonds, especially preferably five or six double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The polyunsaturated fatty acids produced in the process according to the invention advantageously comprise at least two, advantageously three, four, five or six, double bonds. The fatty acids especially advantageously comprise four, five or six double bonds. Fatty acids produced in the process advantageously have 18, 20 or 22 C atoms in the fatty acid chain; the fatty acids preferably comprise 20 or 22 carbon atoms in the fatty acid chain. Saturated fatty acids are advantageously reacted to a minor degree, or not at all, with the nucleic acids used in the process. To a minor degree is to be understood as meaning that the saturated fatty acids are reacted with less than 5% of the activity, advantageously less than 3%, especially advantageously with less than 2%, very especially preferably with less than 1, 0.5, 0.25 or 0.125% in comparison with polyunsaturated fatty acids. These fatty acids which have been produced can be produced in the process as a single product or be present in a fatty acid mixture.

The radicals $R^2$ or $R^3$ in the general formulae II may be identical or non-identical, $R^2$ and $R^3$ preferably being a saturated or unsaturated $C_{18}$-$C_{22}$-alkylcarbonyl, especially preferably an unsaturated $C_{18}$-, $C_{20}$- or $C_{22}$-alkylcarbonyl with at least two double bonds.

The polyunsaturated fatty acids produced in the process are advantageously bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms; preferred are long-chain fatty acids, more preferably long-chain fatty acids LCPUFAs of $C_{18}$-, $C_{20}$- and/or $C_{22}$-fatty acids.

The process according to the invention advantageously yields fatty acid esters with polyunsaturated $C_{18}$-, $C_{20}$- and/or $C_{22}$-fatty acid molecules with at least two double bonds in the fatty acid ester, advantageously with at least three, four, five or six double bonds in the fatty acid ester, especially advantageously with at least five or six double bonds in the fatty acid ester and advantageously leads to the synthesis of linoleic acid (=LA, C18:$2^{\Delta9,12}$), γ-linolenic acid (=GLA, C18:$3^{\Delta6,9,12}$), stearidonic acid (=SDA, C18:$4^{\Delta6,9,12,15}$) dihomo-γ-linolenic acid (=DGLA, 20:$3^{\Delta8,11,14}$), ω3-eicosatetraenoic acid (=ETA, C20:$4^{\Delta5,8,11,14}$) arachidonic acid (ARA, C20:$4^{\Delta5,8,11,14}$) eicosapentaenoic acid (EPA, C20:

$5^{\Delta5,8,11,14,17}$), ω6-docosapentaenoic acid (C22:$5^{\Delta4,7,10,13,16}$), ω6-docosatetraenoic acid (C22:$4^{\Delta7,10,13,16}$), ω3-docosapentaenoic acid (=DPA, C22:$5^{\Delta7,10,13,16,19}$) docosahexaenoic acid (=DHA, C22:$6^{\Delta4,7,10,13,16,19}$) or mixtures of these, preferably ARA, EPA and/or DHA. ω3-Fatty acids such as EPA and/or DHA are very especially preferably produced.

The fatty acid esters with polyunsaturated $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acylcoenzyme A esters which comprise the polyunsaturated fatty acids with at least two, three, four, five or six, preferably five or six double bonds, from the organisms which have been used for the preparation of the fatty acid esters; advantageously, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, advantageously in a transgenic plant. In this context, it is advantageous to convert $C_{18}$- and/or $C_{20}$-fatty acids which are present in the host organisms to at least 10%, advantageously to at least 20%, especially advantageously to at least 30%, most advantageously to at least 40% to give the corresponding products such as DPA or DHA, to mention just two examples. The fatty acids are advantageously produced in bound form. These unsaturated fatty acids can, with the aid of the nucleic acids used in the process according to the invention, be positioned at the sn1, sn2 and/or sn3 position of the advantageously produced triglycerides. Since a plurality of reaction steps are performed by the starting compounds linoleic acid (C18:2) and linolenic acid (C18:3) in the process according to the invention, the end products of the process such as, for example, arachidonic acid (ARA), eicosapentaenoic acid (EPA), ω6-docosapentaenoic acid or DHA are not obtained as absolutely pure products; minor traces of the precursors are always present in the end product. If, for example, both linoleic acid and linolenic acid are present in the starting organism and the starting plant, the end products such as ARA, EPA or DHA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA, EPA or only DHA, bound or as free acids, are produced as end products in a transgenic plant in the process according to the invention. If the compounds ARA, EPA and DHA are produced simultaneously, they are advantageously produced in a ratio of at least 3:2:1 (EPA:ARA:DHA).

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acid which is present in the fatty acid esters or fatty acid mixtures is preferably eicosapentaenoic acid. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselinic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (β-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, C22:$5^{\Delta4,8,12,15,21}$) and no nisinic acid (tetracosahexaenoic acid, C23:$6^{\Delta3,8,12,15,18,21}$).

Owing to the nucleic acid sequences of the invention, or the nucleic acid sequences used in the process according to the invention, an increase in the yield of polyunsaturated fatty acids of at least 50%, advantageously of at least 80%, especially advantageously of at least 100%, very especially advantageously of at least 150%, in comparison with the nontransgenic starting organism, for example a yeast, an alga, a fungus or a plant such as *Arabidopsis* or linseed can be obtained in a comparison by GC analysis.

Chemically pure polyunsaturated fatty acids or fatty acid compositions can also be prepared by the processes described above. To this end, the fatty acids or the fatty acid compositions are isolated from the organism, such as the microorganisms or the plants or the culture medium in or on which the organisms have been grown, or from the organism and the culture medium, in a known manner, for example via extraction, distillation, crystallization, chromatography or combinations of these methods. These chemically pure fatty acids or fatty acid compositions are advantageous for applications in the food industry sector, the cosmetic industry sector and especially the pharmacological industry sector.

In principle, all genes of the fatty acid or lipid metabolism can be used in the process for the production of polyunsaturated fatty acids, advantageously in combination with the inventive polynucleotide(s) (for the purposes of the present application, the plural is understood as encompassing the singular and vice versa). Genes of the fatty acid or lipid metabolism which are used are advantageously selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s). Genes selected from the group of the Δ4-desaturases, Δ5-desaturases, Δ6-desaturases, Δ8-desaturases, Δ9-desaturases, Δ12-desaturases, Δ15-desaturases, Δ12- and Δ15-desaturases, ω3-desaturases, Δ6-elongases, Δ9-elongases or Δ5-elongases in combination with the polynucleotides according to the invention are preferably used, it being possible to use individual genes or a plurality of genes in combination. For especially preferred gene combinations, reference is made here to tables 5 and 6, which are shown in the examples.

Advantageously, the desaturases used in the process according to the invention convert their respective substrates in the form of the CoA-fatty acid esters. If preceded by an elongation step, this advantageously results in an increased product yield. The respective desaturation products are thereby synthesized in greater quantities, since the elongation step is usually carried out with the CoA-fatty acid esters, while the desaturation step is predominantly carried out with the phospholipids or the triglycerides. Therefore, a substitution reaction between the CoA-fatty acid esters and the phospholipids or triglycerides, which would require a further, possibly limiting, enzyme reaction, is not necessary.

Owing to the enzymatic activity of the polypeptides used in the process according to the invention, a wide range of polyunsaturated fatty acids can be produced in the process according to the invention. Depending on the choice of the organisms, such as the preferred plants, used for the process according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, $C18:2^{\Delta 9,12}$) is present as unsaturated fatty acid in the plant used for the process, the process can only afford GLA, DGLA and ARA as products, all of which can be present as free fatty acids or in bound form. If only α-linolenic acid (=ALA, $C18:3^{\Delta 9,12,15}$) is present as unsaturated fatty acid in the plant used for the process, the process can only afford SDA, ETA, EPA and/or DHA as products, all of which can be present as free fatty acids or in bound form, as described above. Owing to the modification of the activity of the enzymes Δ5-desaturase, Δ6-desaturase, Δ4-desaturase, Δ12-desaturase, Δ15-desaturase, ω3-desaturase, Δ5-elongase and/or Δ6-elongase which play a role in the synthesis, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferably formed. If Δ5-desaturase, Δ5-elongase and Δ4-desaturase are additionally introduced into the organisms, advantageously into the plant, ARA, EPA and/or DHA are additionally formed. Advantageously, only ARA, EPA or DHA or mixtures of these are synthesized, depending on the fatty acids present in the organism, or in the plant, which acts as starting substance for the synthesis. Since biosynthetic cascades are involved, the end products in question are not present as pure substances in the organisms. Small amounts of the precursor compounds are always additionally present in the end product. These small amounts amount to less than 20% by weight, advantageously less than 15% by weight, especially advantageously less than 10% by weight, most advantageously less than 5, 4, 3, 2 or 1% by weight, based on the end product DGLA, ETA or their mixtures, or ARA, EPA, DHA or their mixtures, advantageously EPA or DHA or their mixtures.

In addition to the production, directly in the organism, of the starting fatty acids for the polypeptides used in the process of the invention, the fatty acids can also be fed externally. The production in the organism is preferred for reasons of economy. Preferred substrates are linoleic acid ($C18:2^{\Delta 9,12}$), γ-linolenic acid ($C18:3^{\Delta 6,9,12}$), eicosadienoic acid ($C20:2^{\Delta 11,14}$), dihomo-γ-linolenic acid ($C20:3^{\Delta 8,11,14}$), arachidonic acid ($C20:4^{\Delta 5,8,11,14}$) docosatetraenoic acid ($C22:4^{\Delta 7,10,13,16}$) and docosapentaenoic acid ($C22:5^{\Delta 4,7,10,13,15}$).

To increase the yield in the described process for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which codes for a polypeptide with a Δ12-desaturase and/or ω15-desaturase activity according to the invention. This is particularly advantageous in oil-producing organisms such as those from the family of the Brassicaceae, such as the genus *Brassica*, for example oilseed rape; the family of the Elaeagnaceae, such as the genus *Elaeagnus*, for example the genus and species *Olea europaea*, or the family Fabaceae, such as the genus *Glycine*, for example the genus and species *Glycine max*, which are high in oleic acid. Since these organisms are only low in linoleic acid (Mikoklajczak et al., Journal of the American Oil Chemical Society, 38, 1961, 678-681), the use of the abovementioned Δ12-desaturases and/or ω15-desaturases according to the invention for producing the starting material linoleic acid is advantageous.

The process according to the invention advantageously employs the abovementioned nucleic acid sequences or their derivatives or homologs which code for polypeptides which retain the enzymatic activity of the proteins encoded by nucleic acid sequences. These sequences, individually or in combination with the polynucleotides according to the invention, are cloned into expression constructs and used for the introduction into, and expression in, organisms. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with a polynucleotide according to the invention, a gene construct or a vector as described below, alone or in combination with further nucleic acid sequences which code for proteins of the fatty acid or lipid metabolism. In a further preferred embodiment, this process furthermore comprises the step of obtaining the oils, lipids or free fatty acids from the organism or from the culture. The culture can, for example, take the form of a fermentation culture, for example in the case of the cultivation of microorganisms, such as, for example, *Mortierella, Thalassiosira, Mantoniella, Ostreococcus, Saccharomyces* or *Thraustochytrium*, or a greenhouse- or field-grown culture of a plant. The cell or the organism thus produced is advantageously a cell of an oil-producing organism, such as an oil crop, such as, for example, peanut, oilseed rape, canola, linseed, hemp, soybean, safflower, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

Suitable organisms or host cells for the process according to the invention are those which are capable of synthesizing fatty acids, specifically unsaturated fatty acids, and/or which are suitable for the expression of recombinant genes. Examples which may be mentioned are plants such as *Arabidopsis, Asteraceae* such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Thraustochytrium, Saprolegnia, Phytophthora* or *Pythium*, bacteria, such as the genus *Escherichia* or *Shewanella*, yeasts, such as the genus *Saccharomyces*, cyanobacteria, ciliates, algae such as *Mantoniella* or *Ostreococcus*, or protozoans such as dinoflagellates, such as *Thalassiosira* or *Crypthecodinium*. Preferred organisms are those which are naturally capable of synthesizing substantial amounts of oil, such as fungi, such as *Mortierella alpina, Pythium insidiosum, Phytophthora infestans*, or plants such as soybean, oilseed rape, coconut, oil palm, safflower, flax, hemp, castor-oil plant, *Calendula*, peanut, cacao bean or sunflower, or yeasts such as *Saccharomyces cerevisiae*, with soybean, flax, oilseed rape, safflower, sunflower, *Calendula, Mortierella* or *Saccharomyces cerevisiae* being especially preferred. In principle, suitable as host organisms are, in addition to the abovementioned transgenic organisms, also transgenic animals, advantageously nonhuman animals, for example *Caenorhabditis elegans*. Further suitable host cells and organisms have already been described extensively above.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids. Polyunsaturated fatty acids produced by this process can be obtained by harvesting the organisms, either from the crop in which they grow, or from the field. This can be done via pressing or extraction of the plant parts, preferably of the plant seeds. In this context, the oils, fats, lipids and/or free fatty acids can be obtained by pressing by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvent such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, for example the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigments remaining in the product, the products are subjected to bleaching, for example using fuller's earth or active charcoal. At the end, the product is deodorized, for example using steam.

The PUFAs or LCPUFAs produced by this process are preferably $C_{18}$-, $C_{20}$- or $C_{22}$-fatty acid molecules, advantageously $C_{20}$- or $C_{22}$-fatty acid molecules, with at least two double bonds in the fatty acid molecule, preferably three, four, five or six double bonds. These $C_{18}$-, $C_{20}$- or $C_{22}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the abovedescribed process, especially preferably oil, lipid or a fatty acid composition comprising PUFAs and being derived from transgenic plants.

These oils, lipids or fatty acid compositions preferably comprise the abovementioned fatty acids, particularly preferably in the abovementioned concentration. In one embodiment of the invention, the oils, lipids or fatty acid compositions obtained by the methods according to the invention are distinguished by the fact that the preparations which comprise said oils, lipids or fatty acid compositions contain traces of the nucleic acids according to the invention. These traces can be detected by suitable highly-sensitive detection methods, for example PCR-based technologies.

A further embodiment according to the invention is the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. These oils, lipids, fatty acids or fatty acid mixtures, which are composed of vegetable and animal constituents, may also be used for the preparation of feedstuffs, foodstuffs, cosmetics or pharmaceuticals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular those mentioned above. The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds which are produced in the process are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least five or six double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the abovedescribed processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in "trans", so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains that also accumulate PUFAs in the triacylglycerol fraction are particularly advantageous for the process according to the invention and thus for the modification of the lipid and PUFA production system in a host, in particular plants such as oil crops, for example oilseed rape, canola, linseed, hemp, soybeans, sunflowers and borage. They can therefore be used advantageously in the process according to the invention.

Substrates which are suitable for the polypeptides according to the invention of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA: lyso-phospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) are preferably $C_{16}$-, $C_{18}$- or $C_{20}$-fatty acids. The fatty acids converted as substrates in the process are preferably converted in the form of their acyl-CoA esters and/or their phospholipid esters.

To produce the long-chain PUFAs according to the invention, the polyunsaturated C18-fatty acids must first be desaturated by the enzymatic activity of a desaturase and subsequently be elongated by at least two carbon atoms via an elongase. After one elongation cycle, this enzyme activity gives $C_{20}$-fatty acids and after two elongation cycles, C22-fatty acids. The activity of the desaturases and elongases used in the processes according to the invention preferably leads to $C_{18}$-, $C_{20}$- and/or $C_{22}$-fatty acids, advantageously with at least two double bonds in the fatty acid molecule, preferably with three, four, five or six double bonds, especially preferably to $C_{20}$- and/or $C_{22}$-fatty acids with at least two double bonds in the fatty acid molecule, preferably with three, four, five or six double bonds, very especially preferably with five or six double bonds in the molecule. After a first desaturation and the elongation have taken place, further desaturation and elongation steps such as, for example, such a desaturation in the 45 and 44 positions may take place. Products of the process according to the invention which are especially preferred are dihomo-γ-linolenic acid, arachidonic acid, eicosapentaenoic acid, docosapentaenoic acid and/or docosahexaenoic acid. The $C_{20}$-fatty acids with at least two double bonds in the fatty acid can be desaturated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of fatty acids, oils, lipids or fats in the plants which are advantageously used is, for example, in general the seed or cell strata of the seed, so that seed-specific expression of the nucleic acids used in the process is sensible. However, it is obvious that the biosynthesis of fatty acids, oils or lipids need not be limited to the seed tissue, but can also take place in a tissue-specific manner in all the other parts of the plant—for example in epidermal cells or in the tubers.

If microorganism such as yeasts, such as *Saccharomyces* or *Schizosaccharomyces*, fungi such as *Mortierella, Aspergillus, Phytophthora, Entomophthora, Mucor* or *Thraustochytrium*, algae such as *Isochrysis, Mantoniella, Ostreococcus, Phaeodactylum* or *Crypthecodinium* are used as organisms in the process according to the invention, these organisms are advantageously grown in fermentation cultures.

Owing to the use of the nucleic acids according to the invention which code for a desaturase, the polyunsaturated fatty acids produced in the process can be increased by at least 5%, preferably by at least 10%, especially preferably by at least 20%, very especially preferably by at least 50% in comparison with the wild type of the organisms which do not comprise the nucleic acids recombinantly.

In principle, the polyunsaturated fatty acids produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic organisms is enlarged by the process according to the invention.

If microorganisms are used as organisms in the process according to the invention, they are grown or cultured in a manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while introducing oxygen gas. The pH of the nutrient liquid can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview of known cultivation methods can be found in the textbook by Chmiel (Bioprozeβtechnik 1. Einfuhrung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for cultivating microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds depends heavily on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air, into the culture. The temperature of the culture is normally 20° C. to 45° C. and preferably 25° C. to 40° C. The culture is continued until formation of the desired product is at a maximum. This aim is normally achieved within 10 hours to 160 hours.

The fermentation broths obtained in this way, in particular those containing polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The polynucleotides or polypeptides of the present invention which are involved in the metabolism of lipids and fatty acids, PUFA cofactors and enzymes or in the transport of lipophilic compounds across membranes are used in the process according to the invention for the modulation of the production of PUFAs in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and *Tagetes*, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes leads to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only easily incorporated into triacylglycerol but also into membrane lipids.

Brassicaceae, Boraginaceae, Primulaceae, or Linaceae are particularly suitable for the production of PUFAs, for example stearidonic acid, eicosapentaenoic acid and docosahexaenoic acid. Linseed (*Linum usitatissimum*) is especially advantageously suitable for the production of PUFAs with the nucleic acid sequences according to the invention, advantageously, as described, in combination with further desaturases and elongases.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydratation reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, N.Y., and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool from the phospholipids. For further desaturation as described above, the fatty acid can be transferred back into the phospholipid pool. If appropriate, this reaction sequence can be traversed repeatedly.

Examples of precursors for the biosynthesis of PUFAs are oleic acid, linoleic acid and linolenic acid. These $C_{18}$-carbon fatty acids must be elongated to $C_{20}$ and $C_{22}$ in order to obtain fatty acids of the eicosa and docosa chain type. With the aid of the desaturases used in the process, such as the $\Delta 12$-, $\Delta 15$-, $\Delta 12$- and $\Delta 15$-, $\omega 3$-, $\Delta 4$-, $\Delta 5$- and $\Delta 6$-desaturases and/or the $\Delta 5$-, $\Delta 6$-elongases, arachidonic acid, eicosapentaenoic acid, docosapentaenoic acid or docosahexaenoic acid, advantageously eicosapentaenoic acid and/or docosahexaenoic acid, can be produced and subsequently employed in various applications regarding foodstuffs, feedstuffs, cosmetics or pharmaceuticals. $C_{20}$- and/or $C_{22}$-fatty acids with at least two, advantageously at least three, four, five or six, double bonds in the fatty acid molecule, preferably $C_{20}$- or $C_{22}$-fatty acids with advantageously four, five or six double bonds in the fatty acid molecule, can be prepared using the abovementioned enzymes. Desaturation may take place before or after elongation of the fatty acid in question. This is why the products of the desaturase activities and of the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the desaturases and elongases used in the process according to the invention are $C_{16}$-, $C_{18}$- or $C_{20}$-fatty acids such as, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid or arachidonic acid, eicosatetraenoic acid or eicosapentaenoic acid. The synthesized $C_{20}$- or $C_{22}$-fatty acids with at least two, three, four, five or six double bonds in the fatty acid are obtained in the process according to the invention in the form of the free fatty acid or in the form of their esters, for example in the form of their glycerides.

The term "glyceride" is understood as meaning a glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the process according to invention, a "glyceride" is furthermore understood as meaning glycerol derivatives. In addition to the abovedescribed fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantities and must therefore take up additional quantities, although they can be synthesized readily by other organisms such as bacteria; for example, cats have lost the ability to synthesize arachidonic acid in the course of evolution.

"Phospholipids" for the purposes of the invention are understood as meaning phosphatidylcholine, phosphatidylethanolamine, phosphatidylserine, phosphatidyl-glycerol and/or phosphatidylinositol, advantageously phosphatidylcholine. The terms "production or productivity" are known in the art and encompass the concentration of the fermentation product (compounds of the formula I) which is formed within a specific period of time and in a specific fermentation volume (for example kg of product per hour per liter). It also comprises the productivity within a plant cell or a plant, that is to say the content of the desired fatty acids produced in the process relative to the content of all fatty acids in this cell or plant. The term "production efficiency" comprises the time required for obtaining a specific production quantity (for example the time required by the cell to establish a certain throughput rate of a fine chemical). The term "yield or product/carbon yield" is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained, in a specific culture quantity over a specified period of time is increased. The terms "biosynthesis or biosynthetic pathway" are known in the art and comprise the synthesis of a compound, preferably an organic compound, by a cell from intermediates, for example in a multi-step and strongly regulated process. The terms "catabolism or catabolic pathway" are known in the art and comprise the cleavage of a compound, preferably of an organic compound, by a cell to give catabolites (in more general terms, smaller or less complex molecules), for example in a multi-step and strongly regulated process. The term "metabolism" is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

By employing, in the process according to the invention, the polynucleotides according to the invention and optionally further polynucleotides which code for enzymes of the lipid or fatty acid metabolism it is possible to achieve various advantageous effects. Thus, it is possible to influence the yield, production and/or production efficiency of the polyunsaturated fatty acids in a plant, preferably in an oil crop plant, or in a microorganism. The number or activity of the polypeptides or polynucleotides according to the invention can be increased, so that larger amounts of the gene products and, ultimately, larger amounts of the compounds of the general formula I are produced. A de novo synthesis in an organism, which, before the gene(s) in question was/were introduced, had been lacking the activity and ability to biosynthesize the compounds, is also possible. The same applies analogously to the combination with further desaturases or elongases or further enzymes of the fatty acid and lipid metabolism. The use of a variety of divergent sequences, i.e. sequences which differ at the DNA sequence level, may also be advantageous in this context, or else the use of gene expression promoters which makes possible a different gene expression as far as timing is concerned, for example as a function of the degree of maturity of a seed or oil-storing tissue.

By introducing, into an organism, a polynucleotide according to the invention alone or in combination with other genes in a cell it is possible not only to increase the biosynthetic flow towards the end product, but also to increase, or to create de novo, the corresponding triacylglycerol composition. Equally, the number or activity of other genes which are required for the import of nutrients for the biosynthesis of one or more fatty acids, oils, polar and/or neutral lipids can be increased, so that the concentration of these precursors, cofactors or intermediates within the cells or within the storage compartment is increased, whereby the ability of the cells to produce PUFAs is further enhanced. By optimizing the activity, or increasing the number, of one or more polynucleotides or polypeptides according to the invention which are involved in the biosynthesis of these compounds, or by destroying the activity of one or more genes which are involved in the degradation of these compounds, it may be possible to increase the yield, production and/or production efficiency of fatty acid and lipid molecules from organisms, in particular from plants. The fatty acids obtained in the process are suitable as starting materials for the chemical synthesis of further products of interest. For example, they can be used for the preparation of pharmaceuticals, foodstuffs, animal feeds or cosmetics, either alone or in combination with one another.

It can be seen from what has been said above that the invention also relates to a process for the preparation of an oil, lipid or fatty acid composition, comprising the steps of the process according to the invention and the further step of formulating the substance as an oil, lipid or fatty acid composition.

In a preferred embodiment of this process, the oil, lipid or fatty acid composition is formulated further to give a drug, a cosmetic product, a foodstuff, a feedstuff, preferably fish food, or a food supplement.

Finally, the invention relates to the principle of using the polynucleotide, the vector, the host cell, the polypeptide or the transgenic, nonhuman organism of the present invention for the production of an oil, lipid or fatty acid composition. The latter should then preferably be employed as drug, cosmetic product, foodstuff, feedstuff, preferably fish food, or food supplement.

The content of all the references, patent applications, patents and published patent applications cited in the present patent application is hereby incorporated by reference to the respective specific disclosure.

FIGURES

FIG. 1: Biosynthetic pathways for the production of long-chain, polyunsaturated fatty acids such as arachidonic acid (=ARA, C20:$4^{\Delta 5,8,11,14}$) eicosapentaenoic acid (=EPA, C20:$5^{\Delta 5,8,11,14,17}$) or docosahexaenoic acid (=DHA, C22:$6^{\Delta 4,7,10,13,16,19}$).

Figure 2:
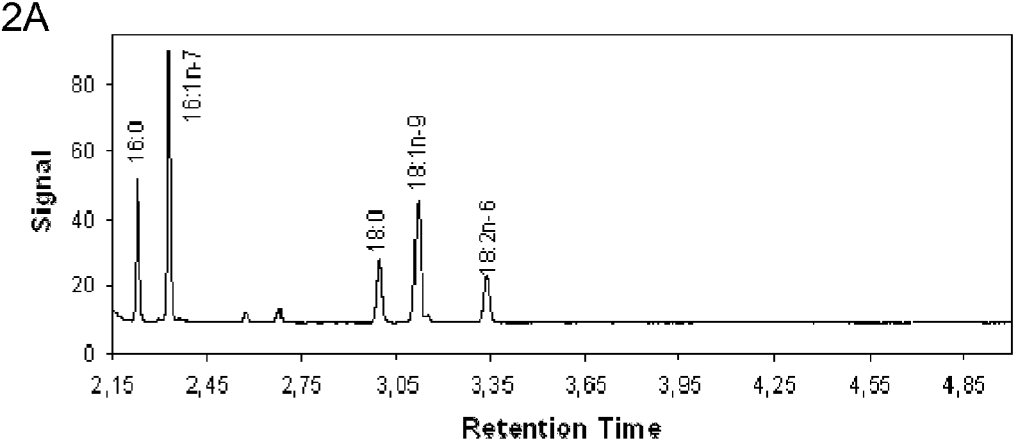
Figure 2:
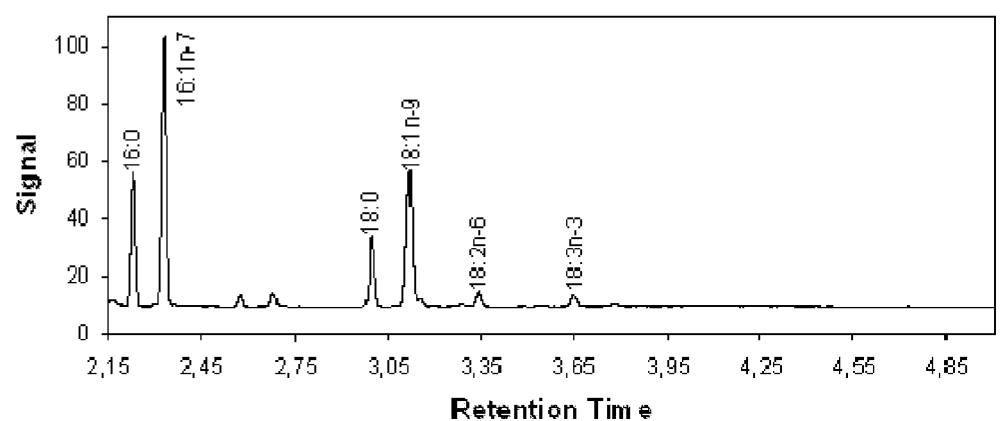
Figure 2:
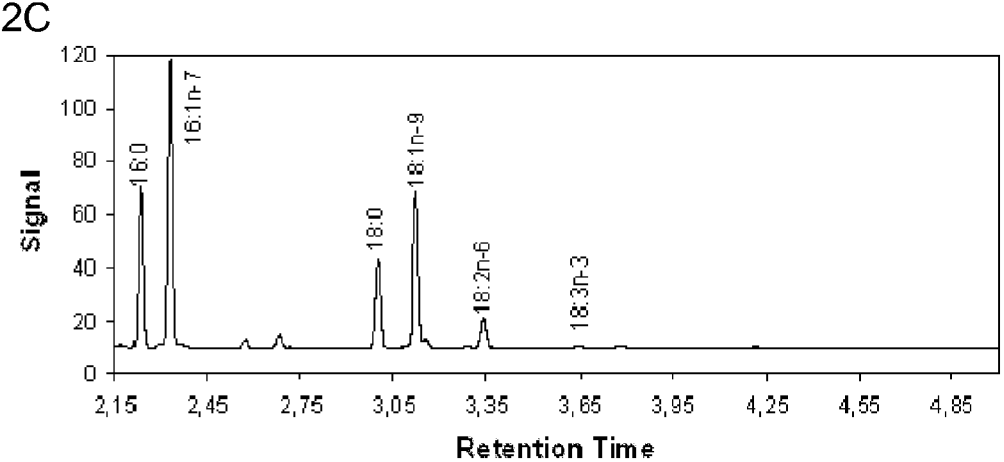

FIG. 2: Gas-chromatographic determination of the fatty acids from yeasts which have been transformed with the plasmid pYES (A) or pYES-d15Des(Ch) (B) and pYES-d15Des(Cy) (C), respectively.

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the method of Sanger (Sanger et al. (1977) Proc. Natl. Acad. Sci. USA74, 5463-5467). Fragments obtained by polymerase chain reaction were sequenced and verified to avoid polymerase errors in constructs to be expressed.

Example 3

Lipid Extraction from Yeasts

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of the desired product (i.e. of lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Better, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research", Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for the production of the desired compound, such as intermediates and by-products, in order to determine the overall production efficiency of the compound. The analytical methods comprise measuring the amount of nutrients in the medium (for example sugars, hydrocarbons, nitrogen sources, phosphate and other ions), measuring the biomass composition and the growth, analyzing the production of conventional metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas liquid chromatography/mass spectrometry; TAG, triacylglycerol; TLC, thin-layer chromatography).

Unambiguous proof for the presence of fatty acid products can be obtained by analyzing recombinant organisms using standard analytical methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometry methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 micrometer, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Example 4

Cloning Desaturase Genes

The fungus *Mycocentrospora acerina* was grown for five days at 25° C. in 50 ml of liquid medium (3 g/l yeast extract, 3 g/l malt extract, 3 g/l peptone, 10 g/l glucose, 0.68 g/l $K_2HPO_4$ pH 6.0) on a shaker at 200 rpm. After the cells were harvested by centrifugation at 2000×g, 5 min, 4° C., 2 g of cell pellet were obtained. The pellet was washed 3× with distilled water. Total-RNA was isolated using the RNeasy plant mini Kit (Quiagen, Hilden, Germany) in accordance with the manufacturer's instructions. This RNA was employed in order to obtain "5'RACE-ready" and "3'-RACE ready" cDNA using the SMART RACE cDNA Amplification Kit (Clontech, Heidelberg, Germany), following the manufacturer's instructions. To isolate novel desaturase genes, the following degenerate primers were employed in combination with the "5'-RACE ready" cDNA:

```
Deg. 1 (SEQ ID No.: 42):
5'-TGGGTI(C/T)T(T/C/G)GCICA(C/T)GA(A/G)TG(C/T)
GG(A/T/C)CA-3'

Deg. 2 (SEQ ID No.: 43):
5'-TTIGG(A/G)TCIGT(A/G)TG(C/T)TG(A/C/G)A(A/G)
(A/G)AAIGT-3'
```

The following PCR protocol was employed for the amplification:

a) 2 min at 95° C.,
b) 30 sec at 94° C.
   30 sec at 55-72° C.
   2 min at 72° C.
   Number of cycles: 30
c) 10 min at 72° C.

PCR amplificates were sequenced after having been cloned into pCR2.1-TOPO (Invitrogen, Karlsruhe, Germany) following the manufacturer's instructions. One sequence showed homology to known Δ-12 and Δ-15 desaturases (Sayanova O et al. J. Biol. Chem., 2006, 281, 36533-36541) in the ClustalW alignment (Thompson J D, et al., Nucleic Acids Res., 1994, 22: 4673-4680). This known sequence section was extended at both ends (5' and 3') by Rapid Amplification of cDNA Ends (RACE) by means of the SMART RACE cDNA Amplification Kit (Clontech, Heidelberg, Germany). To this end, the following sequence-specific primers were derived in the known sequence region:

```
5RACE1 (SEQ ID No.: 44):
5'-ATGAAGACCATGTCGCGCTCCATGT-3'

3RACE1 (SEQ ID No.: 45):
5'-GACGAGCACCTCATCCTGCTTAG-3'
```

These primers in combination with the "5'-RACE ready" or "3'-RACE ready" cDNA of the fungus *Mycocentrospora acerin* gave the complete mRNA sequence (SEQ ID No.:15, Table 1).

For the other candidate sequences listed, complete genomic sequences were identified in a first step, in accordance with database entries. In a further step, the coding sequence was extracted with the aid of methods of bioinformatics. In order to obtain the corresponding coding sequence from the organisms, these can be amplified in a PCR reaction from cDNA preparations, using the primer sequences defined in Table 1. This may give rise to fragments as are described in Table 2.

By searching for conserved regions in the protein sequences, derived from the DNA, of the organisms *Cochliobolus heterostrophus* C5, *Cyanothece* sp. CCY0110 and *Mycocentrospora acerina*, it was possible to identify sequences with putative Δ12-desaturase activity or Δ15-desaturase activity. In particular when a succession of the desaturase motif 1 "$GX_{10}HX_3HX_{13}GX_9PX_3WX_3H$" (SEQ ID No: 46), the desaturase motif 2 "$PX_{14}(H/Q)H$" (SEQ ID No: 47) and either the desaturase motif 3 "$HX_2HHX_5PXY$" (SEQ ID No: 48) or the desaturase motif 4 "$HX_2HHX_6PXY$" (SEQ ID No: 49) are found in the sequence, this is indicative of Δ12-desaturases or Δ15-desaturases, where X stands for any amino acid. Whether it is a putative Δ12-, Δ15- or omega3-desaturase can be deduced from the amino acid at the variable position 16 of the desaturase motif 2 (H or Q): Q=glutamine is indicative of putative Δ12-desaturases, H=histidine is indicative of putative Δ15- or omega3-desaturases.

TABLE 1

Primer sequences for cloning the desaturases which have been identified.

| Name of gene | Organism | Primer sequence (5'-3') | SEQ ID No: |
| --- | --- | --- | --- |
| D15Des(Ch) | *Cochliobolus heterostrophus* C5 | Forward: atgattacgactacgcacc<br>Reverse: ttaagccttggtcttggacc | 4<br>6 |
| D15Des(Cy) | *Cyanothece* sp. CCY0110 | Forward: atgcagcaacctatgactgtg<br>Reverse: ttaaaactttctagattcac | 11<br>13 |
| D12Des(Mac) | *Mycocentrospora acerina* | Forward: atggcctcgaccaccgccgc<br>Reverse: ttactcgttgtcactctcag | 18<br>19 |
| ω3Des(Hp) | *Hyaloperonospora parasitica* | Forward: atggcgaccaagcaatcgg<br>Reverse: ctaagctgctttggcatcac | 53<br>55 |

TABLE 2

Coding polynucleotide or amino acid sequences of the desaturases which have been identified.

| Name of gene | Organism | Nucleotides in bp | SEQ ID No: | Amino acids | SEQ ID |
| --- | --- | --- | --- | --- | --- |
| D15Des (Ch) | *Cochliobolus heterostrophus* C5 | 1215 | 2 | 404 | 3 |
| D15Des (Cy) | *Cyanothece* sp. CCY0110 | 1050 | 9 | 349 | 10 |
| D12 Des (Mac) | *Mycocentrospora acerina* | 1488 | 16 | 495 | 17 |

TABLE 2-continued

Coding polynucleotide or amino acid sequences of the desaturases which have been identified.

| Name of gene | Organism | Nucleotides in bp | SEQ ID No: | Amino acids | SEQ ID |
|---|---|---|---|---|---|
| ω3Des (Hp) | Hyaloperonospora parasitica | 1086 | 51 | 361 | 52 |

TABLE 3

Genomic sequence (gDNA) or transcript sequences (mRNA) of the desaturases which have been identified.

| Name of gene | Organism | Type of sequence | Nucleotides in bp | SEQ ID |
|---|---|---|---|---|
| D15Des(Ch) | Cochliobolus heterostrophus C5 | gDNA | 1870 | 1 |
| D15Des(Cy) | Cyanothece sp. CCY0110 | gDNA | 1667 | 4 |
| D12 Des(Mac) | Mycocentrospora acerina | mRNA | 1932 | 7 |
| ω3Des(Hp) | Hyaloperonospora parasitica | gDNA | 1300 | 50 |

To characterize the functions of the individual sequences, the open reading frame of the DNA (Table 2) is cloned downstream of the galactose-inducible GAL1 promoter of pYES2.1/V5-His-TOPO (Invitrogen), giving rise to the plasmids pYES-D15Des(Ch), pYES-D15Des(Cy) or pYes-D12Des(Mac). Then, following manufacturer's instructions, these plasmids can then be transformed into the yeast strain INVSC-1 (Invitrogen) and selected for uracil auxotrophism on plates with DOB-U agar. Positive colonies are identified by PCR. To this end, PCR is carried out in each case with 1 µl of defrosted cells, 200 µM dNTPs, 2.5 U Taq-polymerase and 100 pmol of each primer in a total volume of 50 µl. The PCR conditions are as follows: first denaturation at 95° C. for 5 minutes, followed by 30 cycles at 94° C. for 30 seconds, 55° C. for 1 minute and 72° C. for 2 minutes, and a last elongation step at 72° C. for 10 minutes. In parallel, the empty vector pYES2.1/V5-His-TOPO is transformed in the above-described manner into competent yeast cells of strain INVSC-1. Yeast cells with the plasmids pYES-D15Des(Ch), pYES-D15Des(Cy) or pYes-D12Des(Mac) are incubated for 12 h in liquid DOB-U medium at 28° C. and 200 rpm and then grown for a further 12 h in induction medium (DOB-U+2% (w/v) galactose+2% (w/v) raffinose) and 250 µM of fatty acids which are added into the medium. The specificity and activity of the gene to be characterized can be determined with reference to the added fatty acids.

Yeasts transformed with the plasmids pYES2/V5-His-TOPO or pYES-D15Des(Ch), pYES-D15Des(Cy) or pYes-D12Des(Mac) are analyzed as follows:

The yeast cells from the main cultures are harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) are prepared by acid methanolysis. To this end, the cell sediments are incubated for one hour at 80° C. together with 2 ml of 1 N methanolic sulfuric acid and 2% (v/v) of dimethoxypropane. The FAMEs are extracted twice with petroleum ether (PE). To remove nonderivatized fatty acids, the organic phases are washed in each case once with 2 ml of 100 mM NaHCO$_3$, pH 8.0 and 2 ml of distilled water. Thereafter, the PE phases are dried with Na$_2$SO$_4$, evaporated under argon and taken up in 100 µl of PE. The samples are separated on a DB-23 capillary column (30 m, 0.25 mm, 0.25 µm, Agilent) in a Hewlett-Packard 6850 gas chromatograph equipped with flame ionization detector. The conditions for the GLC analysis are as follows: the oven temperature was programmed from 50° C. to 250° C. with an increment of 5° C./min and finally 10 min at 250° C. (holding).

The signals are identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Activity and Substrate Determination of the Desaturases which have been Identified The substrate specificity of D15Des(Ch) or D15Des(Cy) can be determined after expression and after the feeding of various fatty acids. Departing from the conserved desaturase motif 2 (SEQ ID No. 47), the following activity was found for the coding sequences (Table 4).

TABLE 4

Activity of the desaturases which have been identified

| Name of gene | Organism | Activity | Polynucleotide SEQ ID NO: | Polypeptide SEQ ID NO: |
|---|---|---|---|---|
| D15Des (Ch) | Cochliobolus heterostrophus C5 | Δ15-desaturase | 2 | 3 |
| D15Des (Cy) | Cyanothece sp. CCY0110 | Δ15-desaturase | 5 | 6 |
| ω3Des (Hp) | Hyaloperonospora parasitica | ω3-desaturase | 51 | 52 |

These activities which have been found were additionally verified by expressing the desaturases in yeast. Table 4A lists the conversion of various fatty acid substrates into the expected fatty acid products. Except for the fatty acid 18:1n-9, all substrates were fed in the experiment and are therefore present in excess. FIG. 2 shows the chromatograms of the individual experiments.

TABLE 4A

| | Reaction step observed | | | | |
|---|---|---|---|---|---|
| Sample name/fatty acid | Substrate (% of total fatty acid content) | Product (% of total fatty acid content) | Conversion rate (%) Expected | Observed | Activity observed | FIG. |
| pYES2 empty vector/ 18:2n-9 | 18:2n-6  25.3 | 18:3n-3  0.0 | — | — | — | 2A |
| d15Des(Ch)/18:2n-9 | 18:2n-6  6.3 | 18:3n-3  5.7 | >0 | 47.5 | Δ15-des. | 2B |
| d15Des(Cy)/18:2n-9 | 18:2n-6  13.0 | 18:3n-3  0.9 | >0 | 6.4 | Δ15-des. | 2C |

TABLE 4A-continued

| | Reaction step observed | | | | | |
|---|---|---|---|---|---|---|
| | Substrate (% of total fatty | Product (% of total fatty | Conversion rate (%) | | Activity | |
| Sample name/fatty acid | acid content) | acid content) | Expected | Observed | observed | FIG. |
| ω3Des(Hp)/18:2n-9 | 18:2n-6  12.6 | 18:3n-3  0.0 | >0 | 0.0 | — | |
| ω3Des(Hp)/20:3n-6 | 20:3n-6  6.3 | 20:4n-3  0.6 | >0 | 8.6 | ω3-Des | |
| ω3Des(Hp)/20:4n-6 | 20:4n-6  5.7 | 20:5n-3  1.8 | >0 | 24.0 | ω3-Des | |

By way of control for the assay for Δ15-desaturase activity, yeasts were transformed with the pYES empty vector, the fatty acid 18:2n-6 was fed, and the fatty acid profile was analyzed (FIG. 2A). In comparison, the additional fatty acid 18:3n-3 can be observed in yeasts which express the desaturases d15Des(Ch) and d15Des(Cy) (FIG. 2B, 2C). These desaturases which have been assayed therefore have Δ15-desaturase activity.

Example 5

Production of Transgenic Plants for the Production of Long-Chain Polyunsaturated Fatty Acids To produce long-chain polyunsaturated fatty acids in plants, various genes of the metabolic pathway are combined on a binary vector. To produce the fatty acid eicosapentaenoic acid (20:5Δ5,8,11,14,17), genes as described in Table 5 are combined. Analogously, the genes as described in Table 6 are combined for producing the fatty acid docosahexaenoic acid (22:6Δ4,7,10,13,16,19).

TABLE 5

Gene combination for the production of eicosapentaenoic acid

| Gene | Activity | SEQ ID NO: |
|---|---|---|
| D6Des(Pir) | Δ6-desaturase | 22 |
| D6Elo(Pp) | Δ6-elongase | 31 |
| D5Des(Tc) | Δ5-desaturase | 25 |
| ω3-Des(Pi) | ω3-desaturase | 28 |
| D15Des(Ch) | Δ15-desaturase | 2 |
| D15Des(Cy) | Δ15-desaturase | 9 |
| D12Des(Mac) | Δ12-/Δ15-desaturase | 16 |
| ω3Des(Hp) | ω3-desaturase | 51 |

TABLE 6

Gene combination for the production of docosahexaenoic acid

| Gene | Activity | SEQ ID NO: |
|---|---|---|
| D6Des(Pir) | Δ6-desaturase | 22 |
| D6Elo(Pp) | Δ6-elongase | 31 |
| D5Des(Tc) | Δ5-desaturase | 25 |
| ω3Des(Pi) | ω3-desaturase | 28 |
| D15Des(Ch) | Δ15-desaturase | 2 |
| D15Des(Cy) | Δ15-desaturase | 9 |
| ω3Des(Hp) | ω3-desaturase | |
| D12Des(Mac) | Δ12-/Δ15-desaturase | 16 |
| D5Elo(Ot) | Δ5-elongase | 34 |
| D4 Des(Tc) | Δ4-desaturase | 37 |

Further transformation vectors based on pSUN-USP were generated for the transformation of plants. To this end, NotI cleavage sites were introduced at the 5' and at the 3' end of the coding sequence, using the following primer pairs (see Table 7).

Composition of the PCR Mix (50 µl):

5.00 µl template cDNA 5.00 µl 10× buffer (Advantage polymerase)+25 mM MgCl$_2$ 5.00 µl 2 mM dNTP 1.25 µl of each primer (10 pmol/µL)

0.50 µl Advantage polymerase

The Advantage polymerase from Clontech is employed.

PCR Reaction Conditions:

Annealing temperature: 1 min 55° C.

Denaturation temperature: 1 min 94° C.

Elongation temperature: 2 min 72° C.

Number of cycles: 35

TABLE 7

Primer sequences
(for cloning transformation vectors based on pSUN-USP)

| Gene | Primer | | SEQ ID No. |
|---|---|---|---|
| D6-Des(Pir) | Fwd: | gcggccgcgccatggtggacctcaagcctgg | 23 |
| | Rvs: | gcggccgttacatcgctgggaactcgg | 24 |
| D5-Des(Tc) | Fwd: | gcggccgcgccatgggcaagggcagcgaggg | 26 |
| | Rvs: | gcggccgcgcctcagtcctgcttcttggtgc | 27 |
| O3-Des(Pi) | Fwd: | gcggccgcgccatggcgacgaaggaggcgta | 29 |
| | Rvs: | gcggccgcgttacgtggacttggtcttggcc | 30 |
| D6-Elo(Pp) | Fwd: | gcggccgcgccatggaggtcgtggagagattc | 32 |
| | Rvs: | gcggccgcgtcactcagttttagctccc | 33 |
| D15Des(Ch) | Fwd: | gcggccgcgccatgattacgactacgcacc | 5 |
| | Rvs: | gcggccgcgttaagccttggtcttggacc | 7 |

TABLE 7-continued

Primer sequences
(for cloning transformation vectors based on pSUN-USP)

| Gene | Primer | | SEQ ID No. |
|---|---|---|---|
| D15Des(Cy) | Fwd: | gcggccgcgccatgcagcaacctatgactgtg | 12 |
| | Rvs: | gcggccgcgttaaaactttctagattcac | 14 |
| D12Des(Mac) | Fwd: | gcggccgcgccatggcctcgaccaccgcccgc | 20 |
| | Rvs: | gcggccgcgttactcgttgtcactctcag | 21 |
| ω3Des(Hp) | Fwd: | gcggccgcgccatggcgaccaagcaatcgg | 54 |
| | Rvs: | gcggccgcgctaagctgctttggcatcac | 56 |
| D5Elo(Ot) | Fwd: | gcggccgcgccatgagcgcctccggtgcgctg | 35 |
| | Rvs: | gcggccgcgttagtcaatttttc | 36 |
| D4Des(Tc) | Fwd: | gcggccgcgccatgacggtcggctacgacgag | 38 |
| | Rvs: | gcggccgcgtcaggcagcgcgctgccagg | 39 |

The PCR products are incubated with the restriction enzyme NotI for 4 h at 37° C. The plant expression vector pSUN300-USP is incubated in the same manner. Thereafter, the PCR products and the 7624 bp vector are separated by agarose gel electrophoresis, and the corresponding DNA fragments are excised. The DNA is purified by means of the Qiagen gel purification kit, following the manufacturer's instructions. Thereafter, vector and PCR products are ligated. The Rapid Ligation kit from Roche is used for this purpose. The plasmids generated are verified by sequencing.

pSUN300 is a derivative of the plasmid pPZP (Hajdukiewicz, P, Svab, Z, Maliga, P., (1994) The small versatile pPZP family of Agrobacterium binary vectors for plant transformation. Plant Mol Biol 25:989-994). pSUN-USP originated from pSUN300, by inserting a USP promoter into pSUN300 in the form of an EcoRI fragment. The polyadenylation signal is the OCS gene from the A. tumefaciens Ti plasmid (ocs-Terminator, Genbank Accession V00088) (De Greve, H., Dhaese, P., Seurinck, J., Lemmers, M., Van Montagu, M. and Schell, J. Nucleotide sequence and transcript map of the Agrobacterium tumefaciens Ti plasmid-encoded octopine synthase gene J. Mol. Appl. Genet. 1 (6), 499-511 (1982). The USP promoter corresponds to nucleotides 1 to 684 (Genbank Accession X56240), where part of the noncoding region of the USP gene is present in the promoter. The promoter fragment which is 684 base pairs in size was amplified by a PCR reaction using standard methods with the aid of a synthesized primer and by means of a commercially available T7 standard primer (Stratagene) (Primer Sequence:

[SEQ ID NR: 82]
5'-GTCGACCCGCGGACTAGTGGGCCCTCTAGACCCGGGGGATCC

GGATCTGCTGGCTATGAA-3').

The PCR fragment was recut with EcoRI/SalI and inserted into the vector pSUN300 with OCS terminator. This gave rise to the plasmid named pSUN-USP, which can be employed for transforming plants by means of Agrobacterium tumefaciens.

a) Generation of Transgenic Oilseed Rape Plants (Modified Method of Moloney et al., 1992, Plant Cell Reports, 8:238-242)

To generate transgenic oilseed rape plants, binary vectors such as the pSUN plasmids described hereinabove are transformed into Agrobacterium tumefaciens C58C1:pGV2260 (Deblaere et al, 1984, Nucl. Acids. Res. 13, 4777-4788). A 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) is used for transforming oilseed rape plants (cv. Westar). Petioles or hypocotyls of freshly germinated sterile oilseed rape plants (in each case approx. 1 cm$^2$) are incubated with a 1:50 agrobacterial dilution for 5-10 minutes in a Petri dish. This is followed by 3 days of coincubation in the dark at 25° C. on 3MS medium supplemented with 0.8% Bacto agar. After 3 days, the cultivation is continued with 16 hours light/8 hours dark and is continued, in a 1-week rhythm, on MS medium supplemented with 500 mg/l Claforan (cefotaxim-sodium), 50 mg/l kanamycin, 20 µM benzylaminopurine (BAP) and 1.6 g/l glucose. Growing shoots are transferred to MS medium supplemented with 2% sucrose, 250 mg/l Claforan and 0.8% Bacto agar. If no roots have formed after three weeks, the growth hormone 2-indolebutyric acid is added to the medium to promote rooting.

Regenerated shoots are obtained on 2MS medium supplemented with kanamycin and Claforan, transferred into soil once rooted, and after cultivation for two weeks grown in a controlled-environment cabinet or in a greenhouse, flowering is induced, mature seeds are harvested and analyzed for expression of the desaturase or elongase genes by means of lipid analyses as described by way of example in Qiu et al. 2001, J. Biol. Chem. 276, 31561-31566.

b) Generation of Transgenic Linseed Plants

Transgenic linseed plants can be generated for example by the method of Bell et al., 1999, In Vitro Cell. Dev. Biol.-Plant. 35(6):456-465 by means of particle bombardment. Agrobacterial-mediated transformations can be effected for example as described by Mlynarova et al. (1994), Plant Cell Report 13: 282-285.

We claim:

1. A polynucleotide comprising a nucleic acid sequence operably linked to a heterologous expression control sequence, wherein said nucleic acid sequence is selected from the group consisting of:
   (a) the nucleic acid sequence of SEQ ID NO: 1 or 2;
   (b) a nucleic acid sequence which encodes a polypeptide comprising the amino acid sequence of SEQ ID NO: 3; and
   (c) a nucleic acid sequence which encodes a polypeptide having Δ15-desaturase activity and comprising an amino acid sequence having at least 70% sequence identity to the amino acid sequence of SEQ ID NO: 3,
   wherein said polypeptide comprises the desaturase motif 2 of SEQ ID NO: 47, and wherein position 16 of SEQ ID NO: 47 is histidine.

2. The polynucleotide of claim 1, wherein the polynucleotide consists of RNA or DNA.

3. A vector comprising the polynucleotide of claim 1.

4. The vector of claim 3, wherein the vector is an expression vector.

5. The vector of claim 3, wherein the vector comprises at least one further polynucleotide which encodes a further enzyme which is involved in the biosynthesis of lipids or fatty acids.

6. A host cell comprising the polynucleotide of claim 1.

7. The host cell of claim 6, wherein the host cell additionally comprises at least one further enzyme which is involved in the biosynthesis of lipids or fatty acids.

8. The host cell of claim 7, wherein the enzyme is selected from the group consisting of: acyl-CoA dehydrogenase(s), acyl carrier protein (acyl-ACP) desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), Δ4-desaturase(s), Δ5-desaturase(s), Δ6-desaturase(s), Δ8-desaturase(s), Δ9-desaturase(s), Δ12-desaturase(s), Δ5-elongase(s), Δ6-elongase(s) and Δ9-elongase(s).

9. A method of generating a polypeptide with Δ15-desaturase activity, comprising:
   (a) expressing the polynucleotide of claim 1 in a host cell; and
   (b) obtaining from the host cell the polypeptide encoded by said nucleic acid sequence.

10. A transgenic, nonhuman organism comprising the polynucleotide of claim 1.

11. The transgenic, nonhuman organism of claim 10, wherein the organism is an animal, a plant, or a microorganism.

12. A method of producing a transgenic, nonhuman organism or cell comprising transforming a nonhuman organism or cell with the polynucleotide of claim 1 or a vector comprising said polynucleotide.

13. A process for the production of a substance which has the structure shown in the general formula I herein below

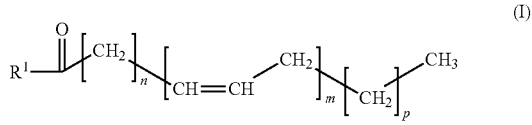

(I)

wherein the variables and substituents are as follows:
$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

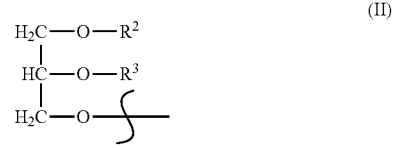

(II)

$R^2$=hydrogen, phosphatidylcholine, phosphatidylethanolamine, phosphatidylglycerol, diphosphatidylglycerol, phosphatidylserine, phosphatidylinositol or saturated or unsaturated $C_2$ to $C_{24}$-alkylcarbonyl, $R^3$=hydrogen, a saturated or unsaturated $C_2$ to $C_{24}$-alkylcarbonyl, or $R^2$ and $R^3$ independently of one another are a radical of the formula Ia:

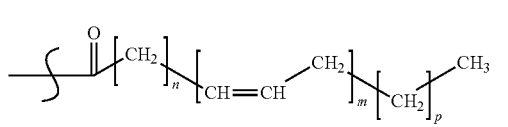
(Ia)

n=2, 3, 4, 5, 6, 7 or 9, m=2, 3, 4, 5 or 6 and p=0 or 3; comprising cultivating the host cell of claim 6 under conditions which permit the biosynthesis of the substance.

14. A process for the production of a substance which has the structure shown in the general formula I herein below

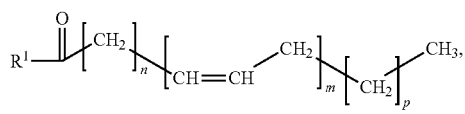
(I)

wherein the variables and substituents are as follows:

$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

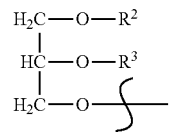
(II)

$R^2$=hydrogen, phosphatidylcholine, phosphatidylethanolamine, phosphatidylglycerol, diphosphatidylglycerol, phosphatidylserine, phosphatidylinositol or saturated or unsaturated $C_2$ to $C_{24}$-alkylcarbonyl, $R^3$=hydrogen, a saturated or unsaturated $C_2$ to $C_{24}$-alkylcarbonyl, or $R^2$ and $R^3$ independently of one another are a radical of the formula Ia:

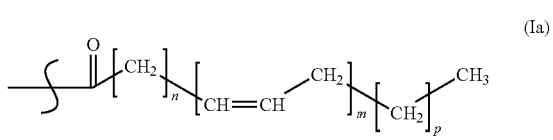
(Ia)

n=2, 3, 4, 5, 6, 7 or 9, m=2, 3, 4, 5 or 6 and p=0 or 3;

comprising cultivating the transgenic, nonhuman organism of claim 10 under conditions which permit the biosynthesis of the substance.

15. The process of claim 13, further comprising
(a) obtaining the substance produced; and
(b) formulating the substance as an oil, lipid or fatty acid composition.

16. The process of claim 15, wherein the oil, lipid or fatty acid composition is formulated further to give a drug, cosmetic product, foodstuff, feedstuff, fish food, or food supplement.

17. The process of claim 14, further comprising
(a) obtaining the substance produced; and
(b) formulating the substance as an oil, lipid or fatty acid composition.

18. The process of claim 17, wherein the oil, lipid or fatty acid composition is formulated further to give a drug, cosmetic product, foodstuff, feedstuff, fish food, or food supplement.

19. The polynucleotide of claim 1, wherein said nucleic acid sequence encodes a polypeptide having Δ15-desaturase activity and comprising an amino acid sequence having at least 85% sequence identity to the amino acid sequence of SEQ ID NO: 3.

* * * * *